United States Patent
Lugovskoy

(10) Patent No.: US 11,384,152 B2
(45) Date of Patent: Jul. 12, 2022

(54) THERAPEUTIC ANTI-CD40 LIGAND ANTIBODIES

(71) Applicant: ALS Therapy Development Institute, Cambridge, MA (US)

(72) Inventor: Alexey Lugovskoy, Belmont, MA (US)

(73) Assignee: ALS THERAPY DEVELOPMENT INSTITUTE, Cambridge, MA (US)

( * ) Notice: Subject to any disclaimer, the term of this patent is extended or adjusted under 35 U.S.C. 154(b) by 29 days.

(21) Appl. No.: 16/615,757

(22) PCT Filed: May 23, 2018

(86) PCT No.: PCT/US2018/034172
§ 371 (c)(1),
(2) Date: Nov. 21, 2019

(87) PCT Pub. No.: WO2018/217918
PCT Pub. Date: Nov. 29, 2018

(65) Prior Publication Data
US 2020/0223932 A1    Jul. 16, 2020

Related U.S. Application Data

(60) Provisional application No. 62/510,471, filed on May 24, 2017.

(51) Int. Cl.
*C07K 16/28* (2006.01)
*A61K 39/395* (2006.01)

(52) U.S. Cl.
CPC ........ *C07K 16/2875* (2013.01); *A61K 39/395* (2013.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,474,771 A | 12/1995 | Lederman et al. |
| 5,637,481 A | 6/1997 | Ledbetter et al. |
| 5,851,795 A | 12/1998 | Linsley et al. |
| 5,961,974 A | 10/1999 | Armitage et al. |
| 5,962,406 A | 10/1999 | Armitage et al. |
| 6,001,358 A | 12/1999 | Black et al. |
| 6,328,964 B1 | 12/2001 | Noelle et al. |
| 6,340,459 B1 | 1/2002 | Yellin et al. |
| 6,376,459 B1 | 4/2002 | Aruffo et al. |
| 6,451,310 B1 | 9/2002 | Lederman et al. |
| 6,838,261 B1 | 1/2005 | Siegall et al. |
| 7,070,777 B1 | 7/2006 | Lederman et al. |
| 7,169,389 B2 | 1/2007 | Di Padova et al. |
| 7,173,046 B2 | 2/2007 | Zheng et al. |
| 7,547,438 B2 | 6/2009 | Thomas et al. |
| 7,563,443 B2 | 7/2009 | Grant et al. |
| 7,647,438 B1 | 1/2010 | Norrie et al. |
| 7,863,419 B2 | 1/2011 | Taylor et al. |
| 8,293,237 B2 | 10/2012 | Burkly et al. |
| 8,435,514 B2 | 5/2013 | Perrin et al. |
| 8,647,625 B2 | 2/2014 | Van Vlijmen et al. |
| 8,784,823 B2 | 7/2014 | Burkly et al. |
| 8,895,010 B2 | 11/2014 | Nadler et al. |
| 8,981,072 B2 | 3/2015 | Nadler et al. |
| 9,028,826 B2 | 5/2015 | Noelle |
| 9,044,459 B2 | 6/2015 | Perrin et al. |
| 9,228,018 B2 | 1/2016 | Nadler et al. |
| 10,106,618 B2 | 10/2018 | Lincecum |
| 10,683,356 B2 | 6/2020 | Lincecum |
| 11,014,990 B2 | 5/2021 | Lincecum et al. |
| 2001/0018041 A1 | 8/2001 | Hanna et al. |
| 2004/0006208 A1 | 1/2004 | Karpusas et al. |
| 2004/0110226 A1* | 6/2004 | Lazar ............... C07K 16/22 435/7.1 |
| 2007/0048300 A1 | 3/2007 | Taylor et al. |
| 2007/0190053 A1 | 8/2007 | Kalled et al. |
| 2008/0138349 A1 | 6/2008 | Stavenhagen et al. |
| 2011/0172400 A1 | 7/2011 | Grant et al. |
| 2012/0251531 A1 | 3/2012 | Baehner et al. |
| 2013/0045219 A1 | 2/2013 | Burkly |
| 2013/0095109 A1 | 4/2013 | Nadler et al. |
| 2014/0099317 A1 | 4/2014 | Suri et al. |
| 2014/0220031 A1 | 8/2014 | Van Vlijmen et al. |
| 2014/0302016 A1 | 10/2014 | Burkly |
| 2015/0104450 A1 | 4/2015 | Minter et al. |

(Continued)

FOREIGN PATENT DOCUMENTS

| | | |
|---|---|---|
| CN | 1441675 | 9/2003 |
| WO | WO 95/006481 | 3/1995 |
| WO | WO 96/040246 | 12/1996 |

(Continued)

OTHER PUBLICATIONS

Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14:2784-2794(1995). (Year: 1995).*
D'Angelo et al., Many Routes to an Antibody Heavy-Chain CDR3: Necessary, Yet Insufficient, for Specific Binding (Frontiers in Immunology vol. 9, Article 395 Mar. 2018; doi:10.3389/fimmu.2018. 00395), (Year: 2018).*

(Continued)

*Primary Examiner* — Phillip Gambel
(74) *Attorney, Agent, or Firm* — Knobbe, Martens, Olson & Bear, LLP

(57) ABSTRACT

Anti-CD40L antibodies and antigen binding fragments thereof, compositions comprising the antibodies or antigen binding fragments, Anti-CD40L antibodies with reduced effector function, and method of using same for treatment of CD40L-related diseases or disorders.

10 Claims, 23 Drawing Sheets

Specification includes a Sequence Listing.

(56) References Cited

U.S. PATENT DOCUMENTS

| | | | |
|---|---|---|---|
| 2016/0075790 | A1 | 3/2016 | Nadler et al. |
| 2017/0166655 | A1 | 6/2017 | Lazar et al. |

FOREIGN PATENT DOCUMENTS

| | | |
|---|---|---|
| WO | 1998052606 A1 | 11/1998 |
| WO | WO 99/051258 | 10/1999 |
| WO | WO 01/083755 | 11/2001 |
| WO | 2002004021 A1 | 1/2002 |
| WO | 2002018445 A2 | 3/2002 |
| WO | WO 04/037204 | 5/2004 |
| WO | 2005003175 A2 | 1/2005 |
| WO | WO 05/003174 | 1/2005 |
| WO | 2005011376 A2 | 2/2005 |
| WO | 2006029879 A2 | 3/2006 |
| WO | WO 06/138316 | 12/2006 |
| WO | 2007059332 A2 | 5/2007 |
| WO | WO 07/076354 | 7/2007 |
| WO | 2008118356 A2 | 10/2008 |
| WO | 2008143954 A2 | 11/2008 |
| WO | 2010023482 A2 | 3/2010 |
| WO | WO 10/065819 | 6/2010 |
| WO | 2010085682 A2 | 7/2010 |
| WO | WO 12/103218 | 8/2012 |
| WO | 2012138768 A2 | 10/2012 |
| WO | WO 13/033008 | 3/2013 |
| WO | WO 13/056068 | 4/2013 |
| WO | WO 14/163101 | 10/2014 |
| WO | 2015143209 A1 | 9/2015 |
| WO | WO 14/132101 | 10/2015 |
| WO | WO 15/164595 | 10/2015 |
| WO | 2016028810 A1 | 2/2016 |
| WO | 2016126702 A1 | 8/2016 |

OTHER PUBLICATIONS

Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/10.1080/19420862.2017.1389355. (Year: 2018).*

Jefferis, Nature Reviews / Drug Discovery 8: 226-234, Mar. 2009. (Year: 2009).*

Kiyoshi et al., Scientific Reports (2018) 8:3955 pp. 1-11, DOI:10.1038/s41598-018-22199-8, Assessing the Heterogeneity of the Fc-Glycan of a Therapeutic Antibody Using an Engineered FcγReceptor IIIa-Immobilized Column. (Year: 2018).*

Wang et al., Protein Cell 9: 63-73, 2018; DOI 10.1007/s13238-017-473-8. (Year: 2018).*

Saunders et al., Conceptual Approaches to Modulating Antibody Effector Functions and Circulating Half-Life (Frontiers in Immunology 10:1-20, 2019; doi: 10.3389/fimmu.2019.01296. (Year: 2019).*

Baker et al., "Identification and Removal of immunogenicity in Therapeutic Proteins," Current Opinion in Drug Discovery & Development, 2007, vol. 10, No. 2, pp. 219-227.

Daley et al., "Fc-Disabled Anti-Mouse CD40L Antibodies Retain Efficacy in Promoting Transplantation Tolerance," Am J Transplantation, 2008, vol. 8, pp. 2265-2271.

Davis et al., "Abatacept binds to the Fc receptor CD64 but does not mediate complement-dependent cytotoxicity or antibody-dependent cellular cytotoxicity," J. Rheumatol., 2007, vol. 34, No. 11, pp 2204-2210.

Holgate et al., "Circumventing Immunogenicity in the Development of Therapeutic Antibodies," Idrugs, 2009, vol. 12, No. 4, pp. 233-237.

Karpusas et al., "Structure of CD40 Ligand in Complex with the Fab Fragment of a Neutralizing Humanized Antibody," Structure, 2001, vol. 9, No. 4, pp. 321-329.

Ke et al., "CD40-CD40L interactions promote neuronal death in a model of neurodegeneration due to mild impairment of oxidative metabolism", Neurochemistry International, 2005, pp. 204-215, vol. 47, No. 3.

Kiaei et al., "Celastrol blocks neuronal cell death and extends life in transgenic mouse model of amyotrophic lateral sclerosis," Neurodegenerative Diseases, 2005, pp. 246-254, vol. 2, No. 5.

Lederman et al., Identification of a Novel Surface Protein on Activated CD4+ T Cells that Induces Contact-dependent B Cell Differentiation (Help), J Exp Med, 1992, vol. 175, pp. 1091-1101.

Linsley et al., "CTLA-4 is a Second Receptor for the B Cell Activation Antigen 87," J. Exp. Med., 1991, vol. 174, No. 3, pp. 561-569.

Okuno et al., "Induction of cyclooxygenase-2 in reactive glial cells by the CD40 pathway: relevance to amyotrophic Tateral sclerosis," Journal of Neurochemistry, 2004, vol. 91, No. 2, pp. 404-412.

Tai et al., "Mechanisms by Which SGN-40, a Humanized Anti-CD40 Antibody, Induces Cytotoxicity in Human Multiple Myeloma Cells: Clinical Implications", Cancer Rersearch, 2004, vol. 64, pp. 2846-2852.

Viglietta et al., "CTLA4lg Treatment in Patients With Multiple Sclerosis", Neurology, 2008, vol. 71, No. 12, pp. 917-924.

Xie et al., "Engineering of a Novel Anti-CD40L Domain Antibody for Treatment of Autoimmune Diseases," J. Immunol., 2014, vol. vol. 192, No. 9, pp. 4083-4092.

Sakoda S., "Study on a breakthrough technique to diagnosis or treat amyotrophic lateral sclerosis—analysis of CD40 in amyotrophic lateral sclerosis-," Report of 2006 Houkatsu Kenkyuu, 2007, pp. 51-53. (English Translation).

International Search Report and Written Opinion for PCT/US2018/034172, dated Dec. 17, 2018, 25 pages.

Abcam, "Anti-GAL4 antibody [5CB], " 2012, 2 pages.

Bosco et al,, "Wild-type and mutant SOD1 share an aberrant Conformation and a common pathogenic pathway in ALS", Nat. Neurosci., 2010, vol, 13, No. 11, pp. 1396-1403.

Building a Better Mouse, MDA/ALS Newsmagazine, Sep. 1, 2010.

Cicchetti et al., 2009, Environmental toxins and Parkinson's disease: what have we learned from pesticide-induced animal models, Trends in Pharmacological Sciences 30:475-483

Drachman et al., 1994, Trail of immunosuppression in amyotrophic lateral sclerosis neuro—using total lymphoid irradiation, Annals of Neurology, 35(2).

Dumont et al., "IDEC-1. IDEC/Eisai," Curr Opin Inventing Drugs, 2002, pp. 725-734, vol. 3, No. 5.

Gilliland "Rapid and Reliable Cloning of Antibody Variable Regions and Generation of Recombinant Single Chain Antibody Fragments", Tissue Antigens, 1996, vol. 47, pp. 1-20.

Gruzman et al., "Common Molecular Signature in SOD1 for both Sporadic and Familial Amyotrophic Lateral Sclerosis", PNAS, 2007, vol. 104, No. 30, pp. 12524-12529.

Imgenex, Monoclonal Antibody to IGF-1R (Clone 24-31), accessed Sep. 21, 2012, 2 pgs.

Kallmeier et al., "Poster—Improvements to the GS System for Easier Re-expression of Human Antibodies," 1 page.

Kirk et al., "CTLA4-10 and anti-CD4O Ligand Prevent Renal Allograft Rejection in Primates", Proc Natl Acad Sci Neuro—USA, 1997, vol. 94, pp. 8789-8794.

Knosalla et al., "Initial experience with the human anti-human CD154 monoclonal antibody, ANI793, in pig-to-baboon xenotransplantation", Xenotransplantation, 2004, pp. 353-360, vol. 11, No. 4.

Law et al., "Preclinical Antilymphorna Activity of a Human Anti-CD40 Monoclonal Antibody, SGN-40", Cancer Res, 2005, vol. 65, No. 18, pp. 8331-88338

Leitner et al., Working with ALS Mice:, The Jackson Laboratory, Oct. 14, 2009.

Lincecum et al,, "From Transcriptome Analysis to Therapeutic anti-CD40L Treatment in the SOD1 Model of Amyotrophic Lateral Sclerosis", Nature Genetics, 2010, pp. 1-10.

Ludolph et al., "Guidelines for Preclinical Animal Research in ALS/MND: A Consensus Meeting," Amyotrophic Lateral Sclerosis, 2010, vol, 11, pp. 38-45.

Madsen A., Building a Better Mouse: How Animal Models Help Fight ALS, MDA/ALS Newsmagazine, Sep. 1, 2010, vol, 15, No. 5, 4 pages.

National Institute of Neurological Disorders and Stroke (HINDS), "Amyotrophic Lateral Sclerosis (ALS) Fact Sheet", NIH Internet Publication relating to ALS accessed Nov. 19, 2012, 8 pp.

(56) References Cited

OTHER PUBLICATIONS

Santa Cruz Biotechnology Inc., accessed Sep, 21, 2012, 1 pg.
Seattle Genetics Receives Key U.S. Patents for SGN-40 Program, Jan. 19, 2005, http://www.seattlegenetics.com/, Posted by MMSupport.net, http://www.mmsupport.net/seattle-genetics-receives-key-Neuro-US-patents-for-sgn-40-program/, 3 pages.
Starzl et al., "Refinements in the Surgical Technique of Liver Transplantation," Semin Liver Dis., 1985, vol. 5, No. 4, pp. 349-356.
Traynor et al., "Neuroprotective agents for clinical trials in ALS: A systematic assessment," Neurology, 2006, vol. 67, pp. 20-27.
Vainzof et al., "Animal Models for Genetic Neuromuscular Diseases," J. Mol, Neurosci., 2008, pp. 241-248, vol. 34.
Van Blitterswijk et al., "Anti-superoxide Dismutase Antibodies are Associated with Survival in Patients with Sporadic Amyotrophic Lateral Sclerosis", Amyotroph Lateral Scler, 2011, vol. 12, No. 6, pp. 430-438.

\* cited by examiner

FcγRIIa Set 1

FcγRIIa Set 2

SEQUENCE LISTING

<160> NUMBER OF SEQ ID NOS: 57

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Arg Asn Asp Met Asp Ser Trp Gly Gln Gly Thr
            100                 105                 110

Leu Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Ser Asn Gly Asp Thr Asn Tyr Ala Glu Lys Phe
    50                  55                  60

Lys Gly Arg Ala Thr Leu Thr Val Asp Thr Ser Thr Ser Thr Val Tyr
65                  70                  75                  80
```

```
Met Glu Leu Ser Ser Leu Arg Ser Glu Asp Thr Ala Val Tyr Tyr Cys
            85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Ser Asn Gly Asp Thr Asn Phe Ala Glu Lys Phe
    50                  55                  60

Lys Gly Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: Synthetic

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Thr Tyr Ser Tyr Met His Trp Tyr Gln Gln Lys Pro Gly Gln Ala Pro
        35                  40                  45

Arg Leu Leu Ile Tyr Asp Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
            85                  90                  95

Glu Ile Pro Pro Thr Phe Gly Gln Gly Thr Lys Leu Glu Ile Lys
            100                 105                 110

<210> SEQ ID NO 6
<211> LENGTH: 111
<212> TYPE: PRT
```

<213> ORGANISM: Artificial Sequence
<220> FEATURE:
<223> OTHER INFORMATION: Synthetic

<400> SEQUENCE: 6

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asp Glu Arg Val Ser Ser Ser
            20                  25                  30

Thr Tyr Ser Tyr Met His Trp Tyr Gln Gln Lys Pro Gly Gln Ala Pro
        35                  40                  45

Arg Leu Leu Ile Tyr Asp Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gln Gly Thr Lys Leu Glu Ile Lys
            100                 105                 110
```

<210> SEQ ID NO 7
<211> LENGTH: 111
<212> TYPE: PRT
<213> ORGANISM: Artificial Sequence
<220> FEATURE:
<223> OTHER INFORMATION: Synthetic

<400> SEQUENCE: 7

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Thr Tyr Ser Tyr Met His Trp Tyr Gln Gln Lys Pro Gly Gln Ala Pro
        35                  40                  45

Arg Leu Leu Ile Lys Tyr Ala Ser Asn Arg Glu Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gln Gly Thr Lys Leu Glu Ile Lys
            100                 105                 110
```

<210> SEQ ID NO 8
<211> LENGTH: 111
<212> TYPE: PRT
<213> ORGANISM: Artificial Sequence
<220> FEATURE:
<223> OTHER INFORMATION: Synthetic

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asp Glu Arg Val Ser Ser Ser
            20                  25                  30

Thr Tyr Ser Tyr Met His Trp Tyr Gln Gln Lys Pro Gly Gln Ala Pro
        35                  40                  45

Arg Leu Leu Ile Lys Tyr Ala Ser Asn Arg Glu Thr Gly Ile Pro Ala
    50                  55                  60
```

```
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Trp
                 85                  90                  95

Glu Ile Pro Pro Thr Phe Gly Gln Gly Thr Lys Leu Glu Ile Lys
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Ser Tyr Tyr Met Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Glu Ile Asn Pro Ser Asn Gly Asp Thr Asn Tyr Ala Gln Lys Phe Gln
1               5                   10                  15

Gly

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Glu Ile Asn Pro Ser Asn Gly Asp Thr Asn Tyr Ala Glu Lys Phe Lys
1               5                   10                  15

Gly Arg Val

<210> SEQ ID NO 12
<211> LENGTH: 19
<212> TYPE: PRT
<213> ORGANISM: Artificial Sequence
<220> FEATURE:
<223> OTHER INFORMATION: Synthetic

<400> SEQUENCE: 12

Glu Ile Asn Pro Ser Asn Gly Asp Thr Asn Tyr Ala Glu Lys Phe Lys
1               5                   10                  15

Gly Arg Ala

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Glu Ile Asn Pro Ser Asn Gly Asp Thr Asn Phe Ala Glu Lys Phe Lys
```

```
<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Glu Ile Asn Pro Ser Asn Gly Asp Thr Asn Tyr Ala Glu Lys Phe Lys
1               5                   10                  15
Gly

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ser Asp Gly Arg Asn Asp Met Asp Ser
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Arg Ala Ser Gln Arg Val Ser Ser Ser Thr Tyr Ser Tyr Met His
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Arg Ala Asp Glu Arg Val Ser Ser Ser Thr Tyr Ser Tyr Met His
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Asp Ala Ser Asn Arg Ala Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic
```

<400> SEQUENCE: 19

Tyr Ala Ser Asn Arg Glu Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Gln His Ser Trp Glu Ile Pro Pro Thr
1               5

<210> SEQ ID NO 21
<211> LENGTH: 232
<212> TYPE: PRT
<213> ORGANISM: Artificial Sequence
<220> FEATURE:
<223> OTHER INFORMATION: Synthetic

<400> SEQUENCE: 21

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 22
<211> LENGTH: 329
<212> TYPE: PRT
<213> ORGANISM: Artificial Sequence
<220> FEATURE:

<223> OTHER INFORMATION: Synthetic

<400> SEQUENCE: 22

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 23
<211> LENGTH: 329
<212> TYPE: PRT
<213> ORGANISM: Artificial Sequence
<220> FEATURE:
<223> OTHER INFORMATION: Synthetic

<400> SEQUENCE: 23

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Ser Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Lys Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 24
<211> LENGTH: 326
<212> TYPE: PRT
<213> ORGANISM: Artificial Sequence
<220> FEATURE:
<223> OTHER INFORMATION: Synthetic

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Lys Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 25
<211> LENGTH: 107
<212> TYPE: PRT
<213> ORGANISM: Artificial Sequence
<220> FEATURE:
<223> OTHER INFORMATION: Synthetic

<400> SEQUENCE: 25

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 26
<211> LENGTH: 354
<212> TYPE: DNA
<213> ORGANISM: Artificial Sequence
<220> FEATURE:
<223> OTHER INFORMATION: Synthetic

<400> SEQUENCE: 26
gaggtgcagc tggtgcagtc cggcgccgag gtgaagaagc ccggcgcctc cgtgaaggtg    60
tcctgcaagg cctccggcta caccttcacc tcctactaca tgtactgggt gaggcaggcc   120
cccggccagg gcctggagtg gatgggcgag atcaacccct ccaacggcga caccaactac   180
gcacagaagt tccagggtag ggtcaccatg accgtggaca cgtccacctc caccgtctac   240
atggagctgt cctccctgag gtccgaggac accgccgtgt actactgcgc caggtccgac   300
ggcaggaacg acatggactc ctggggccag ggcacccctgg tgaccgtgtc ctcc         354

<210> SEQ ID NO 27
<211> LENGTH: 354
<212> TYPE: DNA
<213> ORGANISM: Artificial Sequence
<220> FEATURE:
<223> OTHER INFORMATION: Synthetic

<400> SEQUENCE: 27
gaggtgcagc tggtgcagtc cggcgccgag gtgaagaagc ccggcgcctc cgtgaaggtg    60
tcctgcaagg cctccggcta catcttcacc tcctactaca tgtactgggt gaggcaggcc   120
cccggccagg gcctggagtg gatgggcgag atcaacccct ccaacggcga caccaactac   180
gcagagaagt tcaagggtag ggtcaccatg accgtggaca cgtccacctc caccgtctac   240
atggagctgt cctccctgag gtccgaggac accgccgtgt actactgcac caggtccgac   300
ggcaggaacg acatggactc ctggggccag ggcacccctgg tgaccgtgtc ctcc         354

<210> SEQ ID NO 28
<211> LENGTH: 354
<212> TYPE: DNA
<213> ORGANISM: Artificial Sequence
<220> FEATURE:
<223> OTHER INFORMATION: Synthetic

<400> SEQUENCE: 28
gaggtgcagc tggtgcagtc cggcgccgag gtgaagaagc ccggcgcctc cgtgaaggtg    60
tcctgcaagg cctccggcta catcttcacc tcctactaca tgtactgggt gaggcaggcc   120
cccggccagg gcctggagtg gatcggcgag atcaacccct ccaacggcga caccaactac   180
gcagagaagt tcaagggtag ggccaccctg accgtggaca cgtccacctc caccgtctac   240
atggagctgt cctccctgag gtccgaggac accgccgtgt actactgcac caggtccgac   300
ggcaggaacg acatggactc ctggggccag ggcacccctgg tgaccgtgtc ctcc         354

<210> SEQ ID NO 29
<211> LENGTH: 354
<212> TYPE: DNA
<213> ORGANISM: Artificial Sequence
<220> FEATURE:

<223> OTHER INFORMATION: Synthetic

<400> SEQUENCE: 29

```
caggtgcagc tggtgcagtc cggcgccgag gtgaagaagc ccggcgcctc cgtgaaggtg    60
tcctgcaagg cctccggcta catcttcacc tcctactaca tgtactgggt gaggcaggcc   120
cccggccagg gcctggagtg gatcggcgag atcaaccccc caacggcga caccaacttc   180
gcagagaagt tcaagggtag ggccacccctg accgtggaca cgtccacctc caccgtctac   240
atggagctgt cctccctgag gtccgaggac accgccgtgt actactgcac caggtccgac   300
ggcaggaacg acatggactc ctggggccag ggcaccctgg tgaccgtgtc ctcc          354
```

<210> SEQ ID NO 30
<211> LENGTH: 333
<212> TYPE: DNA
<213> ORGANISM: Artificial Sequence
<220> FEATURE:
<223> OTHER INFORMATION: Synthetic

<400> SEQUENCE: 30

```
gagatcgtgc tgacccagtc acctgccacc ctgtccctgt cacctggaga gagagccacc    60
ctctcctgca gagcctccca gagggtgtcc tcctccacct actcctacat gcactggtac   120
cagcagaagc ctggacaggc acctaggctg ctgatctacg acgcctccaa cagggcgacc   180
ggtataccag ccaggttctc aggctcaggc tcaggcaccg acttcaccct gaccatctcc   240
tccctggagc cagaggactt cgccgtctac tactgccagc actcctggga gatcccacct   300
accttcggac aaggcaccaa gctggaaatc aaa                                333
```

<210> SEQ ID NO 31
<211> LENGTH: 333
<212> TYPE: DNA
<213> ORGANISM: Artificial Sequence
<220> FEATURE:
<223> OTHER INFORMATION: Synthetic

<400> SEQUENCE: 31

```
gagatcgtgc tgacccagtc acctgccacc ctgtccctgt cacctggaga gagagccacc    60
ctctcctgca gagccgatga gagggtgtcc tcctccacct actcctacat gcactggtac   120
cagcagaagc ctggacaggc acctaggctg ctgatctacg acgcctccaa cagggcgacc   180
ggtataccag ccaggttctc aggctcaggc tcaggcaccg acttcaccct gaccatctcc   240
tccctggagc cagaggactt cgccgtctac tactgccagc actcctggga gatcccacct   300
accttcggac aaggcaccaa gctggaaatc aaa                                333
```

<210> SEQ ID NO 32
<211> LENGTH: 333
<212> TYPE: DNA
<213> ORGANISM: Artificial Sequence
<220> FEATURE:
<223> OTHER INFORMATION: Synthetic

<400> SEQUENCE: 32

```
gagatcgtgc tgacccagtc acctgccacc ctgtccctgt cacctggaga gagagccacc    60
ctctcctgca gagcctccca gagggtgtcc tcctccacct actcctacat gcactggtac   120
cagcagaagc ctggacaggc acctaggctg ctgatcaagt acgcctccaa cagggagacc   180
ggtataccag ccaggttctc aggctcaggc tcaggcaccg acttcaccct gaccatctcc   240
tccctggagc cagaggactt cgccgtctac tactgccagc actcctggga gatcccacct   300
```
accttcggac aaggcaccaa gctggaaatc aaa         333

<210> SEQ ID NO 33
<211> LENGTH: 333
<212> TYPE: DNA
<213> ORGANISM: Artificial Sequence
<220> FEATURE:
<223> OTHER INFORMATION: Synthetic

<400> SEQUENCE: 33
gagatcgtgc tgacccagtc acctgccacc ctgtccctgt cacctggaga gagagccacc    60
ctctcctgca gagccgatga gagggtgtcc tcctccacct actcctacat gcactggtac   120
cagcagaagc tggacaggc acctaggctg ctgatcaagt acgcctccaa cagggagacc   180
ggtataccag ccaggttctc aggctcaggc tcaggcaccg acttcaccct gaccatctcc   240
tccctggagc cagaggactt cgccgtctac tactgccagc actcctggga gatcccacct   300
accttcggac aaggcaccaa gctggaaatc aaa                                333

<210> SEQ ID NO 34
<211> LENGTH: 374
<212> TYPE: PRT
<213> ORGANISM: Artificial Sequence
<220> FEATURE:
<223> OTHER INFORMATION: Synthetic

<400> SEQUENCE: 34

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

```
Thr Ser Ser Glu Tyr Gln Ile Leu Thr Ala Arg Arg Glu Asp Ser Gly
            245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
            290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
            325                 330                 335

Val Ile Ser Ser Leu Gln Glu Asp Arg His Leu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
    370

<210> SEQ ID NO 35
<211> LENGTH: 316
<212> TYPE: PRT
<213> ORGANISM: Artificial Sequence
<220> FEATURE:
<223> OTHER INFORMATION: Synthetic

<400> SEQUENCE: 35

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
            35                  40                  45

Ile Asn Val Leu Gln Glu Asp Ser Val Thr Leu Thr Cys Gln Gly Ala
        50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
            85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
            115                 120                 125

His Leu Glu Phe Gln Glu Gly Glu Thr Ile Met Leu Arg Cys His Ser
            130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
            165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
            195                 200                 205

Met Gly Ser Ser Ser Pro Met Gly Val Ile Val Ala Val Val Ile Ala
            210                 215                 220
```

```
Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Lys Asn Ile Tyr Leu
290                 295                 300

Thr Leu Pro Pro Asn Asp His Val Asn Ser Asn Asn
305                 310                 315

<210> SEQ ID NO 36
<211> LENGTH: 290
<212> TYPE: PRT
<213> ORGANISM: Artificial Sequence
<220> FEATURE:
<223> OTHER INFORMATION: Synthetic

<400> SEQUENCE: 36

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Leu Pro Thr Ala Leu Leu Leu
        35                  40                  45

Leu Val Ser Ala Gly Met Arg Thr Glu Asp Leu Pro Lys Ala Val Val
50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Ser Leu Ile Ser Ser Gln Ala Ser Ser Tyr Phe Ile
            100                 105                 110

Asp Ala Ala Thr Val Asp Asp Ser Gly Glu Tyr Arg Cys Gln Thr Asn
        115                 120                 125

Leu Ser Thr Leu Ser Asp Pro Val Gln Leu Glu Val His Ile Gly Trp
130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Leu Val Gly Ser Lys Asn Val Ser Ser Glu Thr Val Asn Ile
210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270
```

```
Thr Arg Asp Trp Lys Asp His Lys Phe Lys Trp Arg Lys Asp Pro Gln
        275                 280                 285
Asp Lys
    290

<210> SEQ ID NO 37
<211> LENGTH: 233
<212> TYPE: PRT
<213> ORGANISM: Artificial Sequence
<220> FEATURE:
<223> OTHER INFORMATION: Synthetic

<400> SEQUENCE: 37

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 38
<211> LENGTH: 218
<212> TYPE: PRT
<213> ORGANISM: Artificial Sequence
<220> FEATURE:
<223> OTHER INFORMATION: Synthetic

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Thr Tyr Ser Tyr Met His Trp Tyr Gln Gln Lys Pro Gly Gln Ala Pro
```

```
            35                  40                  45
Arg Leu Leu Ile Tyr Asp Ala Ser Asn Arg Ala Thr Gly Ile Pro Ala
 50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Trp
                85                  90                  95
Glu Ile Pro Pro Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 39
<211> LENGTH: 218
<212> TYPE: PRT
<213> ORGANISM: Artificial Sequence
<220> FEATURE:
<223> OTHER INFORMATION: Synthetic

<400> SEQUENCE: 39

Glu Ile Val Leu Thr Gln Ser Pro Ala Thr Leu Ser Leu Ser Pro Gly
1               5                   10                  15
Glu Arg Ala Thr Leu Ser Cys Arg Ala Asp Glu Arg Val Ser Ser Ser
            20                  25                  30
Thr Tyr Ser Tyr Met His Trp Tyr Gln Gln Lys Pro Gly Gln Ala Pro
        35                  40                  45
Arg Leu Leu Ile Tyr Asp Ala Ser Asn Arg Ala Thr Gly Ile Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Trp
                85                  90                  95
Glu Ile Pro Pro Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
```

```
                 180                 185                 190
His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 40
<211> LENGTH: 218
<212> TYPE: PRT
<213> ORGANISM: Artificial Sequence
<220> FEATURE:
<223> OTHER INFORMATION: Synthetic

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Thr Tyr Ser Tyr Met His Trp Tyr Gln Gln Lys Pro Gly Gln Ala Pro
        35                  40                  45

Arg Leu Leu Ile Lys Tyr Ala Ser Asn Arg Glu Thr Gly Ile Pro Ala
65              55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 41
<211> LENGTH: 218
<212> TYPE: PRT
<213> ORGANISM: Artificial Sequence
<220> FEATURE:
<223> OTHER INFORMATION: Synthetic

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Asp Glu Arg Val Ser Ser Ser
            20                  25                  30

Thr Tyr Ser Tyr Met His Trp Tyr Gln Gln Lys Pro Gly Gln Ala Pro
        35                  40                  45
```

```
Arg Leu Leu Ile Lys Tyr Ala Ser Asn Arg Glu Thr Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Trp
                 85                  90                  95

Glu Ile Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 42
<211> LENGTH: 232
<212> TYPE: PRT
<213> ORGANISM: Artificial Sequence
<220> FEATURE:
<223> OTHER INFORMATION: Synthetic

<400> SEQUENCE: 42

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Gly Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 43
<211> LENGTH: 232
<212> TYPE: PRT
<213> ORGANISM: Artificial Sequence
<220> FEATURE:
<223> OTHER INFORMATION: Synthetic

<400> SEQUENCE: 43

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 44
<211> LENGTH: 232
<212> TYPE: PRT
<213> ORGANISM: Artificial Sequence
<220> FEATURE:
<223> OTHER INFORMATION: Synthetic

<400> SEQUENCE: 44

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Gly Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 45
<211> LENGTH: 232
<212> TYPE: PRT
<213> ORGANISM: Artificial Sequence
<220> FEATURE:
<223> OTHER INFORMATION: Synthetic

<400> SEQUENCE: 45

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Gly Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 46
<211> LENGTH: 447
<212> TYPE: PRT
<213> ORGANISM: Artificial Sequence
<220> FEATURE:
<223> OTHER INFORMATION: Synthetic

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 47
<211> LENGTH: 447
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Glu Lys Phe
50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

```
Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 48
<211> LENGTH: 447
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Ser Asn Gly Asp Thr Asn Tyr Ala Glu Lys Phe
    50                  55                  60

Lys Gly Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 49
<211> LENGTH: 447
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Ile
        35                  40                  45
```

Gly Glu Ile Asn Pro Ser Asn Gly Asp Thr Asn Phe Ala Glu Lys Phe
            50                  55                  60

Lys Gly Arg Ala Thr Leu Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Ala Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 50
<211> LENGTH: 447

<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Gln Lys Phe
50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Lys Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 51
<211> LENGTH: 447
<212> TYPE: PRT
<213> ORGANISM: Artificial Sequence
<220> FEATURE:
<223> OTHER INFORMATION: Synthetic

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Tyr Met Tyr Trp Val Arg Gln Ala Pro Gly Gln Gly Leu Glu Trp Met
            35                  40                  45

Gly Glu Ile Asn Pro Ser Asn Gly Asp Thr Asn Tyr Ala Glu Lys Phe
50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Lys Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 52
<211> LENGTH: 447
<212> TYPE: PRT
<213> ORGANISM: Artificial Sequence
<220> FEATURE:
<223> OTHER INFORMATION: Synthetic

<400> SEQUENCE: 52

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Ser Asn Gly Asp Thr Asn Tyr Ala Glu Lys Phe
50              55                  60

Lys Gly Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

```
His Thr Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Lys Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 53
<211> LENGTH: 447
<212> TYPE: PRT
<213> ORGANISM: Artificial Sequence
<220> FEATURE:
<223> OTHER INFORMATION: Synthetic

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Ile
        35                  40                  45

Gly Glu Ile Asn Pro Ser Asn Gly Asp Thr Asn Phe Ala Glu Lys Phe
    50                  55                  60

Lys Gly Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Lys Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 54
<211> LENGTH: 444
<212> TYPE: PRT
<213> ORGANISM: Artificial Sequence
<220> FEATURE:
<223> OTHER INFORMATION: Synthetic

<400> SEQUENCE: 54

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Gln Lys Phe
    50                  55                  60

-continued

```
Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Lys Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 55
<211> LENGTH: 444
<212> TYPE: PRT
<213> ORGANISM: Artificial Sequence
<220> FEATURE:
<223> OTHER INFORMATION: Synthetic

<400> SEQUENCE: 55

| | | | | | | | | | | | | | | |
|---|---|---|---|---|---|---|---|---|---|---|---|---|---|---|
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Asp Thr Asn Tyr Ala Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Lys Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln

```
                        405                 410                 415
Glu Gly Asn Val Phe Ser Cys Ser Val Met His Glu Ala Leu His Asn
                420                 425                 430

His Tyr Thr Gln Lys Ser Leu Ser Leu Ser Leu Gly
            435                 440

<210> SEQ ID NO 56
<211> LENGTH: 444
<212> TYPE: PRT
<213> ORGANISM: Artificial Sequence
<220> FEATURE:
<223> OTHER INFORMATION: Synthetic

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Tyr Met Tyr Trp Val Arg Gln Ala Pro Gly Gln Gly Leu Glu Trp Ile
            35                  40                  45

Gly Glu Ile Asn Pro Ser Asn Gly Asp Thr Asn Tyr Ala Glu Lys Phe
    50                  55                  60

Lys Gly Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Lys Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
```

```
                    325                 330                 335
Ala Lys Gly Gln Pro Arg Glu Pro Gln Val Tyr Thr Leu Pro Pro Ser
                340                 345                 350
Gln Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440

<210> SEQ ID NO 57
<211> LENGTH: 444
<212> TYPE: PRT
<213> ORGANISM: Artificial Sequence
<220> FEATURE:
<223> OTHER INFORMATION: Synthetic

<400> SEQUENCE: 57

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Thr Ser Tyr
            20                  25                  30
Tyr Met Tyr Trp Val Arg Gln Ala Pro Gly Gln Gly Leu Glu Trp Ile
        35                  40                  45
Gly Glu Ile Asn Pro Ser Asn Gly Asp Thr Asn Phe Ala Glu Lys Phe
    50                  55                  60
Lys Gly Arg Ala Thr Leu Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Thr Arg Ser Asp Gly Arg Asn Asp Met Asp Ser Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
```

-continued

```
                245                 250                 255
Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Lys Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440
```

THERAPEUTIC ANTI-CD40 LIGAND ANTIBODIES

CROSS REFERENCE TO RELATED APPLICATIONS

This application is a 35 U.S.C. § 371 United States National Phase Application of, and claims priority to PCT Application No. PCT/US2018/034172, filed May 23, 2018, which claims priority to U.S. Provisional Application No. 62/510,471, filed May 24, 2017. The entire contents of the aforementioned disclosures are incorporated by reference.

SEQUENCE LISTING

This application incorporates by reference in its entirety the sequence listing entitled "224823-454882 ST25.txt" created on Nov. 20, 2019, at 3:15 pm, that is 100 KB, and filed electronically herewith.

FIELD

Anti-CD40L antibodies, compositions comprising the antibodies, and method of using same for treatment of CD40L-related diseases or disorders.

BACKGROUND

The interaction of CD40 with its ligand CD40L plays a critical role in regulating immune responses. Binding of CD40L to CD40 triggers activation of the CD40 pathway which up-regulates costimulatory molecules such as CD80 and CD86. Blockade of the interaction between CD40 and CD40L by monoclonal antibodies has been shown to result in protection from autoimmunity and graft rejection in various preclinical models. Recently, in a mouse model of amyotrophic lateral sclerosis, an antibody directed to CD40L was shown to delay disease onset and prolong survival the onset of disease. (U.S. Pat. No. 8,435,514, hereby incorporated by reference). In early clinical studies, the humanized anti-CD40L antibody hu5c8 showed efficacy in patients with lupus and in patients with immune thrombocytopenic purpura. However, incidents of thromboembolism in the patients treated with hu5c8 halted further trials. Further in vitro and preclinical animal studies established that interaction of the Fc with the Fc receptor FcγRIIa caused platelet activation, and aggregation, that resulted in thromboembolic events. In addition, it has been reported that binding of the Fc to complement may reduce or prevent induction of immune tolerance. Various approaches have been taken to reduce or eliminate the interaction of the immunoglobulin Fc region with FcγRIIa, and/or to reduce or eliminate the interaction with complement, including introducing point mutation(s) in the Fc region to make anti-CD40L antibodies which lack Fc effector function. Other approaches use fragments of antibodies lacking the Fc region or antibodies that contain multiple amino acid substitutions in the Fc region. Although the anti-CD40L antibody, hu5c8, showed efficacy in human patients there is no anti-CD40L antibody on the market. Accordingly, there is a need for improved anti-CD40L antibodies for administration to humans that are efficacious and do not cause platelet activation or aggregation or bind to complement yet are stable and bind to CD40L.

SUMMARY

Novel antibody polypeptides and antigen binding fragments thereof, of the present invention provide such improved anti-CD40L antibodies. The following section only summarizes certain aspects of the present disclosure and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The present invention provides isolated, engineered, non-naturally occurring antibodies and antigen binding fragments thereof, that bind human CD40L and block the binding of CD40 to CD40L. The antibody and antigen binding fragments thereof, are engineered to have the desired activity and binding. In some embodiments the antibody or antigen binding fragment thereof, are engineered to have decreased Fc effector function in comparison to some previous anti-CD40L antibodies. The antibodies and antigen binding fragments thereof as disclosed in the present application are useful in the treatment of diseases involving CD40L activation, including neurodegenerative or neuromuscular diseases or disorders, inflammatory or immune diseases or disorders and autoimmune diseases.

In one aspect the present disclosure provides isolated antibodies or antigen-binding fragments thereof that specifically binds to CD40L which comprise: (a) a heavy chain variable region ($V_H$) comprising; i) a CDRH1 domain comprising the sequence set forth in SEQ ID NO: 9; ii) a CDRH2 domain comprising the sequence set forth in SEQ ID NO: 10, 11, 12, 13, or 14; iii) a CDRH3 domain comprising the sequence set forth in SEQ ID NO: 15; and (b) a light chain variable region ($V_L$) comprising: i) a CDRL1 domain comprising the sequence set forth in SEQ ID NO: 16 or 17; ii) a CDRL2 domain comprising the sequence set forth in SEQ ID NO: 18 or 19; and iii) a CDRL3 domain comprising the sequence set forth in SEQ ID NO: 20.

In some embodiments of the above aspect the present disclosure provides isolated antibodies or antigen-binding fragments thereof that specifically binds to CD40L which comprise: (a) a heavy chain variable region ($V_H$) comprising; i) a CDRH1 domain consisting of the sequence set forth in SEQ ID NO: 9; ii) a CDRH2 domain consisting of the sequence set forth in SEQ ID NO: 10, 11, 12, 13, or 14; iii) a CDRH3 domain consisting of the sequence set forth in SEQ ID NO: 15; and (b) a light chain variable region ($V_L$) comprising: i) a CDRL1 domain consisting of the sequence set forth in SEQ ID NO: 16 or 17; ii) a CDRL2 domain consisting of the sequence set forth in SEQ ID NO: 18 or 19; and iii) a CDRL3 domain consisting of the sequence set forth in SEQ ID NO: 20.

The present disclosure also provides for isolated antibodies or antigen-binding fragments thereof that specifically binds to CD40L comprising: (a) a heavy chain variable region ($V_H$) having the amino acid sequence as set forth in SEQ ID NOs: 1, 2, 3, or 4: and (b) a light chain variable region ($V_L$) having the amino acid sequence as set forth in SEQ ID NOs: 5, 6, 7, or 8.

In some embodiments the isolated antibody or antigen binding fragment thereof according to the disclosure comprises an Fc region and the Fc region has been engineered to reduce or eliminate one or more Fc effector function. In some embodiments the isolated antibodies are of the IgG1 isotype, and the heavy chain constant region comprises the amino acid sequence as set forth in SEQ ID NO: 21. In yet other embodiments the antibody comprises a heavy chain constant region wherein the heavy chain constant region comprises the amino acid sequence as set forth in SEQ ID NO: 22. In still other embodiments the antibody comprises a heavy chain constant region wherein the heavy chain constant region comprises the amino acid sequence as set forth in SEQ ID NO: 23. In another embodiment the antibody comprises a heavy chain constant region wherein the heavy chain constant region comprises the amino acid sequence as set forth in SEQ ID NO: 24.

Another aspect of the present disclosure provides for methods for treating a subject with a CD40L-associated disease or disorder comprising administering to the subject a therapeutically effective amount of an antibody or antibody fragment according to the present disclosure. In another aspect the present disclosure provides for methods for inhibiting an immune response in a subject comprising administering to the subject a therapeutically effective amount of an antibody or antibody fragment according to the present disclosure.

BRIEF DESCRIPTION OF THE DRAWING(S)

Figure 6A:
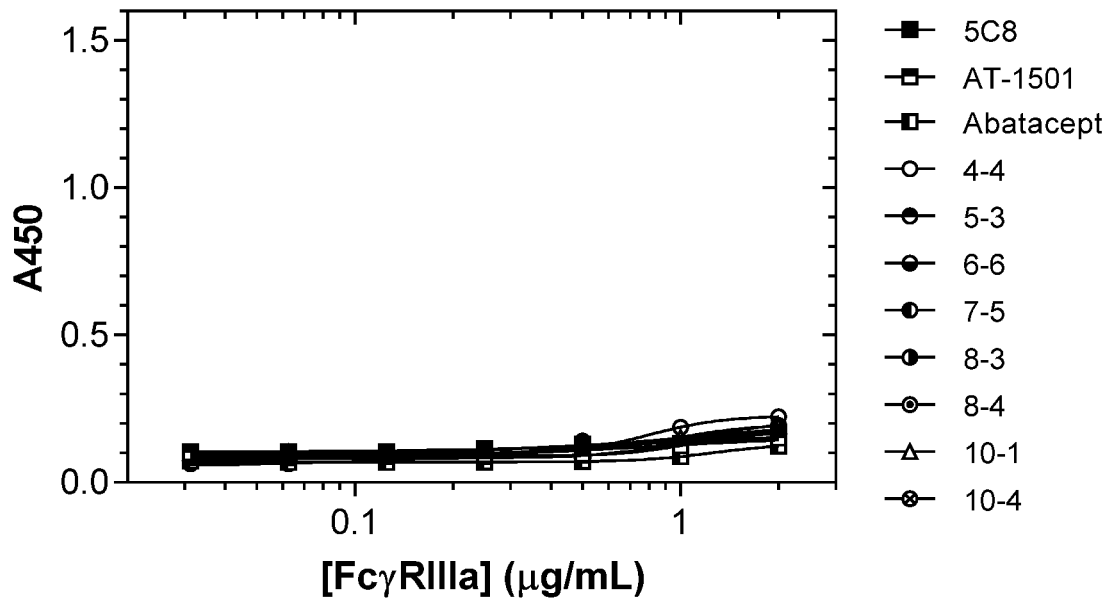
Figure 6B:
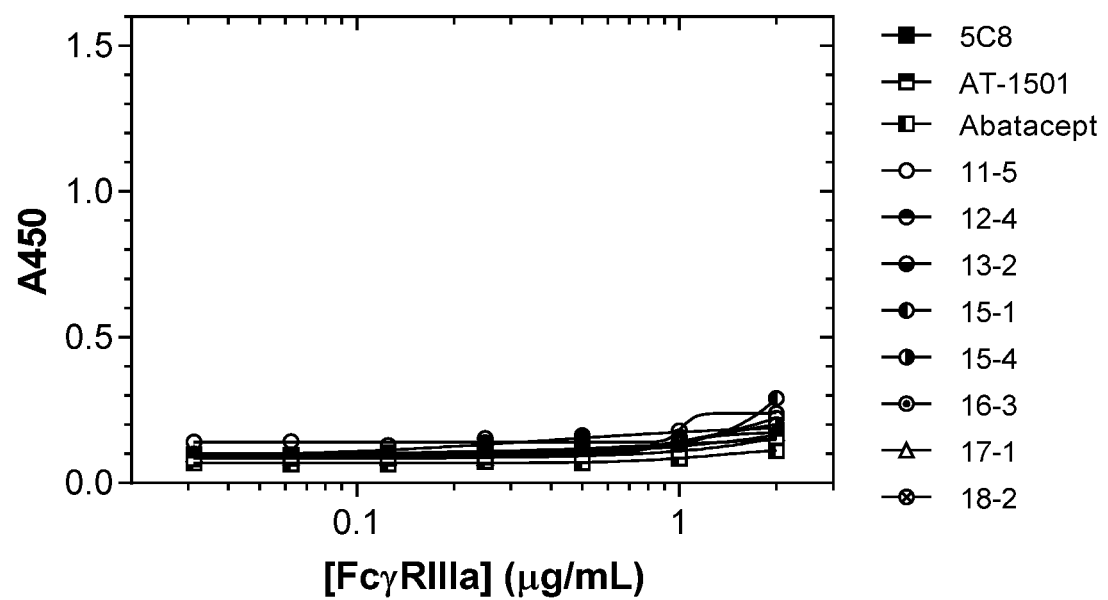
Figure 6C:
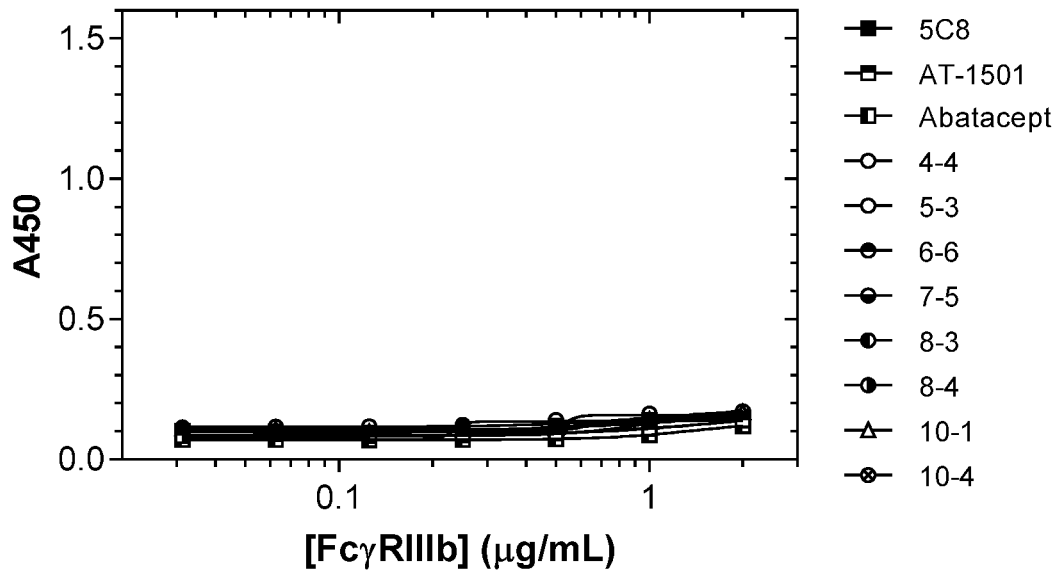
Figure 6D:
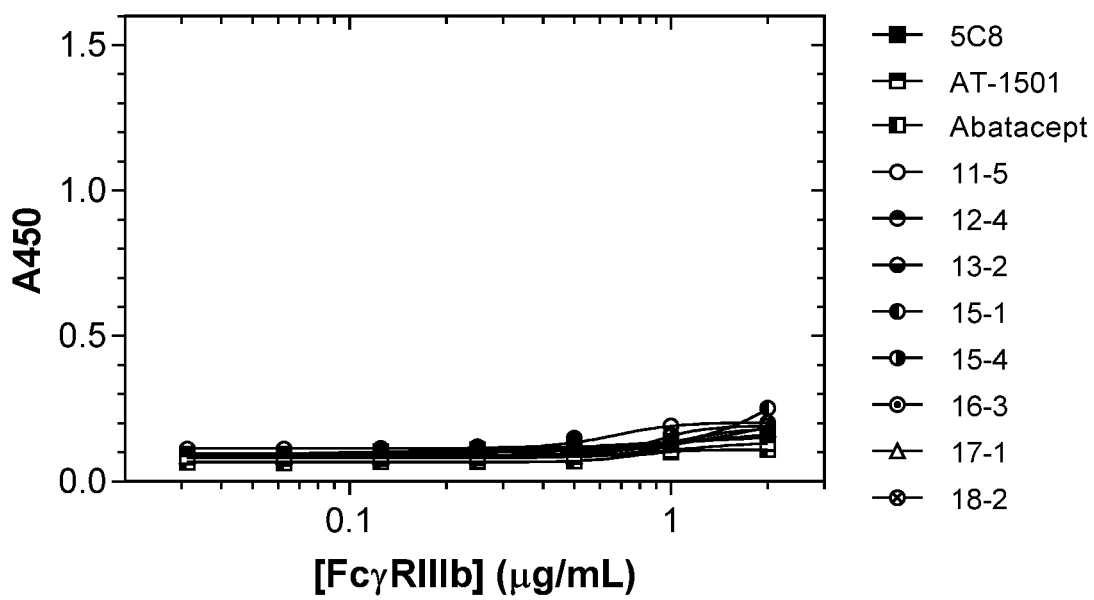

FIGS. 6A and 6B are graphs, each of which shows binding of eight of the antibody clones, 5c8, AT-1501 and abatacept to FcγRIIIa. None of the antibodies showed significant binding to FcγRIIIa. FIGS. 6C and 6D are graphs, each of which shows binding of eight of the antibody clones, 5c8, AT-1501 and abatacept to FcγRIIIb. None of the antibodies showed significant binding to FcγRIIIb.

Figure 7A:
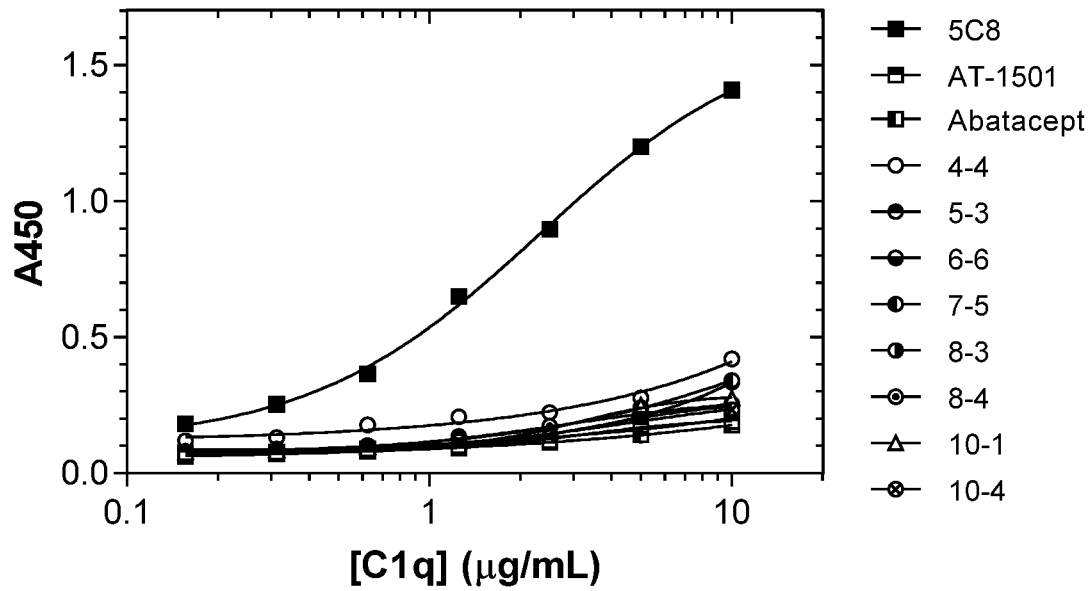
Figure 7B:
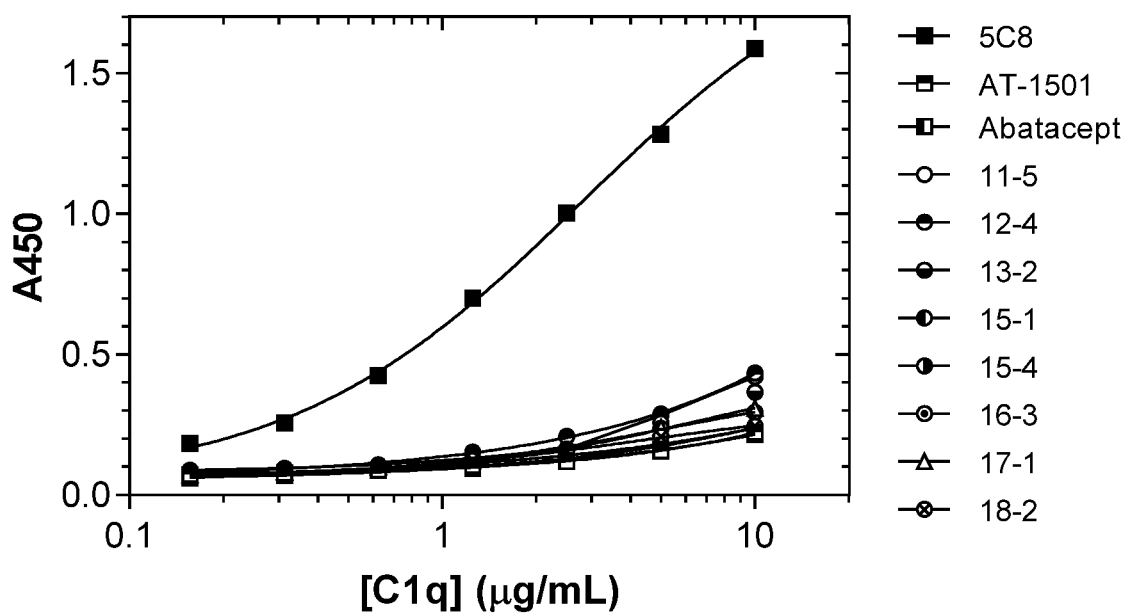

FIGS. 7A and 7B are graphs, each showing the binding of eight of the antibody clones, 5c8, AT-1501 and abatacept to C1q. The only antibody having significant binding to C1q was the 5c8 antibody.

DETAILED DESCRIPTION

Definitions

For convenience, the meaning of certain terms and phrases used in the specification, examples, and appended claims, are provided below.

The terms such as "comprises", "comprised", "comprising", "contains", "containing" and the like have the meaning attributed in United States patent law; these terms are inclusive or open-ended and do not exclude additional, unrecited elements or method steps. Terms such as "consisting essentially of" and "consists essentially of" have the meaning attributed to them in United States patent law; these terms allow for the inclusion of additional ingredients or steps that do not materially affect the basic and novel characteristics of the claim invention. The terms "consists of" and "consisting of" have the meaning ascribed to them in United States patent law; these terms are close ended.

TMB is an abbreviation of 3,3',5,5'-Tetramethylbenzidine.

"CDR domain" as used herein means an antibody complementary determining region with or without flanking sequences.

The invention illustratively described herein suitably may be practiced in the absence of any element or elements, limitation or limitations which is not specifically disclosed herein.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. One effector function is ability of the Fc or constant region of an antibody to bind proteins including, but not limited to, an Fc receptor (FcR) (e.g., high affinity Fc region of IgG receptor Ia (FcγRIa) (CD64) (SEQ ID NO: 34), low affinity immunoglobulin gamma Fc region acceptor IIa (FcγRIIa) (CD32) (SEQ ID NO: 35), low affinity immunoglobulin gamma Fc region receptor IIIa (FcγRIIIA) (CD16a) (SEQ ID NO: 36), low affinity immunoglobulin gamma Fc region receptor IIIb (FcγRIIIb) (CD16b)) (SEQ ID NO: 37). In embodiments of the present invention where the antibodies and antigen binding fragments thereof, have an Fc domain, the Fc domain has been engineered to reduce or eliminate one or more Fc effector function. In a preferred embodiment the Fc domain has been engineered to reduce or eliminate platelet activation and/or platelet aggregation and the concomitant risk of thromboembolism.

As used herein, the singular forms "a", "an", and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The use of the conjunction "or" is used interchangeably with at "least one of". For example: where a composition comprises A or B, the method must comprise at least one of A and B but may also comprise both A and B. Likewise a composition comprising "A, B, C or D" must comprise at least one of the group of A, B, C and D, but may also comprise all or any combination of A, B, C and D.

The term "about" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein encompasses variations of up to ±10% from the specified value. Unless otherwise indicated, all numbers expressing quantities of ingredients, properties such as molecular weight, reaction conditions, etc., used herein are to be understood as being modified by the term "about".

CD40L is also known as CD154, gp39, T-BAM, 5c8 antigen, or TNF related activation protein (TRAP).

The terms "treat," "treatment" and the like, include therapeutic treatment and prophylactic treatment. Therapeutic treatment is treatment of a subject that has signs or symptoms of the disease, condition or disorder to be treated.

Prophylactic treatments refers to treatment of a subject that is predisposed to the disease, condition or disorder that does not show overt signs of the disease, condition or disorder. Thus, treatment may result in stasis of, partial or total alleviation, or reduction of signs or symptoms of illness, and specifically includes, without limitation, prolongation of survival and cure.

An "effective amount" of an agent, e.g., a pharmaceutical formulation, refers to an amount effective, at dosages and for periods of time necessary, to achieve the desired therapeutic or prophylactic result.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the equilibrium dissociation constant (KD), a ratio of koff/kon, between the antibody and its antigen. KD and affinity are inversely related. The KD value relates to the concentration of antibody (the amount of antibody needed for a particular experiment) and so the lower the KD value (lower concentration) and thus the higher the affinity of the antibody. Affinity may be measured by common methods known in the art, including those described herein. Specific, illustrative, and exemplary embodiments for measuring binding affinity may be measured by radioimmunoassays (RIA), Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a human CD40 ligand polypeptide used as analyte. Other methods may include radioimmunoassays, and the Kinetic Exclusion Assay. The Kinetic Exclusion Assay is a general purpose immunoassay platform that is capable of measuring equilibrium dissociation constants, and association and dissociation rate constants for antigen/anti-body interactions.

Reference in the specification is made to percent identity between polypeptide or amino acid sequences. The percent identity between the two sequences is a function of the number of identical positions shared by the sequences, taking into account the number of gaps, and the length of each gap, which need to be introduced for optimal alignment of the two sequences. Identity can be measured as "local identity" or "global identity". Local identity refers the degree of sequence relatedness between polypeptides as determined by the match between strings of such sequences. Global identity refers to the degree of sequence relatedness of a polypeptide compared to the full-length of a reference polypeptide. Unless specified otherwise, as used herein, identity means global identity. For the purposes of this disclosure and claims, the percentages for global identity are calculated using Needleman and Wunsch ((1970) J. Mol. Biol. 48:444-453) algorithm using a Blossum 62 scoring matrix with a gap penalty of 12, a gap extend penalty of 4, and a frameshift gap penalty of 5. There are many publically available software programs that incorporate the Needleman and Wunsch algorithm, e.g. the GAP program in the GCG software package.

One of ordinary skill in the art will appreciate that starting materials, biological and chemical materials, biological and chemical reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this disclosure.

Amino acid substitutions are denoted by the convention in which the original amino acid, the position of the amino acid in the specified sequence and the replacement amino acid are identified, for example, C11S would indicate that the cysteine at position 11 of the polypeptide sequence is replaced with a serine.

Humanized antibodies are antibodies produced from non-human species whose protein sequences have been modified to increase their similarity to antibody variants produced naturally in humans. The process of "humanization" is usually applied to monoclonal antibodies developed for administration to humans (for example, antibodies developed as anti-cancer drugs).

Currently it is common to humanize a non-human antibody by insertion of relevant CDRs from antibodies created in a non-human animal into a human antibody "scaffold". "Direct" creation of a humanized antibody can be accomplished by inserting the appropriate CDR coding segments (responsible for the desired binding properties) into a human antibody "scaffold". This may be achieved through recombinant DNA methods using an appropriate vector and expression in mammalian cells. That is, after an antibody is developed to have the desired properties in a mouse (or other non-human), the DNA coding for that antibody can be isolated, cloned into a vector and sequenced. The DNA sequence corresponding to the antibody CDRs can then be determined. Once the precise sequence of the desired CDRs are known, a strategy can be devised for inserting these sequences appropriately into a construct containing the DNA for a human antibody variant. The CDRs may also be varied, e.g., to increase specificity, prior to insertion into the scaffold.

The term "human" antibody refers to an antibody which possesses an amino acid sequence which corresponds to that of an antibody produced by a human and/or has been made using any technique for making human antibodies. This definition of a human antibody specifically excludes a humanized antibody comprising non-human antigen binding residues.

An "antigen binding antibody fragment" refers to a molecule other than an intact antibody that comprises a portion of an intact antibody that binds the antigen to which the intact antibody binds. Examples of antibody fragments include but are not limited to Fv, Fab, Fab', Fd fragments, dAb fragments, Fab'-SH, F(ab')2; diabodies; triabodies; linear antibodies; single-chain antibody molecules (e.g., scFv); and multispecific antibodies formed from antibody fragments, minimal recognition units consisting of the amino acid residues that mimic the hypervariable region of an antibody (e.g., an isolated complementarity determining region (CDR) such as a CDR3 peptide). An antigen binding fragment as disclosed in the present application binds to the antigen CD40L.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

The isolated antibody includes bispecific antibodies in which each arm of the antibody or the antigen binding fragment binds to a different target or epitope.

The terms "full length antibody," "intact antibody," and "whole antibody" are used herein interchangeably to refer to an antibody having a structure substantially similar to a native antibody structure or having heavy chains that contain an Fc region.

"5c8" refers to the mouse anti-human antibody that binds CD40L and is produced by the hybridoma that is available from the ATCC having the accession number HB10916 and is described in U.S. Pat. No. 5,474,771. "hu5c8" refers to a humanized version of 5c8 the sequence of which is disclosed in Karpusas, et al., Structure vol. 9, pp 321-329, (2001).

The terms "subject" and "individual" and "patient" are used interchangeably herein, and refer to a human subject, individual or patient.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "may" and "may comprise" and their variants are intended to be non-limiting, such that recitation that an embodiment may or may comprise certain elements or features does not exclude other embodiments of the present technology that do not contain those elements or features The term "isolated protein" or "isolated polypeptide" (e.g., an isolated antibody or isolated antigen binding fragment) is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "variant" as used herein is defined as a modified or altered form of a wildtype sequence, e.g. where one or more amino acids may be replaced by other amino acid(s) or non-amino acid(s) which do not substantially affect function. In some embodiments, the variant may contain an altered side chain for at least one amino acid residue.

The term "antigen" as used herein is defined as an entity that can stimulate the production of antibodies and specifically combine with them and/or an entity which elicits an immune system response. For example, a cell surface protein or a specific linear or non-linear portion thereof. The term herein may be abbreviated to "Ag."

The term "specifically binds," or the like, means that an antibody or antigen-binding fragment thereof forms a complex with an antigen that is relatively stable under physiological conditions. Specific binding may be characterized by an equilibrium dissociation constant (KD) of about 3000 nM or less (i.e., a smaller KD denotes a tighter binding), about 2000 nM or less, about 1000 nM or less; about 500 nM or less; about 300 nM or less; about 200 nM or less; about 100 nM or less; about 50 nM or less; about 1 nM or less; or about 0.5 nM.

Specific binding for a particular antigen or an epitope may be exhibited, for example, by an antibody having a KD for an antigen or epitope of at least about $1\times10^{-4}$ M, at least about $1\times10^{-5}$ M, at least about $1\times10^{-6}$ M, at least about $1\times10^{-7}$ M, at least about $1\times10^{-M}$, at least about $1\times10^{-9}$ M, alternatively at least about $1\times10^{-10}$ M, at least about $1\times10^{-11}$ M, at least about $1\times10^{-12}$ M, or greater, where KD refers to a equilibrium dissociation constant of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope. Also, specific binding for a particular antigen or an epitope may be exhibited, for example, by an antibody having a Ka for an antigen or epitope of at least 20-, 50-, 100-, 500-, 1000-, 5,000-, 10,000- or more times greater for the epitope relative to a control, where Ka refers to an association rate of a particular antibody-antigen interaction.

The term "neutralizing antibody" includes an antibody that is capable of inhibiting and/or neutralizing the biological activity of CD40L, for example an anti-CD40L antibody or antigen fragment thereof that inhibits or prevents or diminishes the binding of CD40L to CD40, and thus inhibiting or reducing the signaling pathway triggered by CD40L and/or inhibiting or reducing the binding of CD40L to CD40.

The terms "antagonistic antibody" or "antagonist antibody" are used herein equivalently and include an antibody that is capable of inhibiting and/or neutralizing the biological signaling activity of CD40L, as described for a neutralizing antibody supra.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although aspects of the present invention have been specifically disclosed by various embodiments which may include preferred embodiments, exemplary embodiments and optional features, modifications and variations of the concepts herein disclosed may be resorted to by those skilled in the art. Such modifications and variations are considered to be within the scope of embodiments of the invention as described and as may be defined by the appended claims.

Pharmaceutical Compositions and Methods of Administration

Pharmaceutical compositions for use in accordance with the methods of the present disclosure may be formulated in a conventional manner using one or more physiologically acceptable carriers. Pharmaceutically acceptable carriers are determined in part by the particular composition being administered, as well as by the particular method used to administer the composition. Accordingly, there are a wide variety of suitable formulations of the compounds useful in the methods of the present disclosure (see, e.g., Remington: The Science and Practice of Pharmacy, 20th ed., Gennaro et al. Eds., Lippincott Williams and Wilkins, 2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Exemplary injection or infusion excipients may include mannitol, citric acid monohydrate, dibasic sodium phosphate dihydrate, monobasic sodium phosphate dihydrate, polysorbate 80, sodium chloride, sodium citrate and water.

According to the present disclosure the compounds can be administered by any suitable means, which can vary, depending on the type of disorder being treated and on the nature of the compound itself. For example, for the antibodies and antigen binding fragments thereof, of the present invention, administration routes preferably include parenteral, e.g., intramuscular, intravenous, intraarterial, intraperitoneal, intracerebrospinal, intraspinal, epidural, subcutaneous or by sustained release systems or an implant. Preferably, the parenteral dosing is given by injection, most preferably intravenous, intramuscular or subcutaneous injection.

In some embodiments, the anti-CD40L antibodies or antigen-binding fragments thereof of the present disclosure are formulated for and may be lyophilized for storage and reconstituted in a suitable excipient prior to use according to art-known lyophilization and reconstitution techniques.

In one exemplary pharmaceutical composition containing the anti-CD40L antibody or antigen-binding fragment thereof, the composition is formulated as a sterile, preservative-free solution of the anti-CD40L antibody or antigen-binding fragment thereof for intravenous or subcutaneous administration. The formulation may be supplied as either a single-use, prefilled pen, as a single-use, for example containing about 1 mL prefilled glass syringe, or as a single-use institutional use vial. Preferably, the pharmaceutical composition containing the anti-CD40L antibody or antigen-binding fragment thereof is clear and colorless, with a pH of about 5.0 to about 6.9, preferably a pH of about 5.0 to about 6.5, and even more preferably a pH ranging from about 5.0 to about 6.0. In various embodiments, the formulations comprising the pharmaceutical compositions may contain from about 500 mg to about 1 mg, or from about 400 mg to about 10 mg, or from about 300 mg to about 30 mg or from about 200 mg to about 50 mg of the anti-CD40L antibody or antigen-binding fragment thereof per mL of solution when reconstituted and administered to the subject.

Selecting an administration regimen for a therapeutic depends on several factors, including the serum or tissue turnover rate of the entity, the level of symptoms, the immunogenicity of the entity, and the accessibility of the target cells in the biological matrix, general health of the patient, the prior medical history of the patient, and the like. Preferably, an administration regimen maximizes the amount of therapeutic delivered to the patient consistent with an acceptable level of side effects. Accordingly, the amount of biologic delivered depends in part on the particular entity and the severity of the condition being treated. It should be appreciated that determination of proper dosage forms, dosage amounts, and routes of administration is within the level of ordinary skill in the pharmaceutical and medical arts.

Doses

The pharmaceutical formulations of the present disclosure may contain from about 0.001 to about 200 mg/kg of an anti-CD40L antibody or antigen binding fragment thereof, for example, from about 0.001 mg/kg to about 100 mg/kg, or from about 0.001 mg/kg to about 50 mg/kg, or from about 0.001 mg/kg to about 10 mg/kg intravenous injection of the anti-CD40L antibody, or antigen-binding fragment thereof, may be given as a bolus, and the rest of the antibody dose may be administered by intravenous injection. A predetermined dose of the anti-CD40L antibody, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the antibody formulation. In some exemplary doses, the antibody formulation may be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the anti-CD40L antibody, or antigen-binding fragment thereof. In some embodiments the dose may be given as a bolus, and the rest of the antibody dose may be administered by subcutaneous or intravenous injection. A predetermined dose of the anti-CD40L antibody, or antigen-binding fragment thereof, may be administered, for example, over a period of an hour, or a period of two hours, or a period of three hours, or a period of four hours or a period of five hours or longer.

Combination Therapies

The antibodies or antibody fragments thereof described herein can be administered alone (monotherapy) or in combination, i.e., combined with other agents. For example, in one embodiment the combination therapy may include one or more additional therapeutic agents. In another embodiment the combination therapy includes standard of care treatment that may, or may not, include additional therapeutic agents (consists essentially of the antibody or antibody fragment thereof).

Adjunctive or combined administration (co-administration) includes simultaneous administration of any of the antibodies or antigen binding fragments thereof, described herein and one or more agents in the same or different dosage form, or separate administration of the polypeptide and one or more agents (e.g., sequential administration). Such concurrent or sequential administration preferably results in both the polypeptide and the one or more agents being simultaneously present in treated patients.

Kits and Articles of Manufacture

Further provided are kits containing the antibody or antigen binding fragments thereof described herein and instructions for use. Kits typically include a packaged combination of reagents in predetermined amounts with instructions and a label indicating the intended use of the contents of the kit. The term label or instruction includes any writing, or recorded material supplied on or with the kit, or which otherwise accompanies the kit at any time during its manufacture, transport, sale or use. It can be in the form prescribed by a governmental agency regulating the manufacture, use or sale of pharmaceuticals or biological products, which notice reflects approval by the agency of the manufacture, use or sale for administration to a human or for veterinary use. The label or instruction can also encompass advertising leaflets and brochures, packaging materials, and audio or video instructions.

Embodiments

All embodiments of the isolated antibodies or antigen binding fragments thereof, bind to CD40L and inhibit or block the binding of CD40L to CD40. As used herein, "block the binding of CD40L and CD40" and "block the interaction between CD40L and CD40" are used interchangeably. Inhibiting or blocking the binding can be direct or indirect. Generally the antibody or antigen binding fragment thereof, will interfere physically with the binding of CD40L to CD40 via direct specific competition with CD40 for the same binding site on CD40L or via steric hindrance caused by binding of the antibody or antigen binding fragment thereof in proximity to the CD40-binding site of CD40L. In other instances the effect is indirect, for example the antibody or antigen binding fragment thereof cause an allosteric change in the conformation of CD40L which inhibits or eliminates its binding to CD40.

One embodiment is an isolated antibody that binds to CD40L and that comprises a light chain and a heavy chain, wherein the light chain comprises a light chain variable region comprises an amino acid sequence having at least 90%, or at least 91%, or at least 92%, or at least 93%, or at least 94%, or at least 95%, or at least 96% or at least 97%, or at least 98% or at least 99% sequence identity with SEQ ID NO: 5, SEQ ID NO: 6, SEQ ID NO: 7, or SEQ ID NO: 8, and the heavy chain comprises a variable heavy chain region wherein the heavy chain variable region comprises an amino acid sequence having at least 90%, or at least 91%, or at least 92%, or at least 93%, or at least 94%, or at least 95%, or at least 96%, or at least 97%, or at least 98%, or at least 99% sequence identity with SEQ ID NO:1, SEQ ID NO: 2, SEQ ID NO: 3, or SEQ ID NO: 4.

In one embodiment the present disclosure provides an isolated antibody or antigen-binding fragment thereof that specifically binds to CD40L comprising: a) a heavy chain variable region (VH) comprising; i) a CDRH1 domain comprising the sequence set forth in SEQ ID NO: 9; ii) a CDRH2 domain comprising the sequence set forth in SEQ ID NO: 10, 11, 12, 13, or 14; iii) a CDRH3 domain comprising the sequence set forth in SEQ ID NO: 15; and (b) a light chain variable region (VL) comprising: i) a CDRL1 domain comprising the sequence set forth in SEQ ID NO: 16 or 17; ii) a CDRL2 domain comprising the sequence set forth in SEQ ID NO: 18 or 19; iii) a CDRL3 domain comprising the sequence set forth in SEQ ID NO: 20.

In aspect A the present disclosure provides an isolated antibody or antigen-binding fragment thereof that specifically binds to CD40 L comprising: a) a heavy chain variable region (VH) comprising; i) a CDRH1 domain consisting of the sequence set forth in SEQ ID NO: 9; ii) a CDRH2 domain consisting of the sequence set forth in SEQ ID NO: 10, 11, 12, 13, or 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16 or 17; ii) a CDRL2 domain consisting of the sequence set forth in SEQ ID NO: 18 or 19; iii) a CDRL3 domain consisting of the sequence set forth in SEQ ID NO: 20.

One embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 10; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 10; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 11; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 11; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 19; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 19; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 12; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 12; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Still another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Still another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 13; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 13; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 16; ii) a CDRL2 domain comprising the sequence set forth in SEQ ID NO: 18; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 16; ii) a CDRL2 domain consisting of the sequence set forth in SEQ ID NO: 18; iii) a CDRL3 domain consisting of the sequence set forth in SEQ ID NO: 20.

Another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 18; iii) a CDRL3 domain comprising the sequence set forth in SEQ ID NO: 20. Another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 18; iii) a CDRL3 domain consisting of the sequence set forth in SEQ ID NO: 20.

Yet another embodiment of aspect A is an isolated antibody or antigen-binding fragment thereof, comprising: (a) a heavy chain variable region (VH) comprising; i) a CDRH1 domain comprising the sequence set forth in SEQ ID NO: 9; ii) a CDRH2 domain comprising the sequence set forth in SEQ ID NO: 14; iii) a CDRH3 domain comprising the sequence set forth in SEQ ID NO: 15; and (b) a light chain variable region (VL) comprising: i) a CDRL1 domain comprising the sequence set forth in SEQ ID NO: 17; ii) a CDRL2 domain comprising the sequence set forth in SEQ ID NO: 19; iii) a CDRL3 domain comprising the sequence set forth in SEQ ID NO: 20. Yet another embodiment of aspect A is an isolated antibody or antigen-binding fragment thereof, comprising: (a) a heavy chain variable region (VH) comprising; i) a CDRH1 domain consisting of the sequence set forth in SEQ ID NO: 9; ii) a CDRH2 domain consisting of the sequence set forth in SEQ ID NO: 14; iii) a CDRH3 domain consisting of the sequence set forth in SEQ ID NO: 15; and (b) a light chain variable region (VL) comprising: i) a CDRL1 domain consisting of the sequence set forth in SEQ ID NO: 17; ii) a CDRL2 domain consisting of the sequence set forth in SEQ ID NO: 19; iii) a CDRL3 domain consisting of the sequence set forth in SEQ ID NO: 20.

In aspect B the present disclosure provides isolated antibodies or an antigen-binding fragment thereof that specifically binds to CD40 L comprising: (a) a heavy chain variable region (VH) having the amino acid sequence as set forth in SEQ ID NOs: 1, 2, 3, or 4: and (b) a light chain variable region (VL) having the amino acid sequence as set forth in SEQ ID NOs: 5, 6, 7, or 8.

An embodiment of aspect B is an isolated antibody or antigen-binding fragment thereof comprising a heavy chain variable region (VH) having the amino acid sequence as set forth in SEQ ID NO: 1 and the light chain variable region (VL) having the amino acid sequence as set forth in SEQ ID NO: 5.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 6.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 7.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 8.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 5.

Still another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 7.

Yet another embodiment of aspect B is an isolated antibody or antigen-binding fragment thereof, comprising a heavy chain variable region (VH) having the amino acid sequence as set forth in SEQ ID NO: 1 and the light chain variable region (VL) having the amino acid sequence as set forth in SEQ ID NO: 8.

Another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 5.

Yet another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 7.

Still another embodiment of aspect B is an isolated antibody or antigen-binding fragment thereof, comprising a heavy chain variable region (VH) having the amino acid sequence as set forth in SEQ ID NO: 3 and the light chain variable region (VL) having the amino acid sequence as set forth in SEQ ID NO: 8.

Yet another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 5.

Still another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 6.

Another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 7.

Yet another embodiment of aspect B is an isolated antibody or antigen-binding fragment thereof, comprising a heavy chain variable region (VH) having the amino acid sequence as set forth in SEQ ID NO: 4 and the light chain variable region (VL) having the amino acid sequence as set forth in SEQ ID NO: 8.

Aspect C provides isolated antibodies of any of the embodiments described in the present application wherein the antibody comprises an Fc region and the Fc region has been engineered to reduce or eliminate one or more Fc effector function.

One embodiment of aspect C is where the Fc region is engineered such that the Fc region has reduced or eliminated binding to an Fc Receptor (FcR) or reduced or eliminated binding to C1q. In a particular embodiment of aspect C the FcR is FCγRIa (CD64), FCγRIIa (CD32), FCγRIIIa (CD16a), or FCγRIIIb (CD16b). In another embodiment of aspect C the FcR is FcγRIIa.

An embodiment of aspect C is an isolated antibody according to any one of the embodiments of the present invention, wherein the antibody is of the IgG1, IgG2, IgG3 or IgG4 isotype or any combination or hybrid version thereof. Another embodiment of aspect C is an isolated antibody according to any one of the embodiments of the present invention, wherein the antibody is of the IgG1 isotype, and wherein the heavy chain constant region comprises the amino acid sequence as set forth in SEQ ID NO: 21. (P238S and N297G) As shown in Experiment 3, none of the antibody clones provided in the present disclosure that were engineered with the Fc of SEQ ID NO: 21, bound to FCγRIa, FCγRIIa, FCγRIIIa, or FCγRIIIb. As shown in Experiment 4, none of the antibody clones provided in the present disclosure that were engineered with the Fc of SEQ ID NO: 21, bound to C1q.

A mutation of the IgG backbone Fc at position 297 (N297A) has been shown to abrogate IgG glycosylation and Fc gamma receptor binding. A mutation of the IgG backbone Fc at position 265 (D265A) has been shown to abrogate Fc gamma receptor binding. Accordingly embodiments of the present invention were prepared that comprised these mutations in the Fc region. One embodiment of aspect C is an isolated antibody according to any one the embodiments of the present disclosure which comprises a heavy chain constant region wherein the heavy chain constant region comprises the amino acid sequence as set forth in SEQ ID NO: 22. (D265A and N297A)

United States Patent Application publication number 2014/0294834 discloses a mutation of the heavy chain constant region. Thus, another embodiment is an isolated antibody according to any one of the embodiments having an Fc region that are disclosed in the present application, comprising a heavy chain constant region wherein the heavy chain constant region comprises the amino acid sequence as set forth in SEQ ID NO: 23. (T299K-MM131)

Another embodiment is an isolated antibody according to any one of the embodiments having an Fc region that are disclosed in the present application, comprising a heavy chain constant region wherein the heavy chain constant region comprises the amino acid sequence as set forth in SEQ ID NO: 24. (N299K)

In a particular embodiment the isolated antibody is the heavy chain variable region connected to the heavy chain constant region. In one embodiment the heavy chain variable region VH1 is connected directly to the heavy chain constant region having the P238S and N297G and the isolated antibody heavy chain consists of the amino acid sequence as provided in SEQ ID NO: 42. In another embodiment the heavy chain variable region VH2 is connected directly to the heavy chain constant region having the P238S and N297G and the isolated antibody heavy chain consists of the amino acid sequence as provided in SEQ ID NO: 43. In yet another embodiment the heavy chain variable region VH3 is connected directly to the heavy chain constant region having the P238S and N297G and the isolated antibody heavy chain consists of the amino acid sequence as provided in SEQ ID NO: 44. In still another embodiment the heavy chain variable region VH4 is connected directly to the heavy chain constant region having the P238S and N297G and the isolated antibody heavy chain consists of the amino acid sequence as provided in SEQ ID NO: 45.

In one embodiment the heavy chain variable region VH1 is connected directly to the heavy chain constant region having the D265A/N297A and the isolated antibody heavy chain consists of the amino acid sequence as provided in SEQ ID NO: 46. In yet another embodiment the heavy chain variable region VH2 is connected directly to the heavy chain constant region having the D265A/N297A and the isolated antibody heavy chain consists of the amino acid sequence as provided in SEQ ID NO: 47. In still another embodiment the heavy chain variable region VH3 is connected directly to the heavy chain constant region having the 265A/N297A and the isolated antibody heavy chain consists of the amino acid sequence as provided in SEQ ID NO: 48. In yet another embodiment the heavy chain variable region V4 is connected directly to the heavy chain constant region having the 265A/N297A and the isolated antibody heavy chain consists of the amino acid sequence as provided in SEQ ID NO: 49.

In still another embodiment the heavy chain variable region VH1 is connected directly to the heavy chain constant region having the IgG1/IgG4 hybrid and the isolated antibody heavy chain consists of the amino acid sequence as provided in SEQ ID NO: 50. In yet another embodiment the heavy chain variable region VH2 is connected directly to the heavy chain constant region having the IgG1/IgG4 hybrid and the isolated antibody heavy chain consists of the amino acid sequence as provided in SEQ ID NO: 51. In yet another embodiment the heavy chain variable region VH3 is connected directly to the heavy chain constant region having the IgG1/IgG4 hybrid and the isolated antibody heavy chain consists of the amino acid sequence as provided in SEQ ID NO: 51. In another embodiment the heavy chain variable region VH4 is connected directly to the heavy chain constant region having the IgG1/IgG4 hybrid and the isolated antibody heavy chain consists of the amino acid sequence as provided in SEQ ID NO: 53.

In another embodiment the heavy chain variable region VH1 is connected directly to the heavy chain constant region having the IgG4 and the isolated antibody heavy chain consists of the amino acid sequence as provided in SEQ ID NO: 54. In still another embodiment the heavy chain variable region VH2 is connected directly to the heavy chain constant region having the IgG4 and the isolated antibody heavy chain consists of the amino acid sequence as provided in SEQ ID NO: 55. In yet another embodiment the heavy chain variable region VH3 is connected directly to the heavy chain constant region having the IgG4 and the isolated antibody heavy chain consists of the amino acid sequence as provided in SEQ ID NO: 56. In another embodiment the heavy chain variable region VH4 is connected directly to the heavy chain constant region having the IgG4 and the isolated antibody heavy chain consists of the amino acid sequence as provided in SEQ ID NO: 57.

Yet another embodiment is an isolated antibody according to any one of the embodiments having a variable light chain and a light chain constant region wherein the light chain constant region comprises the sequence set forth in SEQ ID NO: 25. Another embodiment is a variable light chain 1 with the constant light chain region wherein the amino acid sequence is provided in SEQ ID NO: 38. Yet another embodiment is the variable light chain 2 with the constant light chain region wherein the amino acid sequence is provided in SEQ ID NO: 39. In still another embodiment the variable light chain 3 with the constant light chain region wherein the amino acid sequence is provided in SEQ ID NO: 40. In yet another embodiment the variable light chain 4 with the constant light chain region wherein the amino acid sequence is provided in SEQ ID NO: 41.

Another embodiment is a method for treating a subject with a CD40L-associated disease or disorder comprising administering to the subject a therapeutically effective amount of an antibody or antigen binding fragment thereof, disclosed in the present application.

Another embodiment is an isolated antibody having a heavy chain with the amino acid sequence as provided in SEQ ID NO: 42 and a light chain sequence as provided in SEQ ID NO: 38. Another embodiment is an isolated antibody having a heavy chain with the amino acid sequence as provided in SEQ ID NO: 43 and a light chain sequence as provided in SEQ ID NO: 38. Another embodiment is an isolated antibody having a heavy chain with the amino acid sequence as provided in SEQ ID NO: 44 and a light chain sequence as provided in SEQ ID NO: 38. Another embodiment is an isolated antibody having a heavy chain with the amino acid sequence as provided in SEQ ID NO: 45 and a light chain sequence as provided in SEQ ID NO: 38. Another embodiment is an isolated antibody having a heavy chain with the amino acid sequence as provided in SEQ ID NO:42 and a light chain sequence as provided in SEQ ID NO:39. Another embodiment is an isolated antibody having a heavy chain with the amino acid sequence as provided in SEQ ID NO: 43 and a light chain sequence as provided in SEQ ID NO: 39. Another embodiment is an isolated antibody having a heavy chain with the amino acid sequence as provided in SEQ ID NO: 44 and a light chain sequence as provided in SEQ ID NO: 39. Another embodiment is an isolated antibody having a heavy chain with the amino acid sequence as provided in SEQ ID NO: 45 and a light chain sequence as provided in SEQ ID NO: 39. Another embodiment is an isolated antibody having a heavy chain with the amino acid sequence as provided in SEQ ID NO: 42 and a light chain sequence as provided in SEQ ID NO: 40. Another embodiment is an isolated antibody having a heavy chain with the amino acid sequence as provided in SEQ ID NO: 43 and a light chain sequence as provided in SEQ ID NO: 40. Another embodiment is an isolated antibody having a heavy chain with the amino acid sequence as provided in SEQ ID NO: 44 and a light chain sequence as provided in SEQ ID NO: 40. Another embodiment is an isolated antibody having a heavy chain with the amino acid sequence as provided in SEQ ID NO: 45 and a light chain sequence as provided in SEQ ID NO: 40. Another embodiment is an isolated antibody having a heavy chain with the amino acid sequence as provided in SEQ ID NO: 42 and a light chain sequence as provided in SEQ ID NO: 41. Another embodiment is an isolated antibody having a heavy chain with the amino acid sequence as provided in SEQ ID NO: 43 and a light chain sequence as provided in SEQ ID NO: 41. Another embodiment is an isolated antibody having a heavy chain with the amino acid sequence as provided in SEQ ID NO: 44 and a light chain sequence as provided in SEQ ID NO: 41. Another embodiment is an isolated antibody having a heavy chain with the amino acid sequence as provided in SEQ ID NO: 45 and a light chain sequence as provided in SEQ ID NO: 41.

Another embodiment is an isolated antibody having a heavy chain with the amino acid sequence as provided in SEQ ID NO: 46 and a light chain with the amino acid sequence as provided in SEQ ID NO: 38. Another embodiment is an isolated antibody having a heavy chain with the amino acid sequence as provided in SEQ ID NO: 47 and a light chain amino acid sequence as provided in SEQ ID NO: 38. Another embodiment is an isolated antibody having a heavy chain with the amino acid sequence as provided in SEQ ID NO: 48 and a light chain amino acid sequence as provided in SEQ ID NO: 38. Another embodiment is an isolated antibody having a heavy chain with the amino acid sequence as provided in SEQ ID NO: 49 and a light chain amino acid sequence as provided in SEQ ID NO: 38. Another embodiment is an isolated antibody having a heavy chain with the amino acid sequence as provided in SEQ ID NO: 46 and a light chain amino acid sequence as provided in SEQ ID NO:39. Another embodiment is an isolated antibody having a heavy chain with the amino acid sequence as provided in SEQ ID NO: 47 and a light chain amino acid sequence as provided in SEQ ID NO: 39. Another embodiment is an isolated antibody having a heavy chain with the amino acid sequence as provided in SEQ ID NO: 48 and a light chain amino acid sequence as provided in SEQ ID NO: 39. Another embodiment is an isolated antibody having a heavy chain with the amino acid sequence as provided in SEQ ID NO: 49 and a light chain amino acid sequence as provided in SEQ ID NO: 39. Another embodiment is an isolated antibody having a heavy chain with the amino acid sequence as provided in SEQ ID NO: 46 and a light chain amino acid sequence as provided in SEQ ID NO: 40. Another embodiment is an isolated antibody having a heavy chain with the amino acid sequence as provided in SEQ ID NO: 47 and a light chain amino acid sequence as provided in SEQ ID NO: 40. Another embodiment is an isolated antibody having a heavy chain with the amino acid sequence as provided in SEQ ID NO: 48 and a light chain amino acid sequence as provided in SEQ ID NO: 40. Another embodiment is an isolated antibody having a heavy chain with the amino acid sequence as provided in SEQ ID NO: 49 and a light chain amino acid sequence as provided in SEQ ID NO: 40. Another embodiment is an isolated antibody having a heavy chain with the amino acid sequence as provided in SEQ ID NO: 46 and a light chain amino acid sequence as provided in SEQ ID NO: 41. Another embodiment is an isolated antibody having a heavy chain with the amino acid sequence as provided in SEQ ID NO: 47 and a light chain amino acid sequence as provided in SEQ ID NO: 41. Another embodiment is an isolated antibody having a heavy chain with the amino acid sequence as provided in SEQ ID NO: 48 and a light chain amino acid sequence as provided in SEQ ID NO: 41. Another embodiment is an isolated antibody having a heavy chain with the amino acid sequence as provided in SEQ ID NO: 49 and a light chain amino acid sequence as provided in SEQ ID NO: 41.

Another embodiment is an isolated antibody having a heavy chain with the amino acid sequence as provided in SEQ ID NO: 50 and a light chain amino acid sequence as provided in SEQ ID NO: 38. Another embodiment is an isolated antibody having a heavy chain with the amino acid sequence as provided in SEQ ID NO: 51 and a light chain amino acid sequence as provided in SEQ ID NO: 38. Another embodiment is an isolated antibody having a heavy chain with the amino acid sequence as provided in SEQ ID NO: 52 and a light chain amino acid sequence as provided in SEQ ID NO: 38. Another embodiment is an isolated antibody having a heavy chain with the amino acid sequence as provided in SEQ ID NO: 53 and a light chain amino acid sequence as provided in SEQ ID NO: 38. Another embodiment is an isolated antibody having a heavy chain with the amino acid sequence as provided in SEQ ID NO: 50 and a light chain amino acid sequence as provided in SEQ ID NO:39. Another embodiment is an isolated antibody having a heavy chain with the amino acid sequence as provided in SEQ ID NO: 51 and a light chain amino acid sequence as provided in SEQ ID NO: 39. Another embodiment is an isolated antibody having a heavy chain with the amino acid sequence as provided in SEQ ID NO: 52 and a light chain amino acid sequence as provided in SEQ ID NO: 39. Another embodiment is an isolated antibody having a heavy chain with the amino acid sequence as provided in SEQ ID NO: 53 and a light chain amino acid sequence as provided in SEQ ID NO: 39. Another embodiment is an isolated antibody having a heavy chain with the amino acid sequence as provided in SEQ ID NO: 50 and a light chain amino acid sequence as provided in SEQ ID NO: 40. Another embodiment is an isolated antibody having a heavy chain with the amino acid sequence as provided in SEQ ID NO: 51 and a light chain amino acid sequence as provided in SEQ ID NO: 40. Another embodiment is an isolated antibody having a heavy chain with the amino acid sequence as provided in SEQ ID NO: 52 and a light chain amino acid sequence as provided in SEQ ID NO: 40. Another embodiment is an isolated antibody having a heavy chain with the amino acid sequence as provided in SEQ ID NO: 53 and a light chain amino acid sequence as provided in SEQ ID NO: 40. Another embodiment is an isolated antibody having a heavy chain with the amino acid sequence as provided in SEQ ID NO: 50 and a light chain amino acid sequence as provided in SEQ ID NO: 41. Another embodiment is an isolated antibody having a heavy chain with the amino acid sequence as provided in SEQ ID NO: 51 and a light chain amino acid sequence as provided in SEQ ID NO: 41. Another embodiment is an isolated antibody having a heavy chain with the amino acid sequence as provided in SEQ ID NO: 52 and a light chain amino acid sequence as provided in SEQ ID NO: 41. Another embodiment is an isolated antibody having a heavy chain with the amino acid sequence as provided in SEQ ID NO: 53 and a light chain amino acid sequence as provided in SEQ ID NO: 41.

Another embodiment is an isolated antibody having a heavy chain with the amino acid sequence as provided in SEQ ID NO: 54 and a light chain amino acid sequence as provided in SEQ ID NO: 38. Another embodiment is an isolated antibody having a heavy chain with the amino acid sequence as provided in SEQ ID NO: 55 and a light chain amino acid sequence as provided in SEQ ID NO: 38. Another embodiment is an isolated antibody having a heavy chain with the amino acid sequence as provided in SEQ ID NO: 56 and a light chain amino acid sequence as provided in SEQ ID NO: 38. Another embodiment is an isolated antibody having a heavy chain with the amino acid sequence as provided in SEQ ID NO: 57 and a light chain amino acid sequence as provided in SEQ ID NO: 38. Another embodiment is an isolated antibody having a heavy chain with the amino acid sequence as provided in SEQ ID NO: 54 and a light chain amino acid sequence as provided in SEQ ID NO:39. Another embodiment is an isolated antibody having a heavy chain with the amino acid sequence as provided in SEQ ID NO: 55 and a light chain amino acid sequence as provided in SEQ ID NO: 39. Another embodiment is an isolated antibody having a heavy chain with the amino acid sequence as provided in SEQ ID NO: 56 and a light chain amino acid sequence as provided in SEQ ID NO: 39. Another embodiment is an isolated antibody having a heavy chain with the amino acid sequence as provided in SEQ ID NO: 57 and a light chain amino acid sequence as provided in SEQ ID NO: 39. Another embodiment is an isolated antibody having a heavy chain with the amino acid sequence as provided in SEQ ID NO: 54 and a light chain amino acid sequence as provided in SEQ ID NO: 40. Another embodiment is an isolated antibody having a heavy chain with the amino acid sequence as provided in SEQ ID NO: 55 and a light chain amino acid sequence as provided in SEQ ID NO: 40. Another embodiment is an isolated antibody having a heavy chain with the amino acid sequence as provided in SEQ ID NO: 56 and a light chain amino acid sequence as provided in SEQ ID NO: 40. Another embodiment is an isolated antibody having a heavy chain with the amino acid sequence as provided in SEQ ID NO: 57 and a light chain amino acid sequence as provided in SEQ ID NO: 40. Another embodiment is an isolated antibody having a heavy chain with the amino acid sequence as provided in SEQ ID NO: 54 and a light chain amino acid sequence as provided in SEQ ID NO: 41. Another embodiment is an isolated antibody having a heavy chain with the amino acid sequence as provided in SEQ ID NO: 55 and a light chain amino acid sequence as provided in SEQ ID NO: 41. Another embodiment is an isolated antibody having a heavy chain with the amino acid sequence as provided in SEQ ID NO: 56 and a light chain amino acid sequence as provided in SEQ ID NO: 41. Another embodiment is an isolated antibody having a heavy chain with the amino acid sequence as provided in SEQ ID NO: 57 and a light chain amino acid sequence as provided in SEQ ID NO: 41.

Yet another embodiment is a method for treating a subject with a neurodegenerative or a neuromuscular disease or disorder; an inflammatory or immune disease or disorder; or an autoimmune disease, comprising administering to the subject a therapeutically effective amount of an antibody or antigen binding fragment thereof, disclosed in the present application.

Another embodiment is a method for treating a subject with a an autoimmune disease, selected from the group consisting of systemic lupus erythematous, type-1 diabetes, Myasthenia gravis, psoriasis, Addison's disease, Crohn's disease, uveitis, multiple sclerosis, hemolytic anemia, inflammatory bowel disease, immune thrombocytopenic purpura, Graves' disease, and rheumatoid arthritis, comprising administering to the subject a therapeutically effective amount of an antibody or antigen binding fragment thereof, disclosed in the present application.

Still another embodiment is a method for treating a subject having a neurodegenerative disorder or a neuromuscular disorder selected from the group consisting of Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, and Spinocerebellar Ataxia comprising administering to the subject a therapeutically effective amount of an antibody or antigen binding fragment thereof disclosed in the present application.

Yet another embodiment is a method for treating a subject having Amyotrophic Lateral Sclerosis comprising administering to the subject a therapeutically effective amount of an antibody or antigen binding fragment thereof, disclosed in the present application.

Another embodiment is a method for inhibiting an immune response in a subject comprising administering to the subject a therapeutically effective amount of an antibody or antigen binding fragment thereof, disclosed in the present application.

Another embodiment is a method of inhibiting an immune response in a subject comprising administering to the subject a therapeutically effective amount of an antibody or antigen binding fragment thereof, wherein the immune response is graft vs. host disease, or organ transplant rejection.

Yet another embodiment is a method according to any of the methods of the present disclosure, wherein the antibody or antibody fragment is administered in combination with another therapeutic agent. One embodiment is a method according to any of the methods of the present disclosure, wherein the antibody or antibody fragment is administered in combination with a compound that blocks the interaction between CD28 and CD86 or between CD28 and CD80.

Still another embodiment is a method according to any of the methods of the present disclosure, wherein the antibody or antibody fragment is administered in combination with compound that blocks the interaction between CD28 and CD86 or between CD28 and CD80 is a CTLA4-Ig fusion protein.

Yet another embodiment is a method according to any of the methods of the present disclosure, wherein the antibody or antibody fragment is administered in combination with compound that blocks the interaction between CD28 and CD86 or between CD28 and CD80 is abatacept or belatacept or galiximab.

TABLE 1

Sequences

| Description | Sequence | SEQ ID NO: |
|---|---|---|
| Heavy chain 1 (VH1) | EVQLVQSGAEVKKPGASVKVSCKASGYTFT<u>SYYMY</u>WVRQ APGQGLEWMG<u>EINPSNGDTNYAQKFQ</u>GRVTMTVDTSTST VYMELSSLRSEDTAVYYCAR<u>SDGRNDMD</u>SWGQGTLVTVS S | 1 |
| Heavy chain 2 (VH2) | EVQLVQSGAEVKKPGASVKVSCKASGYIFT<u>SYYMY</u>WVRQ APGQGLEWMG<u>EINPSNGDTNYAEKFK</u>GRVTMTVDTSTST VYMELSSLRSEDTAVYYCTR<u>SDGRNDMD</u>SWGQGTLVTVS S | 2 |
| Heavy chain 3 (VH3) | EVQLVQSGAEVKKPGASVKVSCKASGYIFT<u>SYYMY</u>WVRQ APGQGLEWIG<u>EINPSNGDTNYAEKFK</u>GRATLTVDTSTST VYMELSSLRSEDTAVYYCTR<u>SDGRNDMD</u>SWGQGTLVTVS S | 3 |
| Heavy chain 4 (VH4) | QVQLVQSGAEVKKPGASVKVSCKASGYIFT<u>SYYMY</u>WVRQ APGQGLEWIG<u>EINPSNGDTNFAEKFK</u>GRATLTVDTSTST VYMELSSLRSEDTAVYYCTR<u>SDGRNDMD</u>SWGQGTLVTVS S | 4 |
| Light chain 1 (VL1) | EIVLTQSPATLSLSPGERATLSC<u>RASQRVSSSTYSYMH</u>W YQQKPGQAPRLLIY<u>DASNRAT</u>GIPARFSGSGSGTDFTLT ISSLEPEDFAVYYC<u>QHSWEIPPT</u>FGQGTKLEIK | 5 |
| Light chain 2 (VL2) | EIVLTQSPATLSLSPGERATLSC<u>RADERVSSSTYSYMH</u>W YQQKPGQAPRLLIY<u>DASNRAT</u>GIPARFSGSGSGTDFTLT ISSLEPEDFAVYYC<u>QHSWEIPPT</u>FGQGTKLEIK | 6 |
| Light chain 3 (VL3) | EIVLTQSPATLSLSPGERATLSC<u>RASQRVSSSTYSYMH</u>W YQQKPGQAPRLLIK<u>YASNRET</u>GIPARFSGSGSGTDFTLT ISSLEPEDFAVYYC<u>QHSWEIPPT</u>FGQGTKLEIK | 7 |

TABLE 1 -continued

Sequences

| Description | Sequence | SEQ ID NO: |
|---|---|---|
| Light chain 4 (VL4) | EIVLTQSPATLSLSPGERATLSC<u>RADERVSSSTYSYMH</u>W YQQKPGQAPRLLIK<u>YASNRET</u>GIPARFSGSGSGTDFTLT ISSLEPEDFAVYYC<u>QHSWEIPPT</u>FGQGTKLEIK | 8 |
| Heavy chain CDR1 | SYYMY | 9 |
| Heavy chain H1 CDR2 | EINPSNGDTNYAQKFQG | 10 |
| Heavy chain H2 CDR2A (CDR2 and flanking region RV) | EINPSNGDTNYAEKFKGRV | 11 |
| Heavy chain H3 CDR2B (CDR2 and flanking region RA) | EINPSNGDTNYAEKFKGRA | 12 |
| Heavy chain H4 CDR2 | EINPSNGDTNFAEKFKG | 13 |
| Heavy chain H2 and H3 CDR2 | EINPSNGDTNYAEKFKG | 14 |
| Heavy Chain CDR3 | SDGRNDMDS | 15 |
| Light Chain CDR1 L1 and L4 | RASQRVSSSTYSYMH | 16 |
| Light Chain CDR1 L2 and L4 | RADERVSSSTYSYMH | 17 |
| Light Chain CDR2 L1 and L2 | DASNRAT | 18 |
| Light Chain CDR2 L3 and L4 | YASNRET | 19 |
| Light Chain CDR3 | QHSWEIPPT | 20 |
| Engineered effectorless IgG1Fc with P238S and N297G mutations (underlined) | EPKSCDKTHTCPPCPAPELLGG<u>S</u>SVFLFPPKPKDTLMISRTP EVTCVVVDVSHEDPEVKFNWYVDGVEVHNAKTKPREEQY<u>G</u>ST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 21 |
| Engineered D265A/N297A effectorless IgG1 constant heavy chain | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPELLGGPSVFLF PPKPKDTLMISRTPEVTCVVV<u>A</u>VSHEDPEVKFNWYVDGVEVH NAKTKPREEQY<u>A</u>STYRVVSVLTVLHQDWLNGKEYKCKVSNKA LPAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPG | 22 |
| Engineered effectorless IgG1/IgG4 hybrid constant heavy chain sequence | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPSCPAPEFLGGPSVFLF PPKPKDTLMISRTPEVTCVVVDVSQEDPEVQFNWYVDGVEVH NAKTKPREEQFN<u>S</u>KYRVVSVLTVLHQDWLNGKEYKCKVSNKG LPSSIEKTISKAKGQPREPQVYTLPPSREEMTKNQVSLSCAV KGFYPSDIAVEWESNGQPENNYKTTPPVLDSDGSFFLVSKLT VDKSRWQQGNVFSCSVMHEALHNHYTQKSLSLSPG | 23 |
| Engineered effectorless IgG4 constant heavy chain sequence | ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPPCPAPEFLGGPSVFLFPPK PKDTLMISRTPEVICVVVDVSQEDPEVQFNWYVDGVEVHNAK TKPREEQFN<u>S</u>KYRVVSVLTVLHQDWLNGKEYKCKVSNKGLPS SIEKTISKAKGQPREPQVYTLPPSQEEMTKNQVSLTCLVKGF YPSDIAVEWESNGQPENNYKTTPPVLDSDGSFFLYSRLTVDK SRWQEGNVFSCSVMHEALHNHYTQKSLSLSLG | 24 |

TABLE 1 -continued

Sequences

| Description | Sequence | SEQ ID NO: |
|---|---|---|
| Constant light chain sequence | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 25 |
| Heavy chain 1 (VH1) DNA | GAGGTGCAGCTGGTGCAGTCCGGCGCCGAGGTGAAGAAGCCC GGCGCCTCCGTGAAGGTGTCCTGCAAGGCCTCCGGCTACACC TTCACCTCCTACTACATGTACTGGGTGAGGCAGGCCCCCGGC CAGGGCCTGGAGTGGATGGGCGAGATCAACCCCTCCAACGGC GACACCAACTACGCACAGAAGTTCCAGGGTAGGGTCACCATG ACCGTGGACACGTCCACCTCCACCGTCTACATGGAGCTGTCC TCCCTGAGGTCCGAGGACACCGCCGTGTACTACTGCGCCAGG TCCGACGGCAGGAACGACATGGACTCCTGGGGCCAGGGCACC CTGGTGACCGTGTCCTCC | 26 |
| Heavy chain 2 (VH2) DNA | GAGGTGCAGCTGGTGCAGTCCGGCGccGAGGTGAAGAAGCCC GGCGCCTCCGTGAAGGTGTCCTGCAAGGCCTCCGGCTACATC TTCACCTCCTACTACATGTACTGGGTGAGGCAGGCCCCCGGC CAGGGCCTGGAGTGGATGGGCGAGATCAACCCCTCCAACGGC GACACCAACTACGCAGAGAAGTTCAAGGGTAGGGTCACCATG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 27 |
| Heavy chain 3 (VH3) DNA | GAGGTGCAGCTGGTGCAGTCCGGCGCCGAGGTGAAGAAGCCC GGCGCCTCCGTGAAGGTGTCCTGCAAGGCCTCCGGCTACATC TTCACCTCCTACTACATGTACTGGGTGAGGCAGGCCCCCGGC CAGGGCCTGGAGTGGATCGGCGAGATCAACCCCTCCAACGGC GACACCAACTACGCAGAGAAGTTCAAGGGTAGGGCCACCCTG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 28 |
| Heavy chain 4 (VH4) DNA | CAGGTGCAGCTGGTGCAGTCCGGCGCCGAGGTGAAGAAGCCC GGCGCCTCCGTGAAGGTGTCCTGCAAGGCCTCCGGCTACATC TTCACCTCCTACTACATGTACTGGGTGAGGCAGGCCCCCGGC CAGGGCCTGGAGTGGATCGGCGAGATCAACCCCTCCAACGGC GACACCAACTTCGCAGAGAAGTTCAAGGGTAGGGCCACCCTG ACCGTGGACACGTCCACCTCCACCGTCTACATGGAGCTGTCC TCCCTGAGGTCCGAGGACACCGCCGTGTACTACTGCACCAGG TCCGACGGCAGGAACGACATGGACTCCTGGGGCCAGGGCACC CTGGTGACCGTGTCCTCC | 29 |
| Light chain 1 (VL1) DNA | GAGATCGTGCTGACCCAGTCACCTGCCACCCTGTCCCTGTCA CCTGGAGAGAGAGCCACCCTCTCCTGCAGAGCCTCCCAGAGG GTGTCCTCCTCCACCTACTCCTACATGCACTGGTACCAGCAG AAGCCTGGACAGGCACCTAGGCTGCTGATCTACGACGCCTCC AACAGGGCGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 30 |
| Light chain 2 (VL2) DNA | GAGATCGTGCTGACCCAGTCACCTGCCACCCTGTCCCTGTCA CCTGGAGAGAGAGCCACCCTCTCCTGCAGAGCCGATGAGAGG GTGTCCTCCTCCACCTACTCCTACATGCACTGGTACCAGCAG AAGCCTGGACAGGCACCTAGGCTGCTGATCTACGACGCCTCC AACAGGGCGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 31 |
| Light chain 3 (VL3) DNA | GAGATCGTGCTGACCCAGTCACCTGCCACCCTGTCCCTGTCA CCTGGAGAGAGAGCCACCCTCTCCTGCAGAGCCTCCCAGAGG GTGTCCTCCTCCACCTACTCCTACATGCACTGGTACCAGCAG AAGCCTGGACAGGCACCTAGGCTGCTGATCAAGTACGCCTCC AACAGGGAGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | 32 |
| Light chain 4 (VL4) DNA | GAGATCGTGCTGACCCAGTCACCTGCCACCCTGTCCCTGTCA CCTGGAGAGAGAGCCACCCTCTCCTGCAGAGCCGATGAGAGG GTGTCCTCCTCCACCTACTCCTACATGCACTGGTACCAGCAG | 33 |

TABLE 1 -continued

Sequences

| Description | Sequence | SEQ ID NO: |
|---|---|---|
| | AAGCCTGGACAGGCACCTAGGCTGCTGATCAAGTACGCCTCC AACAGGGAGACCGGTATACCAGCCAGGTTCTCAGGCTCAGGC TCAGGCACCGACTTCACCCTGACCATCTCCTCCCTGGAGCCA GAGGACTTCGCCGTCTACTACTGCCAGCACTCCTGGGAGATC CCACCTACCTTCGGACAAGGCACCAAGCTGGAAATCAAA | |
| Fc fragment of IgG, high affinity Ia, receptor (CD64) (FCγRIa) | MWFLTTLLLWVPVDGQVDTTKAVITLQPPWVSVFQEETVTLH CEVLHLPGSSSTQWFLNGTATQTSTPSYRITSASVNDSGEYR CQRGLSGRSDPIQLEIHRGWLLLQVSSRVFTEGEPLALRCHA WKDKLVYNVLYYRNGKAFKFFHWNSNLTILKTNISHNGTYHC SGMGKHRYTSAGISVTVKELFPAPVLNASVTSPLLEGNLVTL SCETKLLLQRPGLQLYFSFYMGSKTLRGRNTSSEYQILTARR EDSGLYWCEAATEDGNVLKRSPELELQVLGLQLPTPVWFHVL FYLAVGIMFLVNTVLWVTIRKELKRKKKWDLEISLDSGHEKK VISSLQEDRHLEEELKCQEQKEEQLQEGVHRKEPQGAT | 34 |
| Low affinity immunoglobulin gamma Fc region acceptor IIa (FCγRIIa) (CD32) | MTMETQMSQNVCPRNLWLLQPLTVLLLLASADSQAAPPKAVL KLEPPWINVLQEDSVTLICQGARSPESDSIQWFHNGNLIPTH TQPSYRFKANNNDSGEYTCQTGQTSLSDPVHLTVLSEWLVLQ TPHLEFQEGETIMLRCHSWKDKPLVKVTFFQNGKSQKFSHLD PTFSIPQANHSHSGDYHCTGNIGYTLFSSKPVTITVQVPSMG SSSPMGVIVAVVIATAVAAIVAAVVALIYCRKKRISANSTDP VKAAQFEPPGRQMIAIRKRQLEETNNDYETADGGYMTLNPRA PTDDDKNIYLTLPPNDHVNSNN | 35 |
| low affinity immunoglobulin gamma Fc region receptor IIIa (FCγRIIIA) (CD16a) | MGGGAGERLFTSSCLVGLVPLGLRISLVTCPLQCGIMWQLLL PTALLLLVSAGMRTEDLPKAVVFLEPQWYRVLEKDSVTLKCQ GAYSPEDNSTQWFHNESLISSQASSYFIDAATVDDSGEYRCQ TNLSTLSDPVQLEVHIGWLLLQAPRWVFKEEDPIHLRCHSWK NTALHKVTYLQNGKGRKYFHHNSDFYIPKATLKDSGSYFCRG LVGSKNVSSETVNITITQGLAVSTISSFFPPGYQVSFCLVMV LLFAVDTGLYFSVKTNIRSSTRDWKDHKFKWRKDPQDK | 36 |
| Low affinity immunoglobulin gamma Fc region receptor IIIb (FCγRIIIb) (CD16b)) | MWQLLLPTALLLLVSAGMRTEDLPKAVVFLEPQWYSVLEKDS VTLKCQGAYSPEDNSTQWFHNESLISSQASSYFIDAATVNDS GEYRCQTNLSTLSDPVQLEVHIGWLLLQAPRWVFKEEDPIHL RCHSWKNTALHKVTYLQNGKDRKYFHHNSDFHIPKATLKDSG SYFCRGLVGSKNVSSETVNITITQGLAVSTISSFSPPGYQVS FCLVMVLLFAVDTGLYFSVKTNI | 37 |
| Light chain 1 with constant light chain (VL1-C) | EIVLTQSPAILSLSPGERATLSCRASQRVSSSTYSYMHWYQQ KPGQAPRLLIYDASNRATGIPARFSGSGSGTDFTLTISSLEP EDFAVYYCQHSWEIPPTFGQGTKLEIKRTVAAPSVFIFPPSD EQLKSGTASVVCLLNNFYPREAKVQWKVDNALQSGNSQESVT EQDSKDSTYSLSSTLTLSKADYEKHKVYACEVTHQGLSSPVT KSFNRGEC | 38 |
| Light chain 2 with constant light chain (VL2-C) | EIVLTQSPATLSLSPGERATLSCRADERVSSSTYSYMHW YQQKPGQAPRLLIYDASNRATGIPARFSGSGSGTDFTLT ISSLEPEDFAVYYCQHSWEIPPTFGQGTKLEIKRTVAAP SVFIFPPSDEQLKSGTASVVCLLNNFYPREAKVQNKVDNALQ SGNSQESVTEQDSKDSTYSLSSTLTLSKADYEKHKVYACEVT HQGLSSPVTKSFNRGEC | 39 |
| Light chain 3 with constant light chain (VL3-C) | EIVLTQSPATLSLSPGERATLSCRASQRVSSSTYSYMHW YQQKPGQAPRLLIKYASNRETGIPARFSGSGSGTDFTLT ISSLEPEDFAVYYCQHSWEIPPTFGQGTKLEIKRTVAAP SVFIFPPSDEQLKSGTASVVCLLNNFYPREAKVQNKVDNALQ SGNSQESVTEQDSKDSTYSLSSTLTLSKADYEKHKVYACEVT HQGLSSPVTKSFNRGEC | 40 |
| Light chain 4 with constant light chain (VL4-C) | EIVLTQSPATLSLSPGERATLSCRADERVSSSTYSYMHW YQQKPGQAPRLLIKYASNRETGIPARFSGSGSGTDFTLT ISSLEPEDFAVYYCQHSWEIPPTFGQGTKLEIKRTVAAP SVFIFPPSDEQLKSGTASVVCLLNNFYPREAKVQWKVDNALQ SGNSQESVTEQDSKDSTYSLSSTLTLSKADYEKHKVYACEVT HQGLSSPVTKSFNRGEC | 41 |
| Heavy chain 1-IgG1Fc with P238S and N297G mutations (VH1-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 42 |

TABLE 1 -continued

Sequences

| Description | Sequence | SEQ ID NO: |
|---|---|---|
| Heavy chain 2-IgG1Fc with P238S and N297G mutations (VH2-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 43 |
| Heavy chain 3-IgG1Fc with P238S and N297G mutations (VH3-Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 44 |
| Heavy chain 4-IgG1Fc with P238S and N297G mutations (VH4Fc-P238/N297) | EPKSCDKTHTCPPCPAPELLGGSSVFLFPPKPKDILMISRTP EVTCVVVDVSHEDPEVKFNWYVDGVEVHNAKTKPREEQYGST YRVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK | 45 |
| Heavy chain 1-Fc D265A/N297A effectorless IgG1 (VH1-Fc-D265A/N297A) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 46 |
| Heavy chain 2-Fc D265A/N297A effectorless IgG1 (VH2-Fc-D265A/N297A) | EVQLVQSGAEVKKPGASVKVSCKASGYIFTSYYMYWVRQ APGQGLEWMGEINPSNGDTNYAEKFKGRVTMTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 47 |
| Heavy chain 3-Fc D265A/N297A effectorless IgG1 (VH3-Fc-D265A/N297A) | EVQLVQSGAEVKKPGASVKVSCKASGYIFTSYYMYWVRQ APGQGLEWIGEINPSNGDTNYAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 48 |
| Heavy chain 4-Fc D265A/N297A effectorless IgG1 (VH4-Fc-D265A/N297A) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVFL FPPKPKDTLMISRTPEVTCVVVAVSHEDPEVKFNWYVDGVEV HNAKTKPREEQYASTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG | 49 |
| Heavy chain 1-Fc effectorless IgG1/IgG4 hybrid (VH1-Fc-IgG1/IgG4 hybrid) | EVQLVQSGAEVKKPGASVKVSCKASGYTFTSYYMYWVRQ APGQGLEWMGEINPSNGDTNYAQKFQGRVTMTVDTSTST VYMELSSLRSEDTAVYYCARSDGRNDMDSWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPSCPAPEFLGGPSVFL | 50 |

TABLE 1 -continued

Sequences

| Description | Sequence | SEQ ID NO: |
|---|---|---|
| | FPPKPKDTLMISRTPEVICVVVDVSQEDPEVQFNWYVDGVEV<br>HNAKTKPREEQFNSKYRVVSVLTVLHQDWLNGKEYKCKVSNK<br>GLPSSIEKTISKAKGQPREPQVYTLPPSREEMTKNQVSLSCA<br>VKGFYPSDIAVEWESNGQPENNYKTTPPVLDSDGSFFLVSKL<br>TVDKSRWQQGNVFSCSVMHEALHNHYTQKSLSLSPG | |
| Heavy chain 2-Fc effectorless IgG1/IgG4 hybrid (VH2-Fc-IgG1/IgG4 hybrid) | EVQLVQSGAEVKKPGASVKVSCKASGYIFTSYYMYWVRQ<br>APGQGLEWMGEINPSNGDTNYAEKFKGRVTMTVDTSTST<br>VYMELSSLRSEDTAVYYCTRSDGRNDMDSWGQGTLVTVS<br>SASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPSCPAPEFLGGPSVFL<br>FPPKPKDTLMISRTPEVICVVVDVSQEDPEVQFNWYVDGVEV<br>HNAKTKPREEQFNSKYRVVSVLTVLHQDWLNGKEYKCKVSNK<br>GLPSSIEKTISKAKGQPREPQVYTLPPSREEMTKNQVSLSCA<br>VKGFYPSDIAVEWESNGQPENNYKTTPPVLDSDGSFFLVSKL<br>TVDKSRWQQGNVFSCSVMHEALHNHYTQKSLSLSPG | 51 |
| Heavy chain 3-Fc effectorless IgG1/IgG4 hybrid (VH3-Fc-IgG1/IgG4 hybrid) | EVQLVQSGAEVKKPGASVKVSCKASGYIFTSYYMYWVRQ<br>APGQGLEWIGEINPSNGDTNYAEKFKGRATLTVDTSTST<br>VYMELSSLRSEDTAVYYCTRSDGRNDMDSWGQGTLVTVS<br>SASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPSCPAPEFLGGPSVFL<br>FPPKPKDTLMISRTPEVICVVVDVSQEDPEVQFNWYVDGVEV<br>HNAKTKPREEQFNSKYRVVSVLTVLHQDWLNGKEYKCKVSNK<br>GLPSSIEKTISKAKGQPREPQVYTLPPSREEMTKNQVSLSCA<br>VKGFYPSDIAVEWESNGQPENNYKTTPPVLDSDGSFFLVSKL<br>TVDKSRWQQGNVFSCSVMHEALHNHYTQKSLSLSPG | 52 |
| Heavy chain 4-Fc effectorless IgG1/IgG4 hybrid (VH4-Fc-IgG1/IgG4 hybrid) | QVQLVQSGAEVKKPGASVKVSCKASGYIFTSYYMYWVRQ<br>APGQGLEWIGEINPSNGDTNFAEKFKGRATLTVDTSTST<br>VYMELSSLRSEDTAVYYCTRSDGRNDMDSWGQGTLVTVS<br>SASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPSCPAPEFLGGPSVFL<br>FPPKPKDTLMISRTPEVICVVVDVSQEDPEVQFNWYVDGVEV<br>HNAKTKPREEQFNSKYRVVSVLTVLHQDWLNGKEYKCKVSNK<br>GLPSSIEKTISKAKGQPREPQVYTLPPSREEMTKNQVSLSCA<br>VKGFYPSDIAVEWESNGQPENNYKTTPPVLDSDGSFFLVSKL<br>TVDKSRWQQGNVFSCSVMHEALHNHYTQKSLSLSPG | 53 |
| Heavy chain 1-Fc effectorless IgG4 constant heavy chain (VH1-Fc-IgG4) | EVQLVQSGAEVKKPGASVKVSCKASGYTFTSYYMYWVRQ<br>APGQGLEWMGEINPSNGDTNYAQKFQGRVTMTVDTSTST<br>VYMELSSLRSEDTAVYYCARSDGRNDMDSWGQGTLVTVS<br>SASTKGPSVFPLAPCSRSTSESTAALGCLVKDYFPEPVTVSW<br>NSGALTSGVHTFPAVLQSSGLYSLSSVVTVPSSSLGTKTYTC<br>NVDHKPSNTKVDKRVESKYGPPCPPCPAPEFLGGPSVFLFPP<br>KPKDILMISRIPEVICVVVDVSQEDPEVQFNWYVDGVEVHNA<br>KTKPREEQFNSKYRVVSVLTVLHQDWLNGKEYKCKVSNKGLP<br>SSIEKTISKAKGQPREPQVYTLPPSQEEMTKNQVSLTCLVKG<br>FYPSDIAVEWESNGQPENNYKTTPPVLDSDGSFFLYSRLTVD<br>KSRWQEGNVFSCSVMHEALHNHYTQKSLSLSLG | 54 |
| Heavy chain 2-Fc effectorless IgG4 constant heavy chain (VH2-Fc-IgG4) | EVQLVQSGAEVKKPGASVKVSCKASGYIFTSYYMYWVRQ<br>APGQGLEWMGEINPSNGDTNYAEKFKGRVTMTVDTSTST<br>VYMELSSLRSEDTAVYYCTRSDGRNDMDSWGQGTLVTVS<br>SASTKGPSVFPLAPCSRSTSESTAALGCLVKDYFPEPVTVSW<br>NSGALTSGVHTFPAVLQSSGLYSLSSVVTVPSSSLGTKTYTC<br>NVDHKPSNTKVDKRVESKYGPPCPPCPAPEFLGGPSVFLFPP<br>KPKDILMISRIPEVICVVVDVSQEDPEVQFNWYVDGVEVHNA<br>KTKPREEQFNSKYRVVSVLTVLHQDWLNGKEYKCKVSNKGLP<br>SSIEKTISKAKGQPREPQVYTLPPSQEEMTKNQVSLTCLVKG<br>FYPSDIAVEWESNGQPENNYKTTPPVLDSDGSFFLYSRLTVD<br>KSRWQEGNVFSCSVMHEALHNHYTQKSLSLSLG | 55 |
| Heavy chain 3-Fc effectorless IgG4 constant heavy chain (VH3-Fc-IgG4) | EVQLVQSGAEVKKPGASVKVSCKASGYIFTSYYMYWVRQ<br>APGQGLEWIGEINPSNGDTNYAEKFKGRATLTVDTSTST<br>VYMELSSLRSEDTAVYYCTRSDGRNDMDSWGQGTLVTVS<br>SASTKGPSVFPLAPCSRSTSESTAALGCLVKDYFPEPVTVSW<br>NSGALTSGVHTFPAVLQSSGLYSLSSVVTVPSSSLGTKTYTC<br>NVDHKPSNTKVDKRVESKYGPPCPPCPAPEFLGGPSVFLFPP<br>KPKDILMISRIPEVICVVVDVSQEDPEVQFNTNYVDGVEVHNA<br>KTKPREEQFNSKYRVVSVLTVLHQDTA7LNGKEYKCKVSNKGLP<br>SSIEKTISKAKGQPREPQVYTLPPSQEEMTKNQVSLTCLVKG | 56 |

TABLE 1 -continued

Sequences

| Description | Sequence | SEQ ID NO: |
|---|---|---|
| | FYPSDIAVETNESNGQPENNYKTTPPVLDSDGSFFLYSRLTVD KSRWQEGNVFSCSVMHEALHNHYTQKSLSLSLG | |
| Heavy chain 4-Fc effectorless IgG4 constant heavy chain (VH4-Fc-IgG4) | QVQLVQSGAEVKKPGASVKVSCKASGYIFTSYYMYWVRQ APGQGLEWIGEINPSNGDTNFAEKFKGRATLTVDTSTST VYMELSSLRSEDTAVYYCTRSDGRNDMDSWGQGTLVTVS SASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFPP KPKDILMISRIPEVICVVVDVSQEDPEVQFNTNYVDGVEVHNA KTKPREEQFNSKYRVVSVLTVLHQDTA7LNGKEYKCKVSNKGLP SSIEKTISKAKGQPREPQVYTLPPSQEEMTKNQVSLTCLVKG FYPSDIAVETNESNGQPENNYKTTPPVLDSDGSFFLYSRLTVD KSRWQEGNVFSCSVMHEALHNHYTQKSLSLSLG | 57 |

EXAMPLES

Example 1 CD40L Binding Assay

In order to make a comparison of CD40L binding of antibodies from all 16 clones versus 5c8 or AT-1501 a binding assay was run using 2 clones with 5c8 and AT-1501 run on the same 96-well assay plate. A three part sandwich ELISA assay was used to determine the level of binding of the antibodies of the present disclosure in comparison to reference antibodies 5c8-19 and AT1501. 96-well polystyrene plates were coated with recombinant human CD40L (BioLegend Cat. #591706) using 2 ug/ml in PBS and 50 ul/well was added to Costar 96-well ½ area high binding assay plates (Corning 3690) and incubated overnight at 4° C. Plates were blocked with (1×) PBS/1.0% BSA (140 ul/well) for 1 hour at room temperature to prevent background binding. Binding curves of 5C8 or AT1501 (from 2 ug/ml out serial 2-fold dilutions) were added (50 ul/well) and incubated for 1 hour at room temperature. Plates are washed and incubated with HRP-(Fab2) donkey anti-human IgG (Fc specific) (Jackson Immuno. 709-036-098) at a 1:10,000 dilution (50 ul/well) for 1 hour at room temperature. Plates were washed and TMB substrate (Surmodics BioFX TMBW-1000-01) was added (50 ul/well). Color development is stopped after 5 minutes at room temperature with 25 ul $2NH_2SO_4$. Plates are read on Molecular Devices SpectraMax M5 plate reader using SoftMax Pro 6.2.2 program to determine absorbance at 450 nm.

Figure 1A:
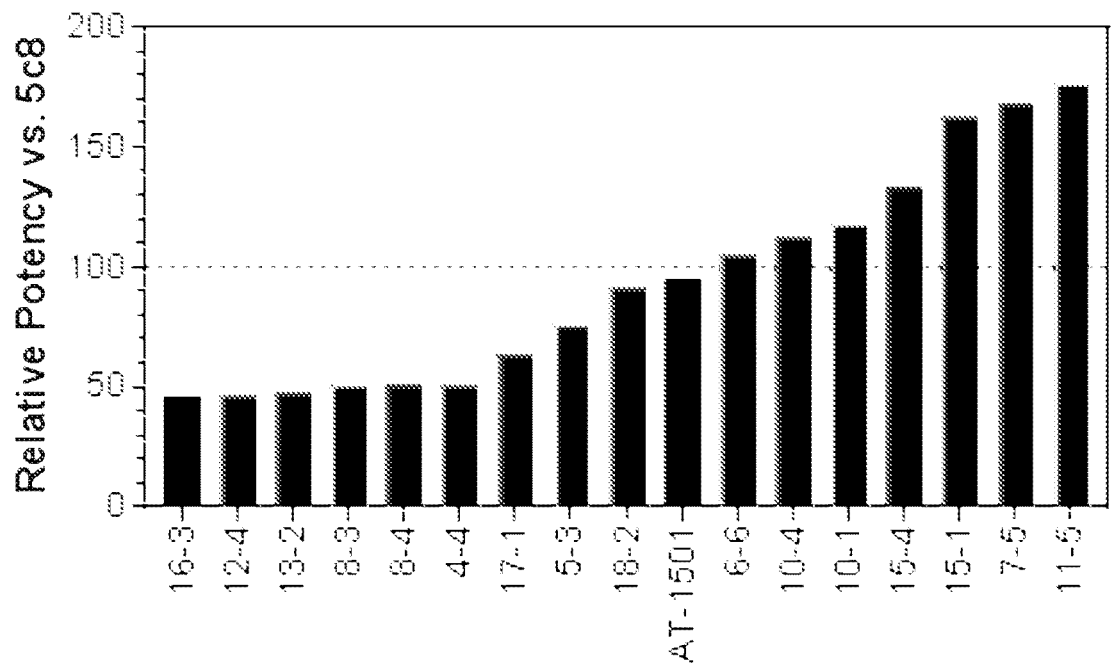
FIG. 1A is a bar graph showing the ranked potency of 16 antibody clones versus the anti-CD40L antibody 5c8. Ranked potency is IC50 clone/IC50 of 5c8×100.
Figure 1B:
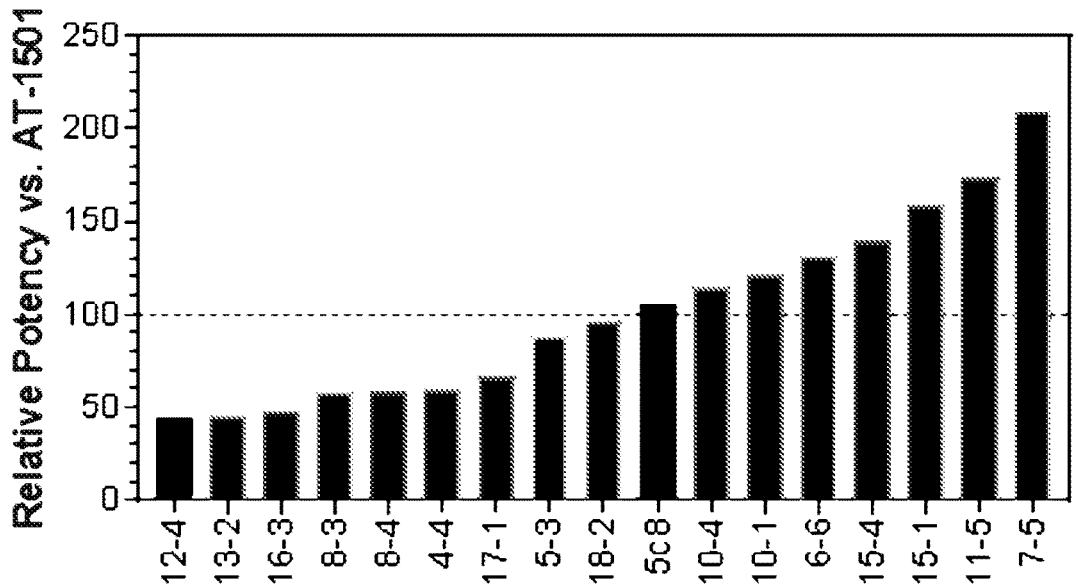
FIG. 1B is a bar graph showing the ranked potency of 16 antibody clones versus the anti-CD40L antibody AT-1501. Ranked potency is IC50 clone/IC50 of AT-1501×100.
Figure 2A:
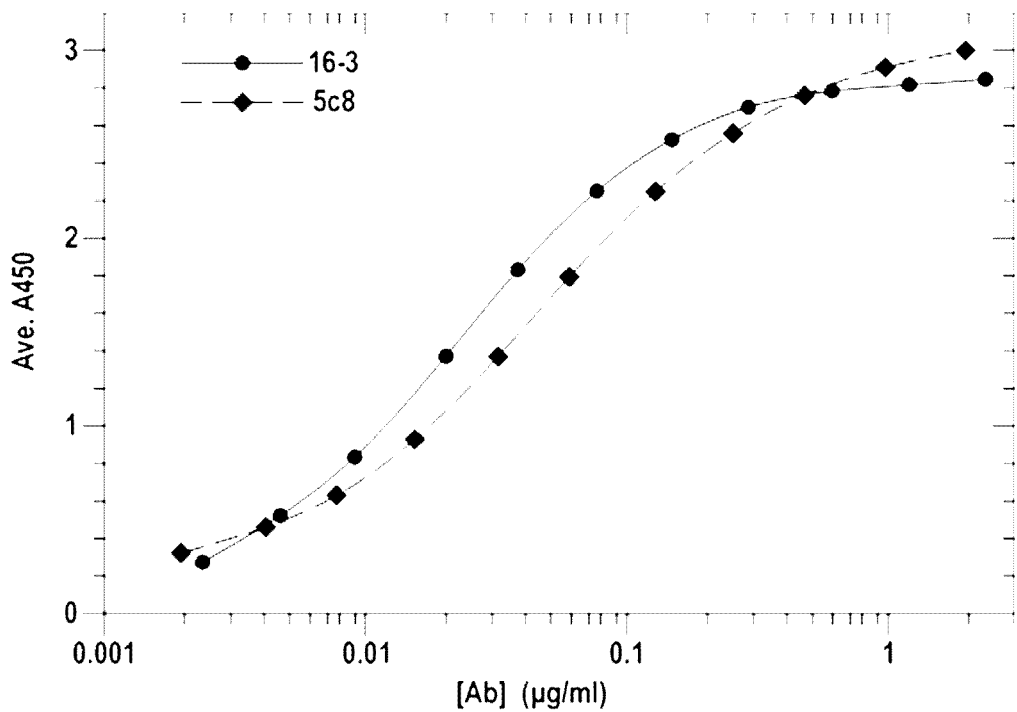
FIGS. 2A-2G and 2I-2Q show the binding curves of the antibodies from each of the clones with the binding curve for 5c8.
Figure 2B:
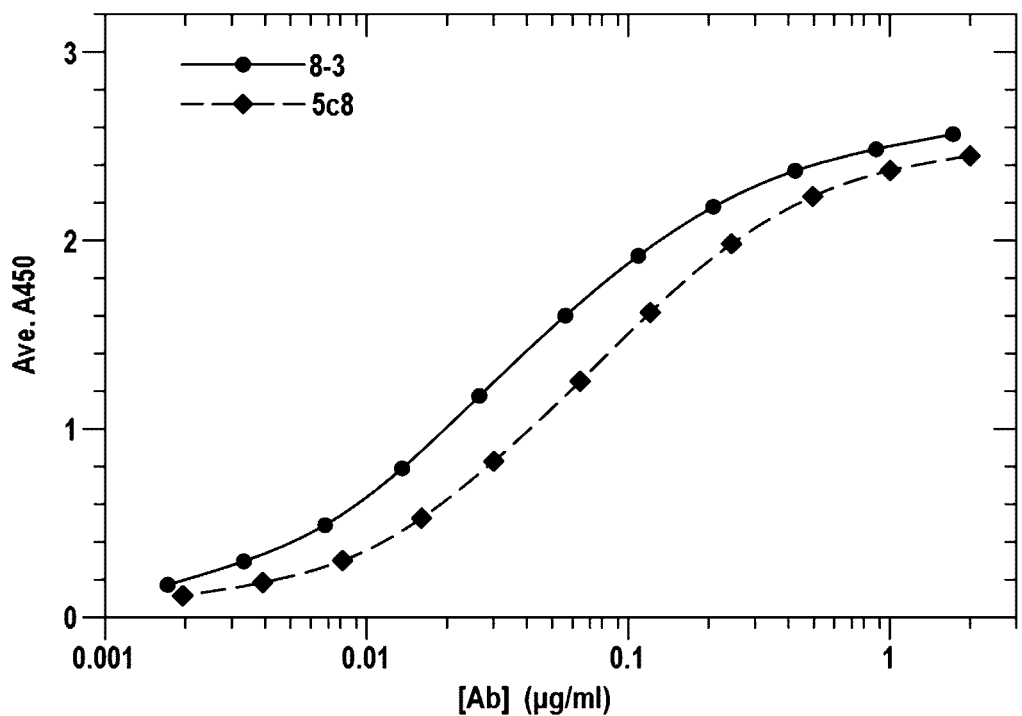
Figure 2C:
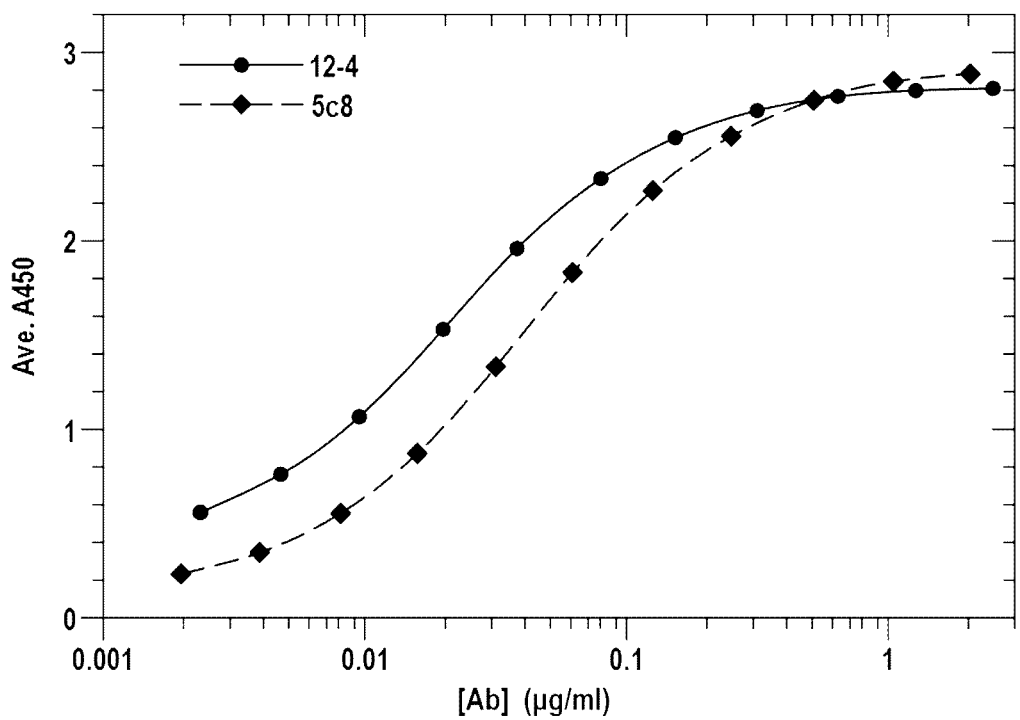
Figure 2D:
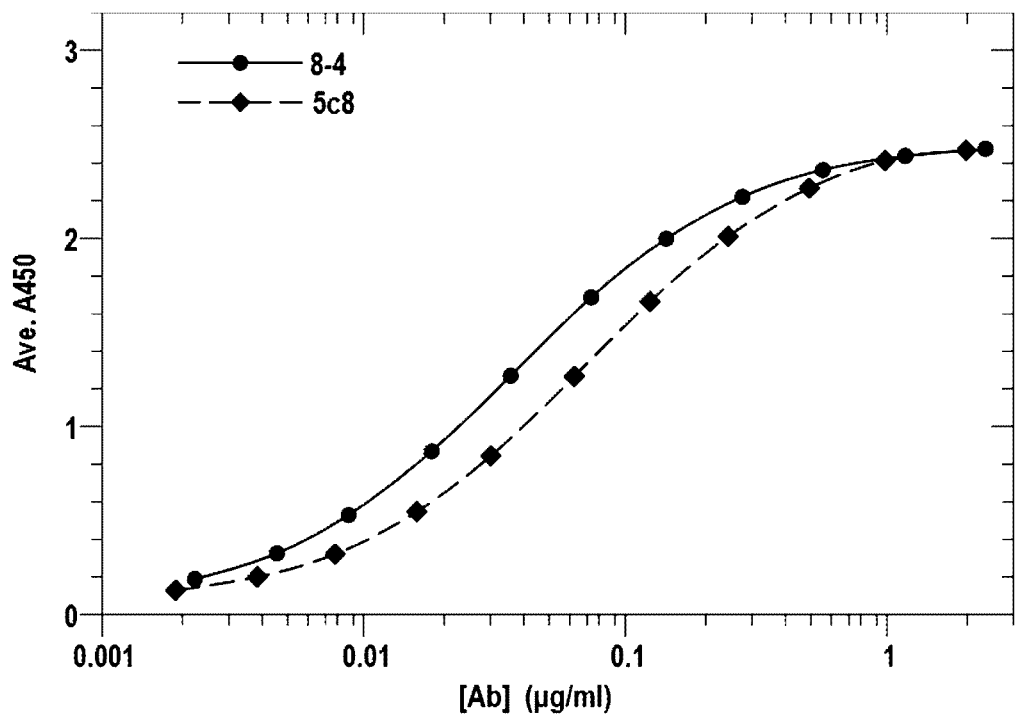
Figure 2E:
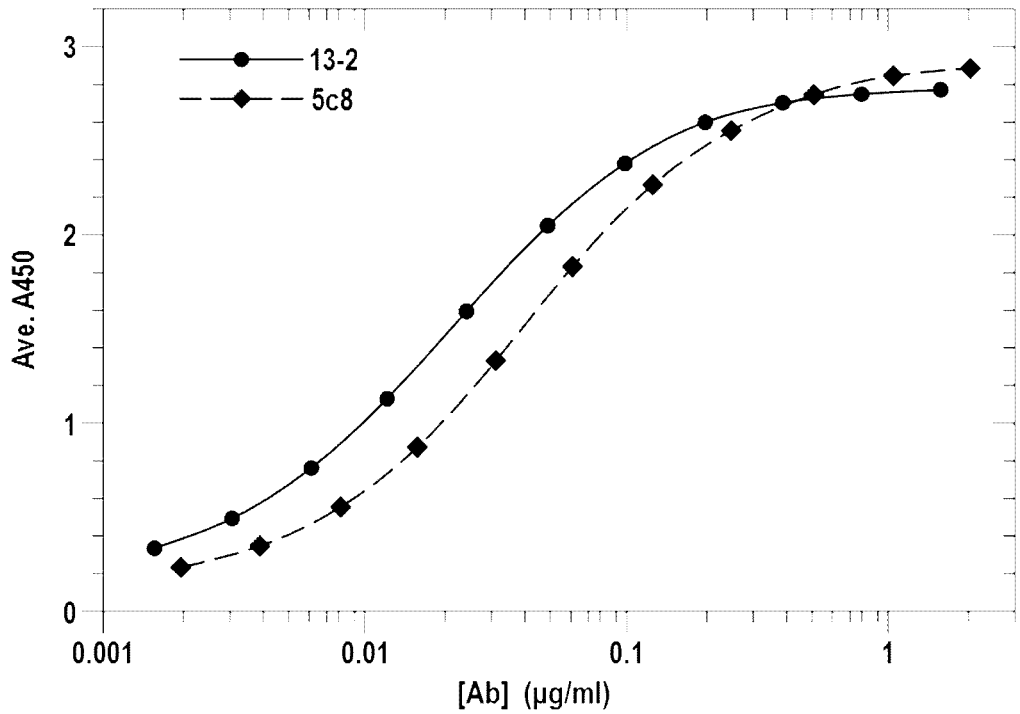
Figure 2F:
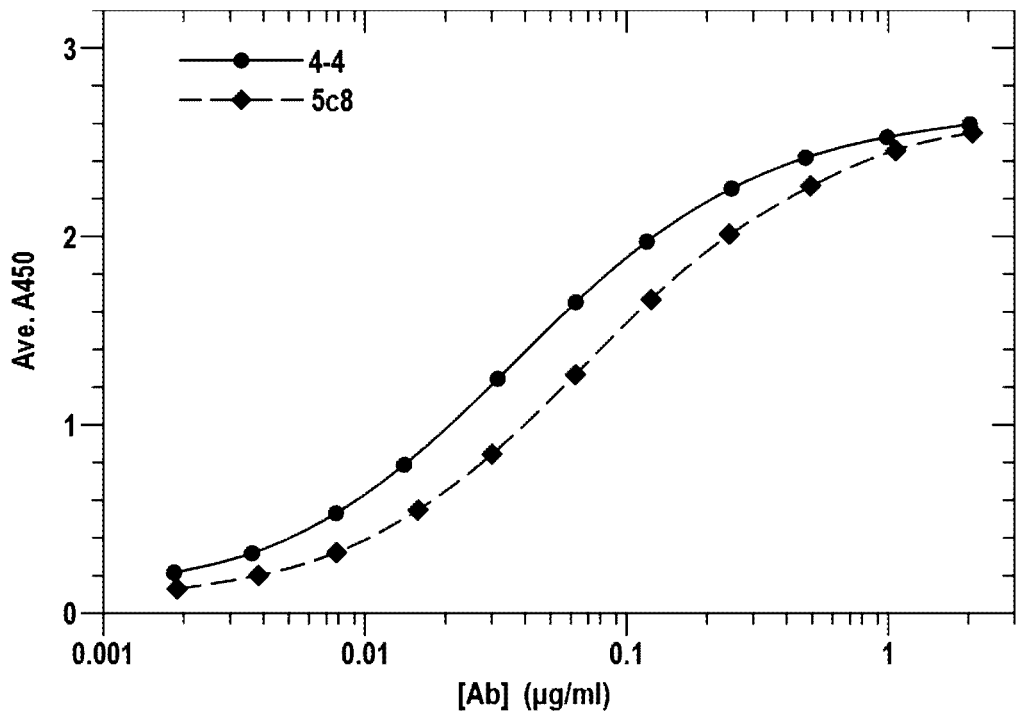
Figure 2G:
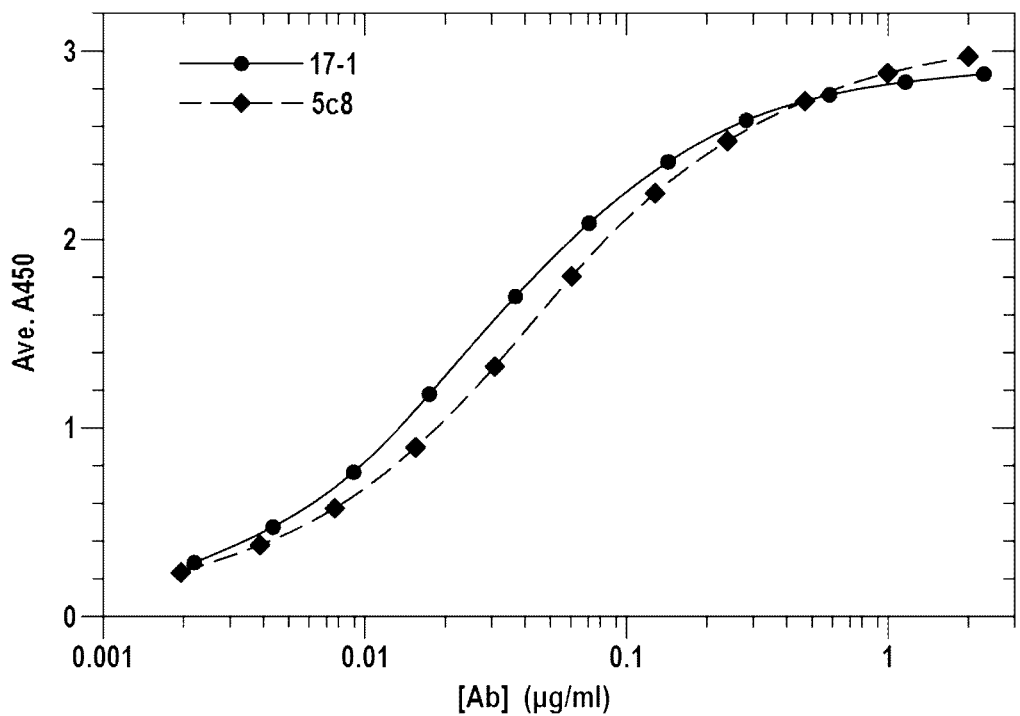
Figure 2H:
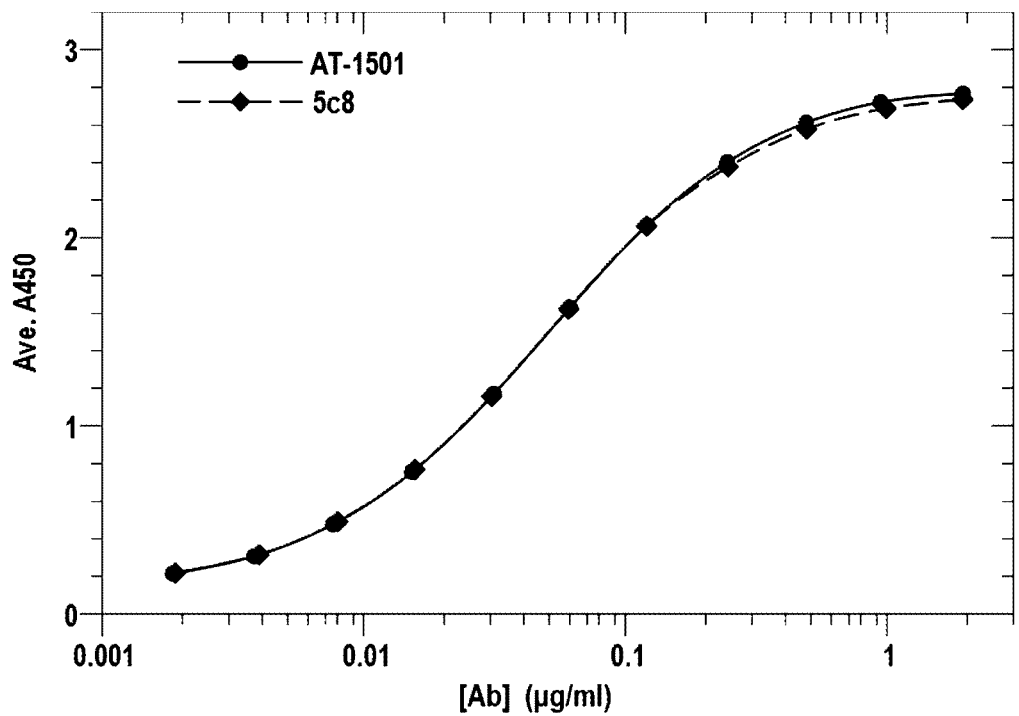
FIG. 2H shows the binding curves of AT-1501 and 5c8.
Figure 2I:
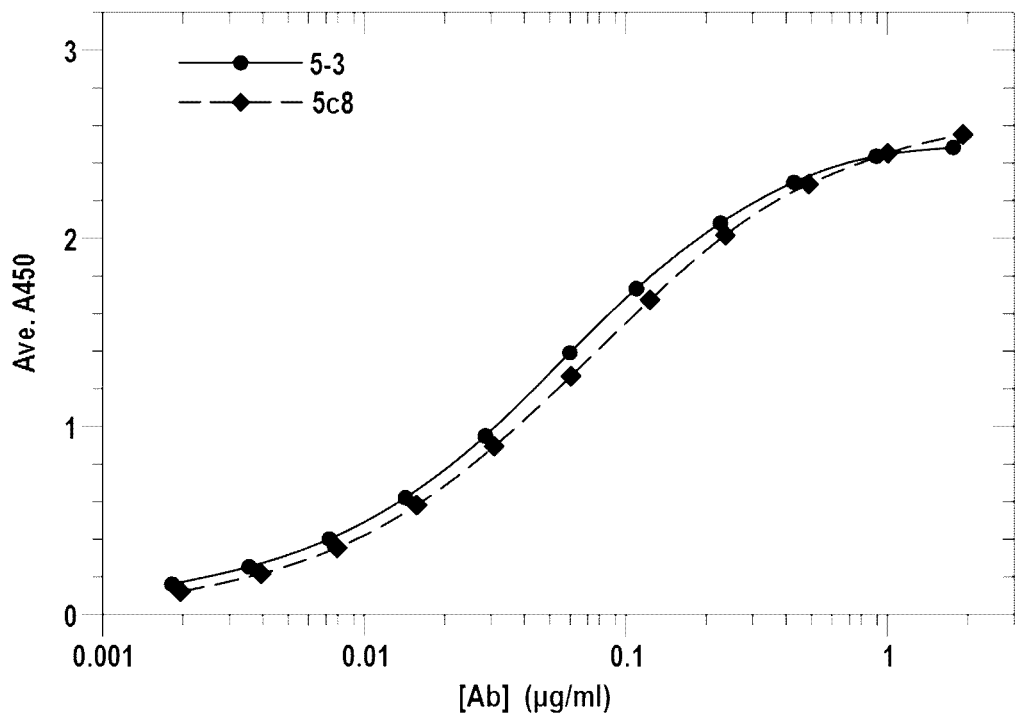
Figure 2J:
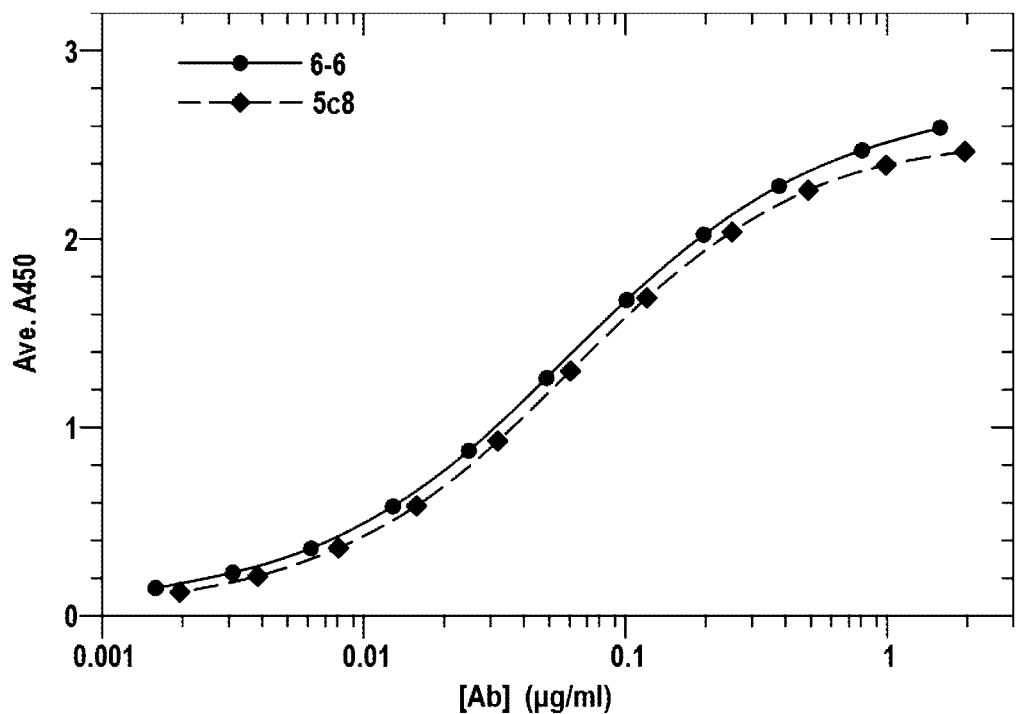
Figure 2K:
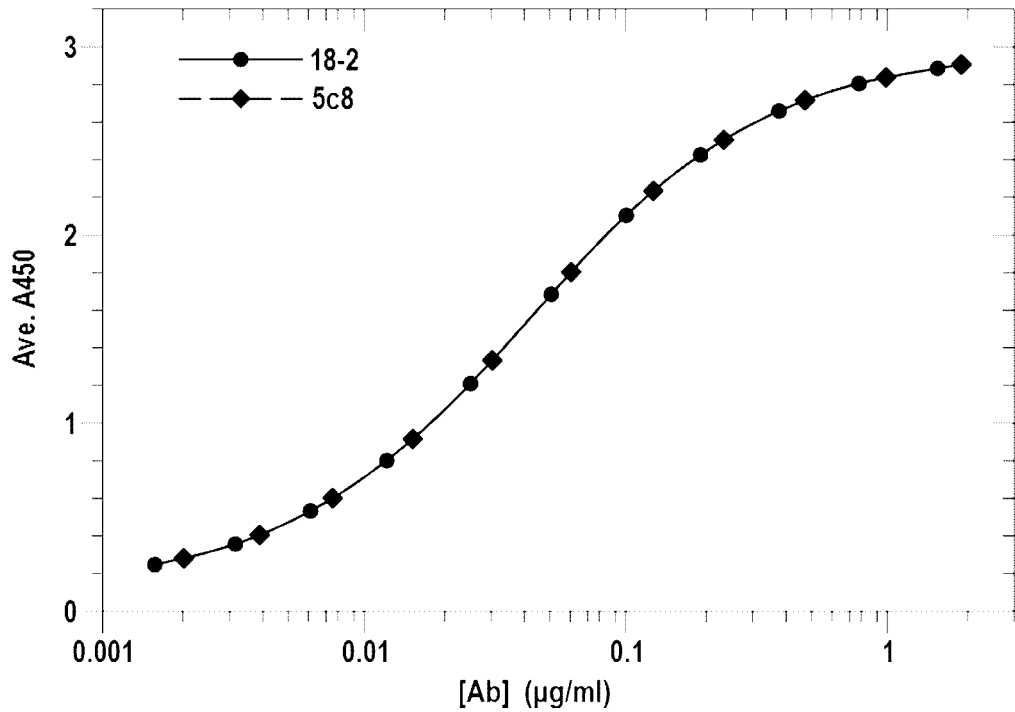
Figure 2L:
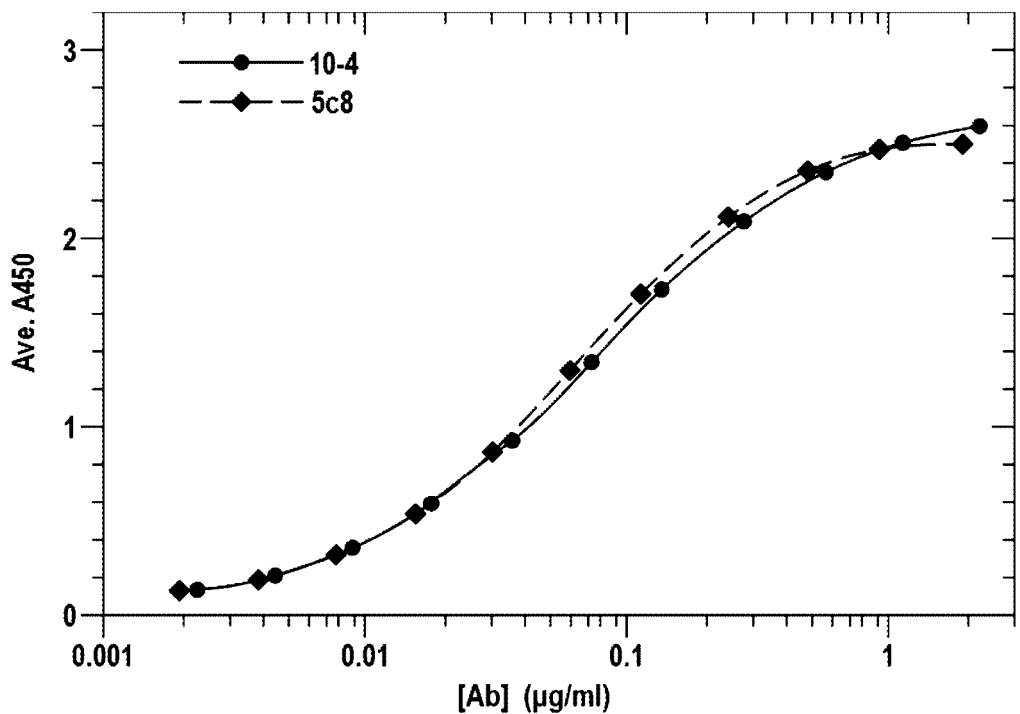
Figure 2M:
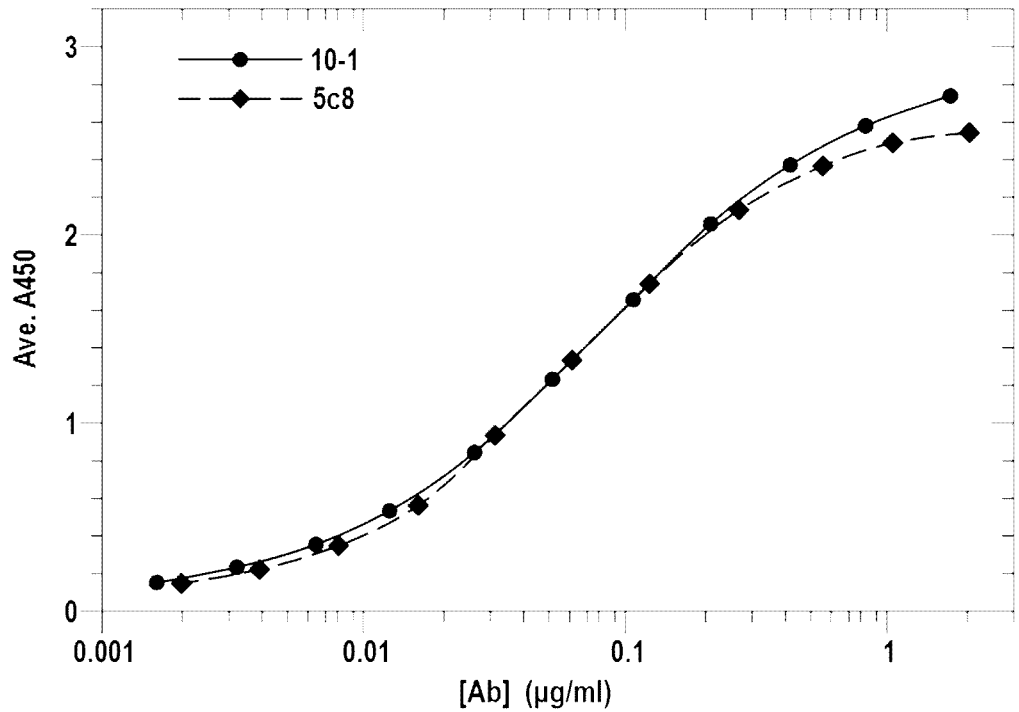
Figure 2N:
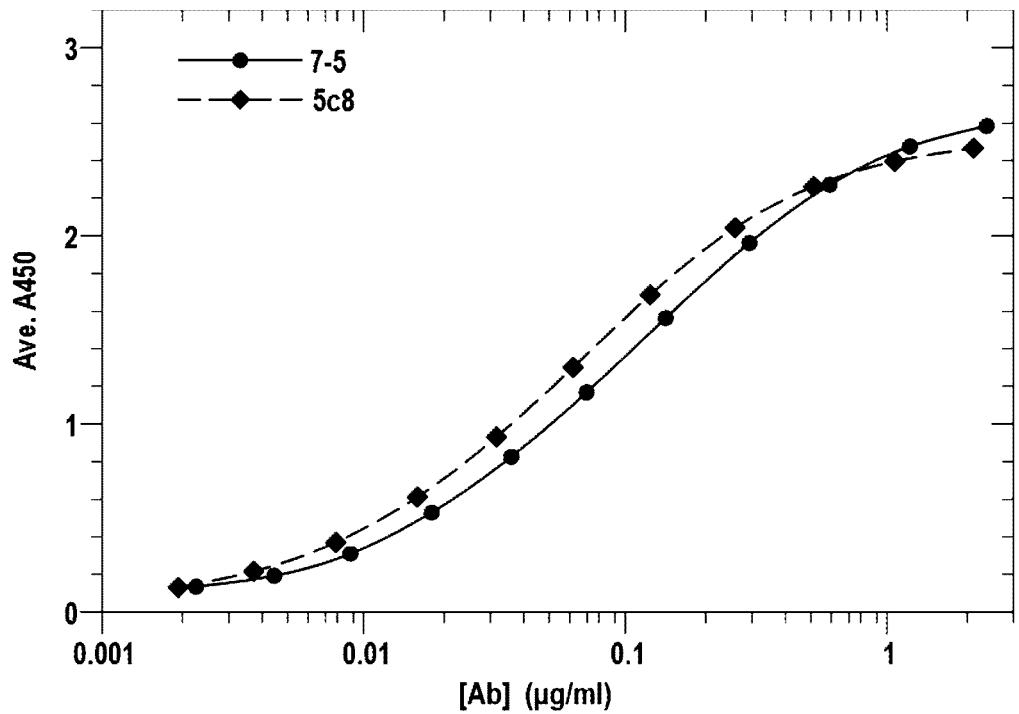
Figure 2O:
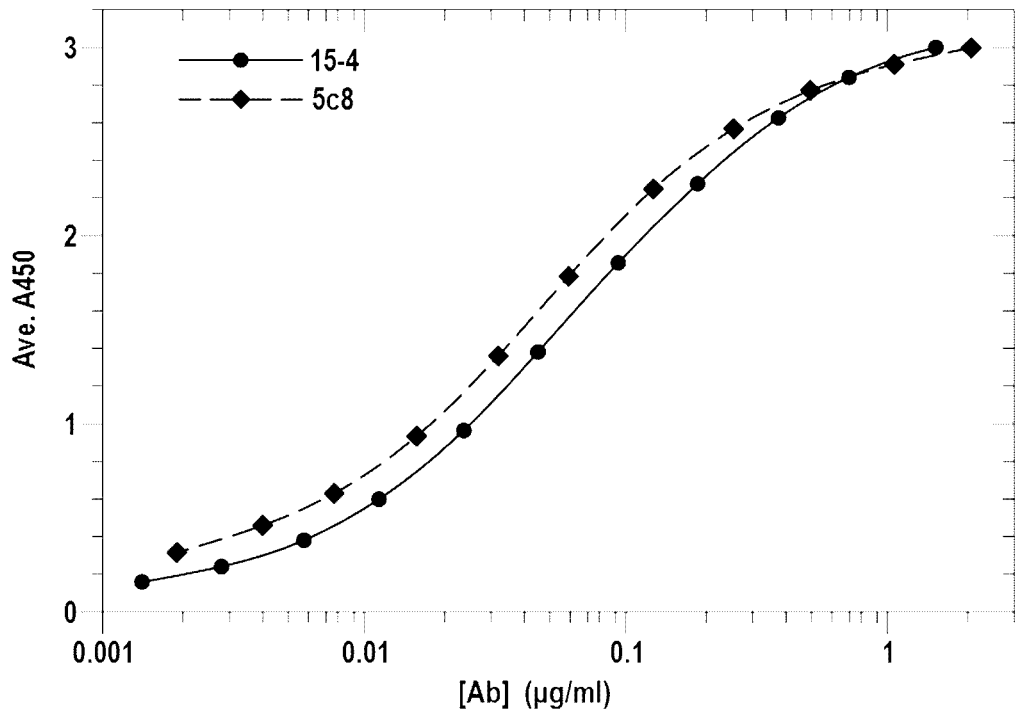
Figure 2P:
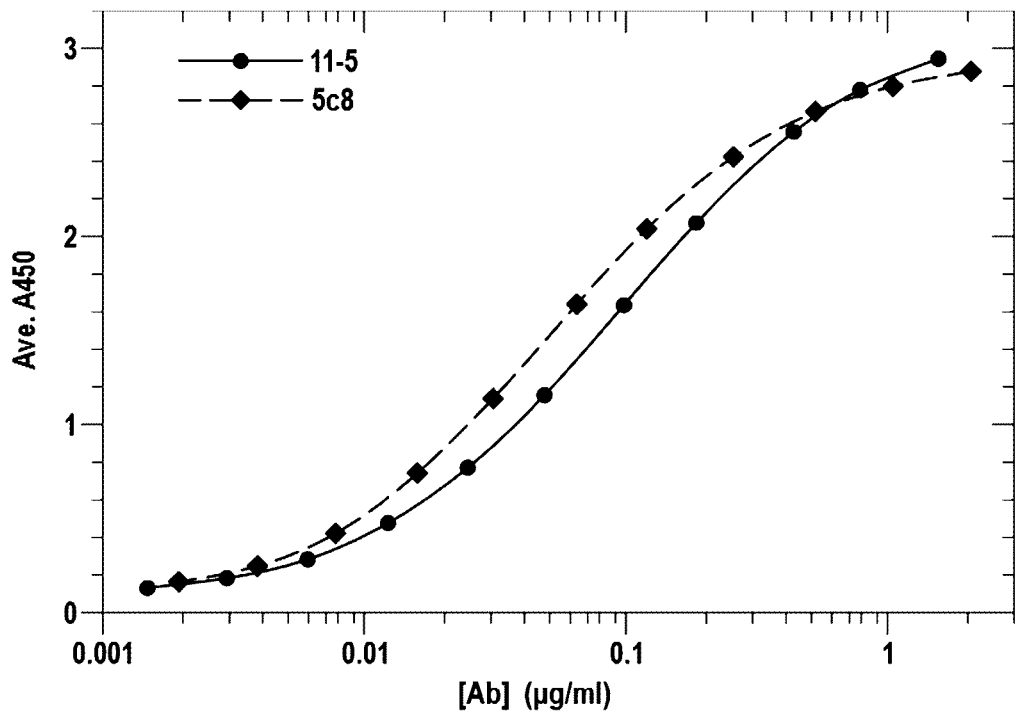
Figure 2Q:
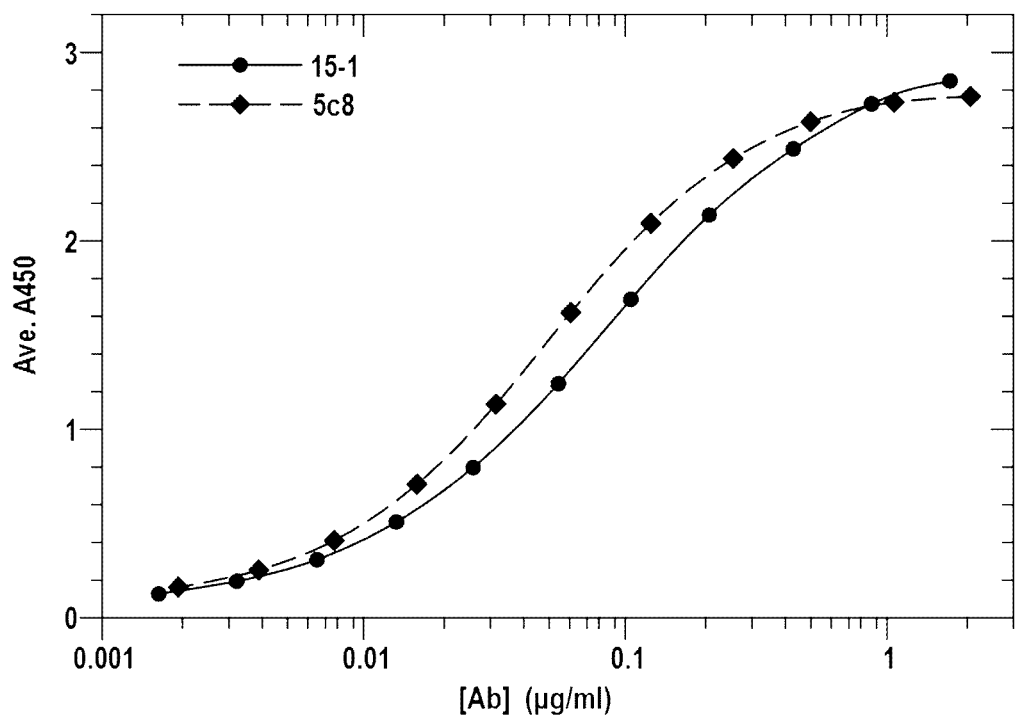
Figure 3A:
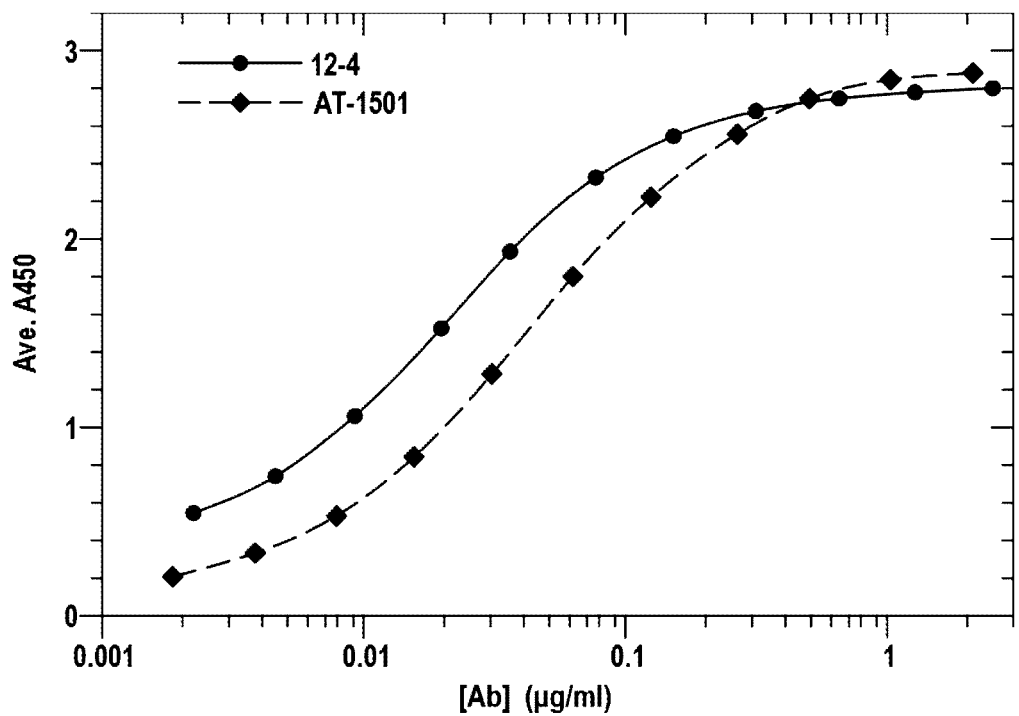
FIGS. 3A-3G and 3I-3Q show the binding curves of the antibodies from each of the clones with the binding curve for AT-1501.
Figure 3B:
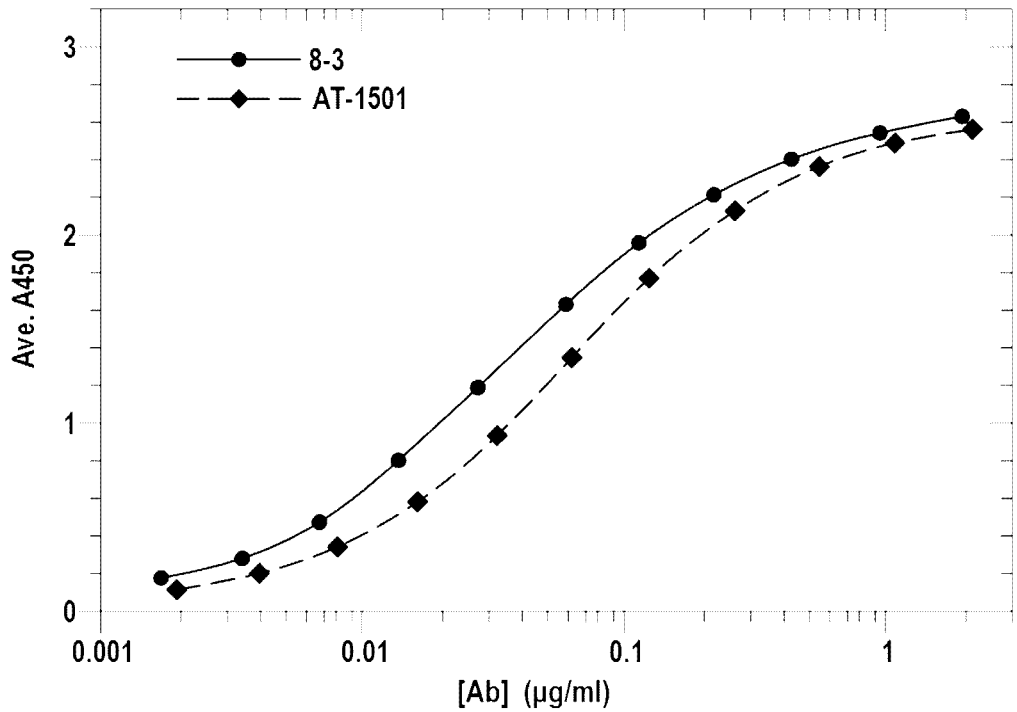
Figure 3C:
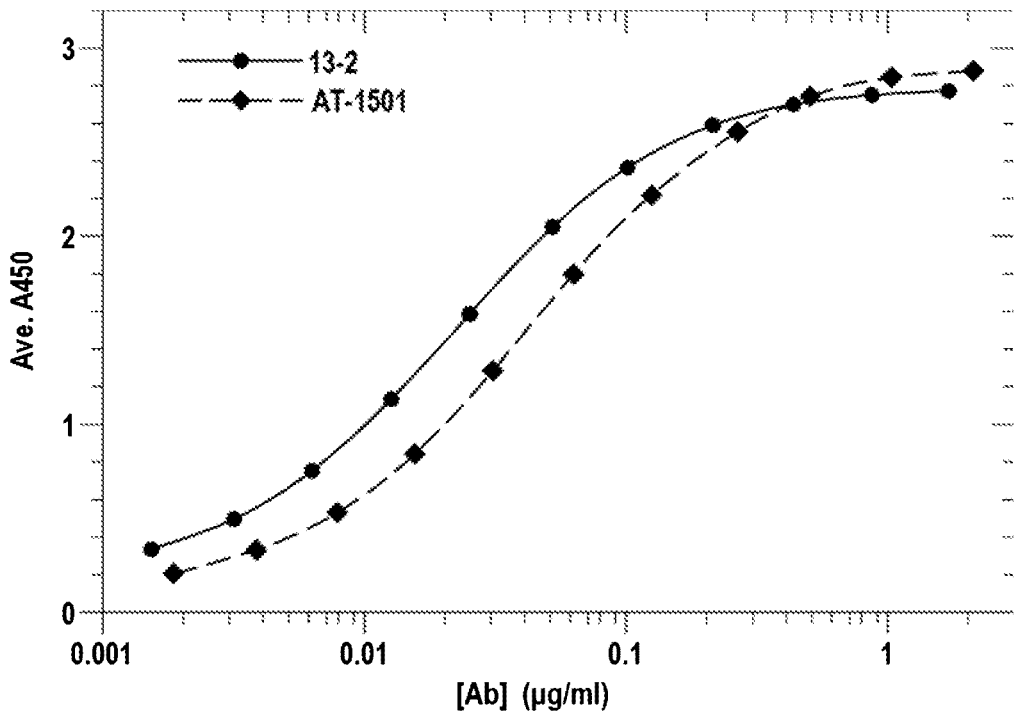
Figure 3D:
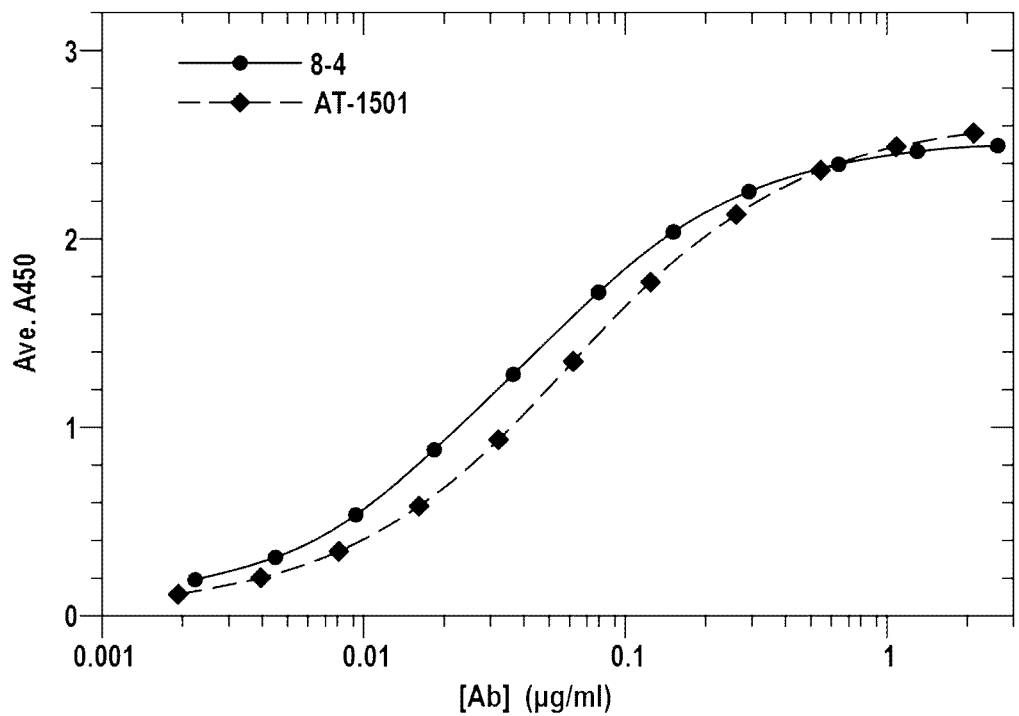
Figure 3E:
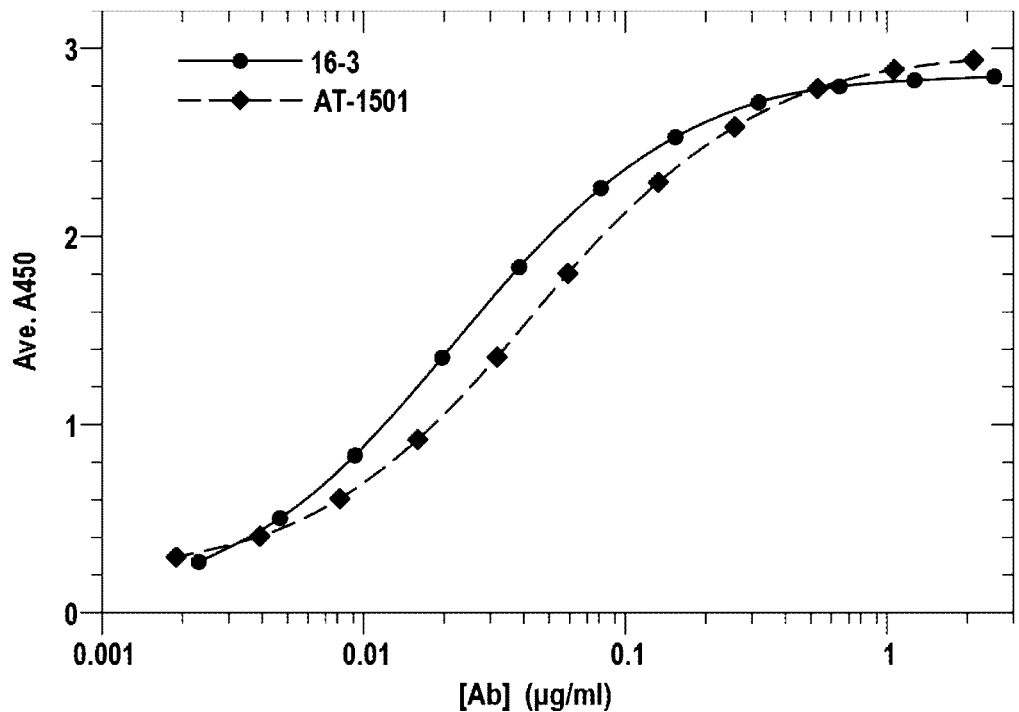
Figure 3F:
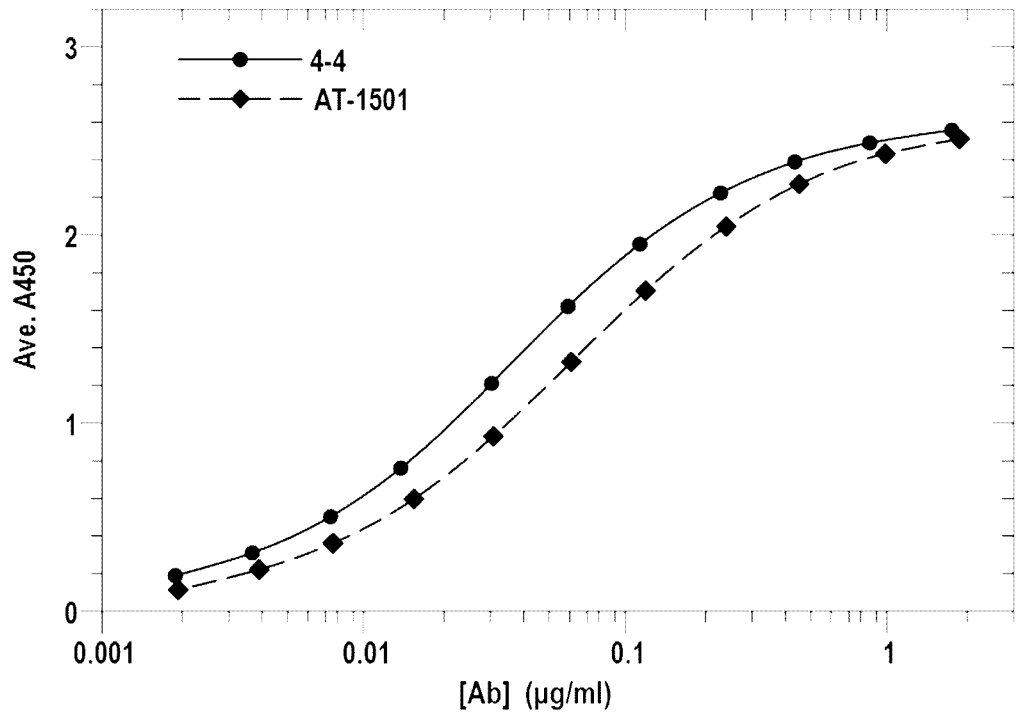
Figure 3G:
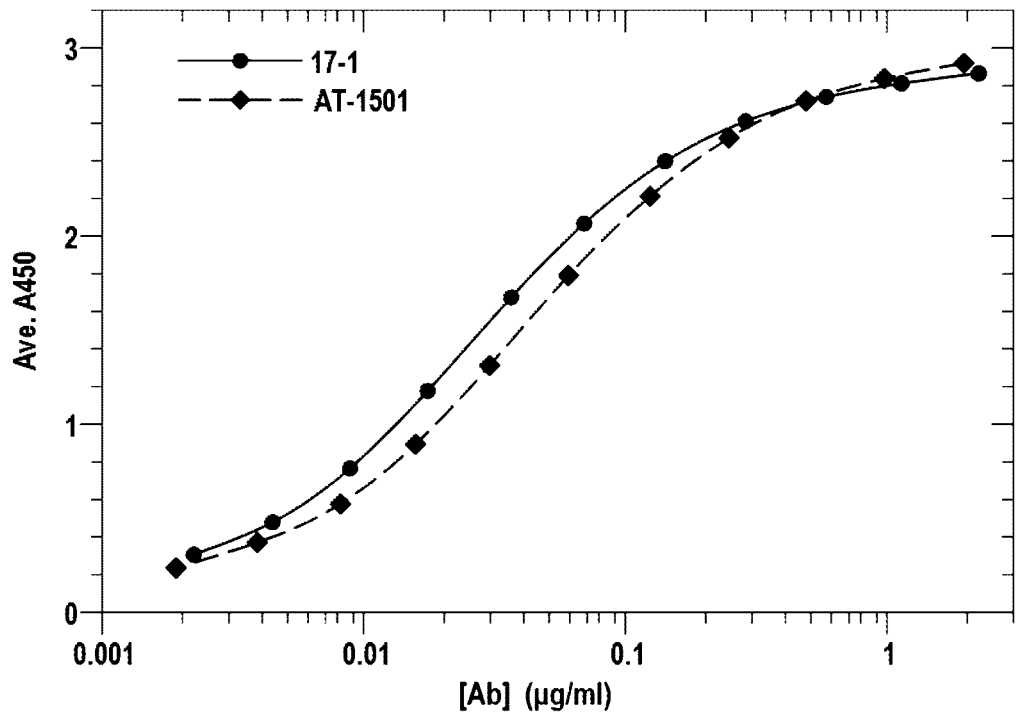
Figure 3H:
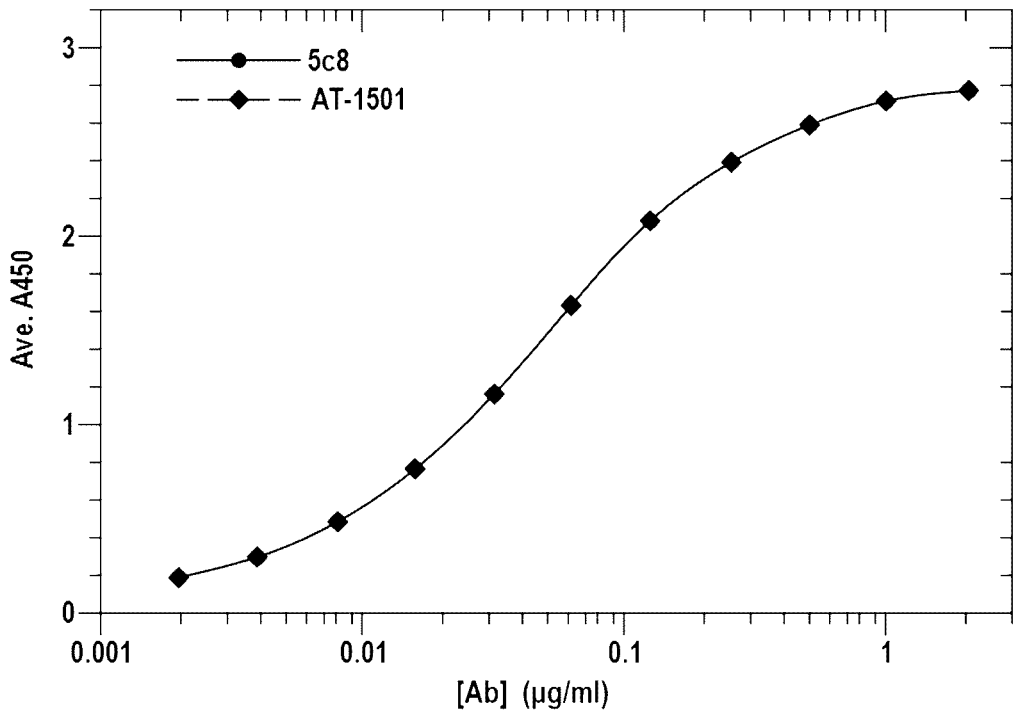
FIG. 3H shows the binding curves of AT-1501 and 5c8.
Figure 3I:
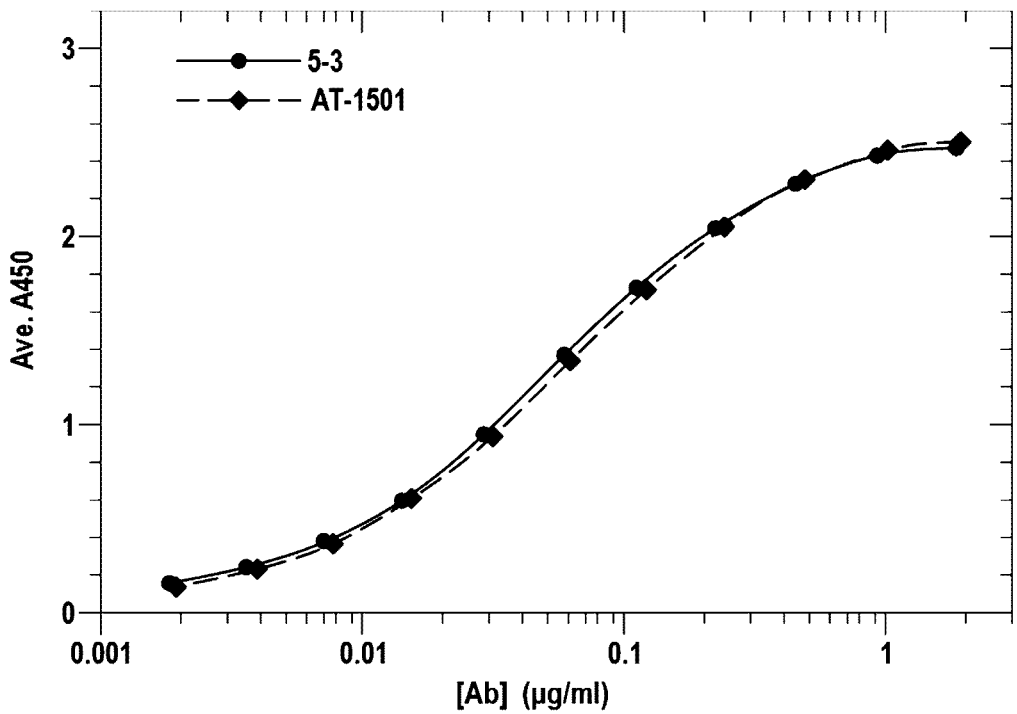
Figure 3J:
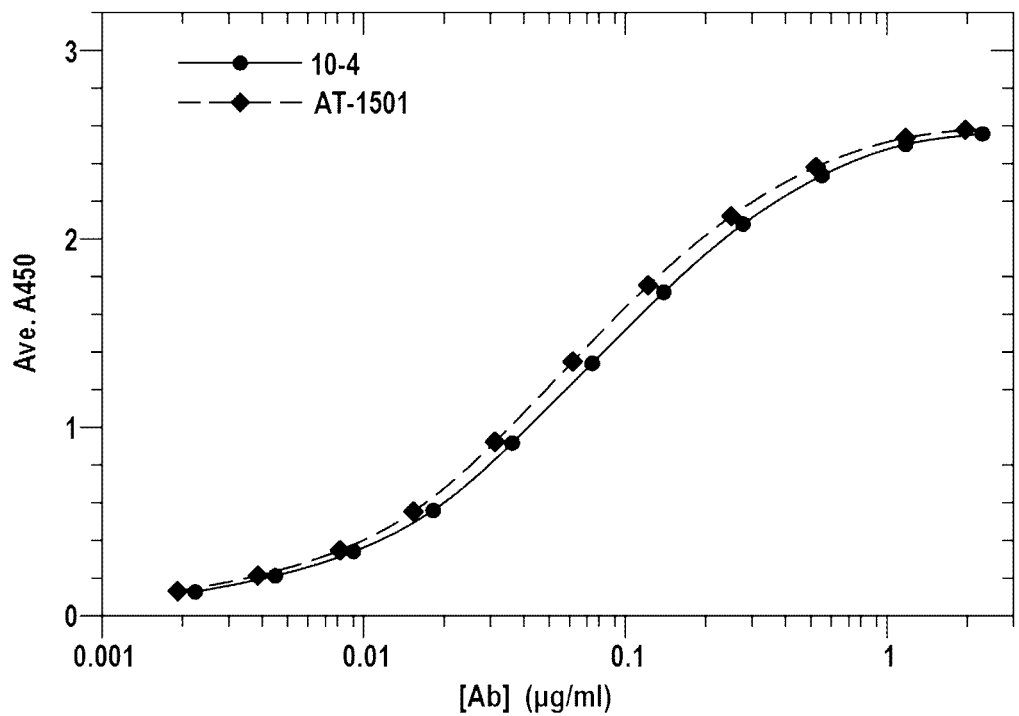
Figure 3K:
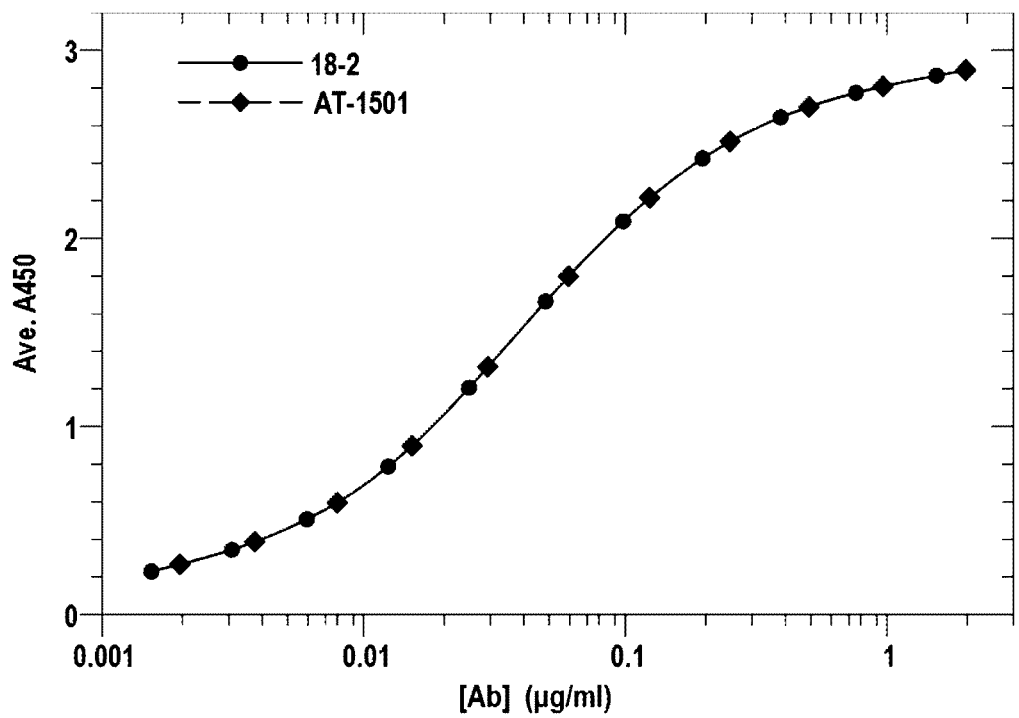
Figure 3L:
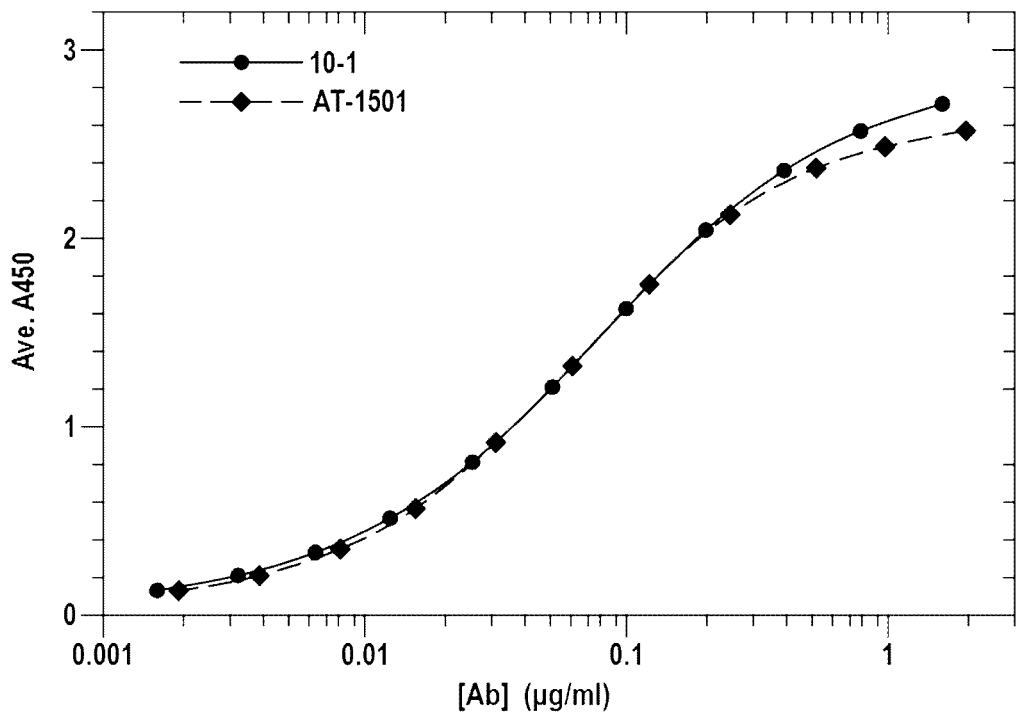
Figure 3M:
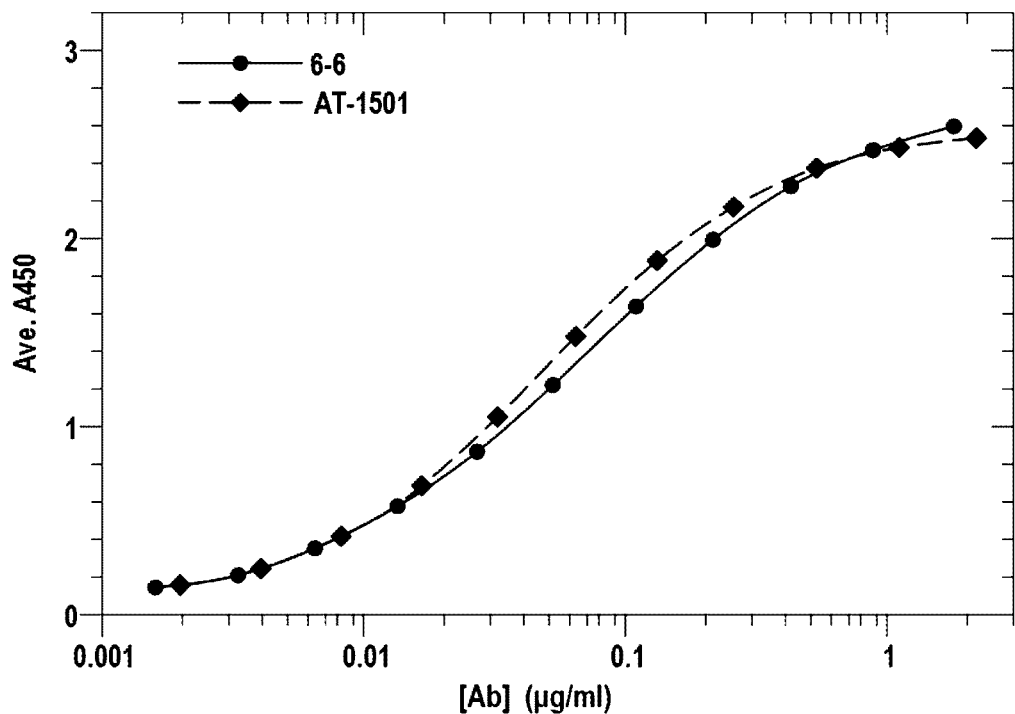
Figure 3N:
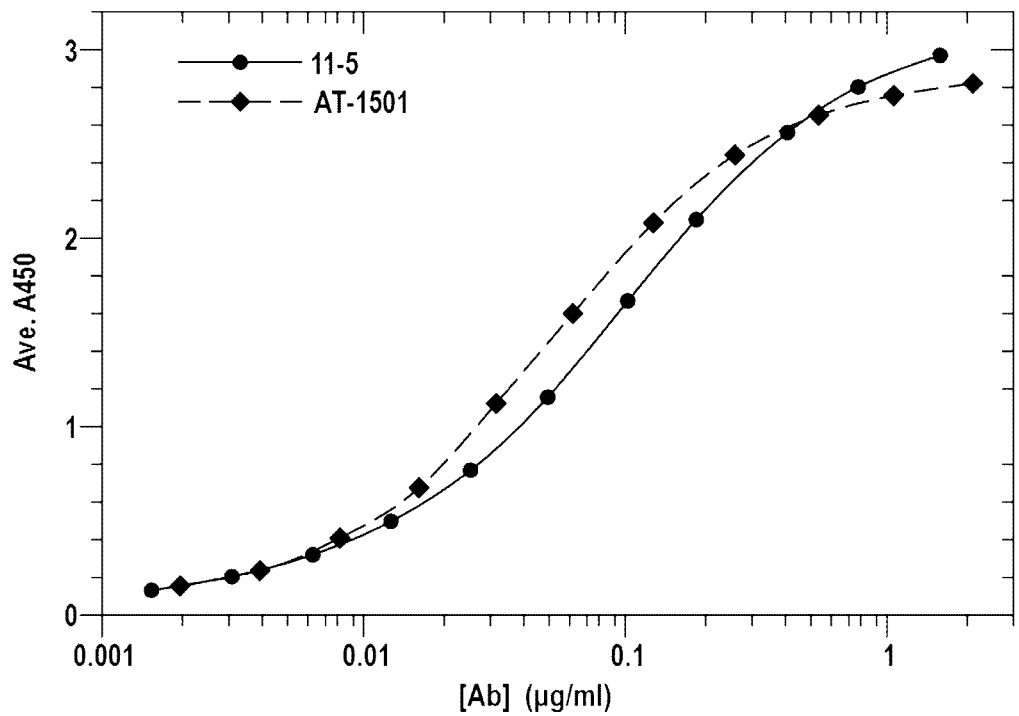
Figure 3O:
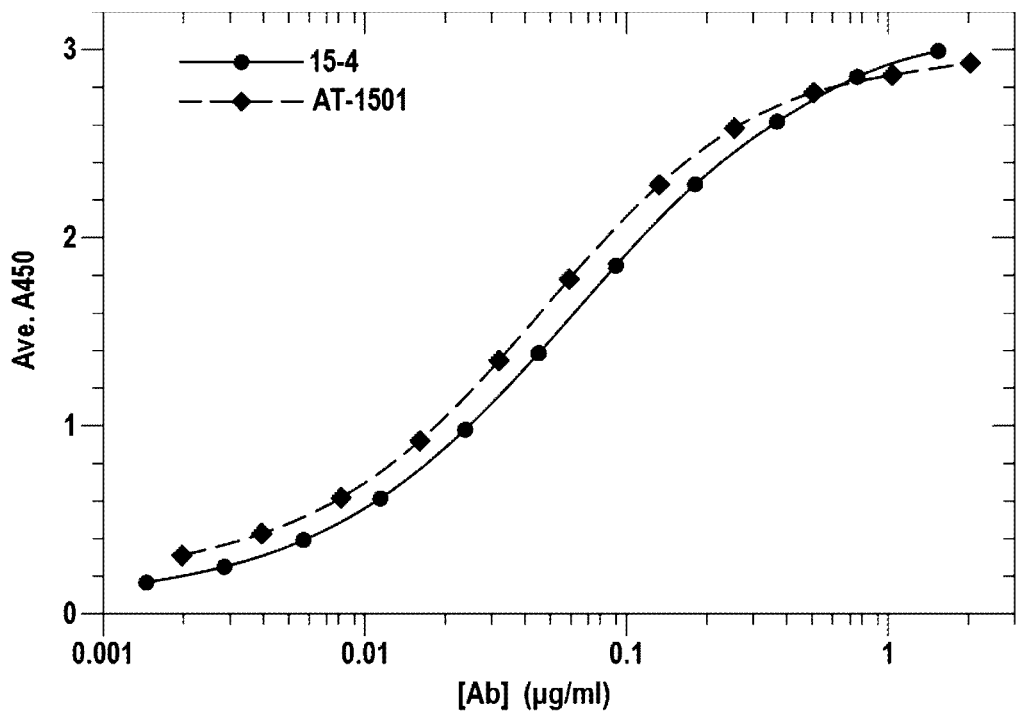
Figure 3P:
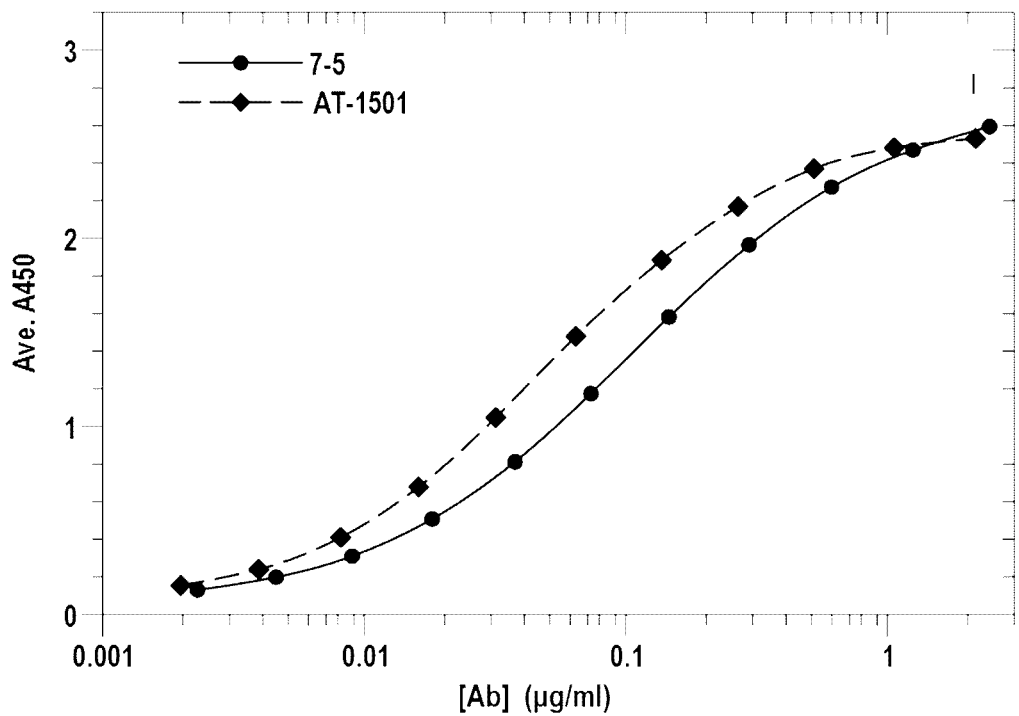
Figure 3Q:
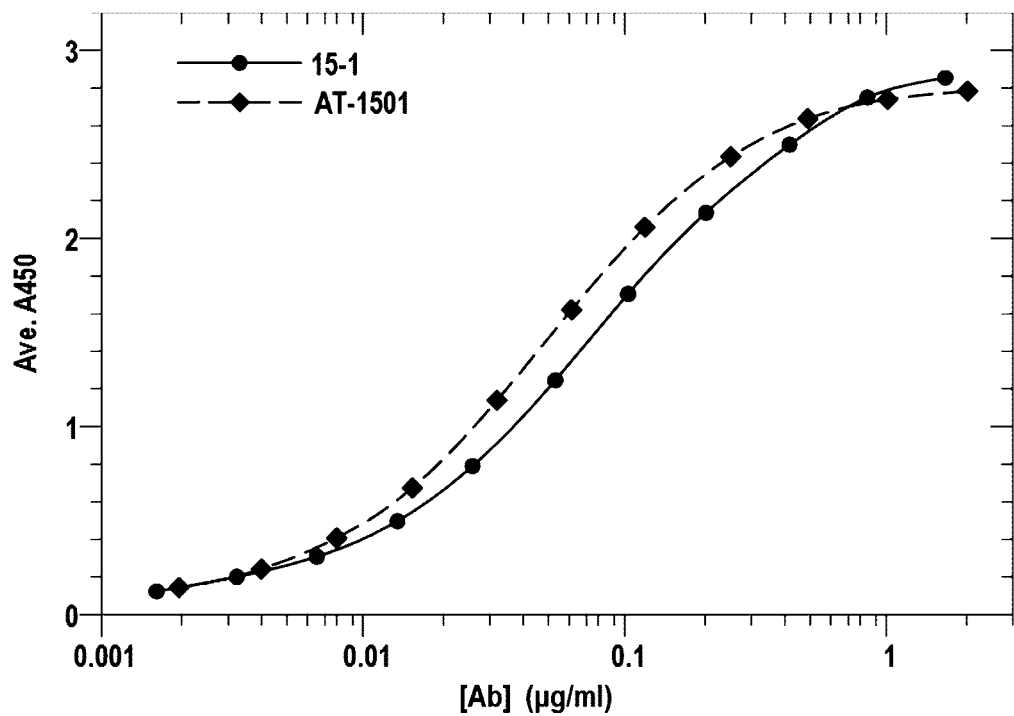

Relative CD40L binding potency was calculated as follows: [IC50 (clone)/IC50 (5c8 or AT-1501)×100%]. The ranked potency of the 16 clones versus 5c8 is shown in FIG. 1A and the ranked potency versus AT-1501 is shown in FIG. 1B. The resulting binding curves are shown in FIGS. 2A-2Q (comparison of 16 clones versus 5c8, FIG. 2H shows the comparison between AT-1501 and 5c8) and FIGS. 3A-3Q (comparison of the 16 clones versus AT-1501, FIG. 3H shows the comparison between AT-1501 and 5c8). The IC50, LCL, UCL and Relative Potency for each clone are shown in Table 2 (comparison with 5c8) and Table 3 (comparison with AT-1501).

TABLE 2

| FIG. No. | Clone | IC50 | LCL | UCL | Rel. Pot. |
|---|---|---|---|---|---|
| 2A | 16-3 | 0.022 | 0.017 | 0.026 | 46 |
| | 5c8 | 0.047 | 0.040 | 0.054 | |
| 2B | 8-3 | 0.036 | 0.028 | 0.043 | 51 |
| | 5c8 | 0.070 | 0.062 | 0.078 | |
| 2C | 12-4 | 0.020 | 0.013 | 0.027 | 47 |
| | 5c8 | 0.042 | 0.038 | 0.046 | |
| 2D | 8-4 | 0.036 | 0.030 | 0.041 | 51 |
| | 5c8 | 0.070 | 0.062 | 0.078 | |
| 2E | 13-2 | 0.020 | 0.013 | 0.027 | 48 |
| | 5c8 | 0.041 | 0.038 | 0.045 | |
| 2F | 4-4 | 0.037 | 0.029 | 0.045 | 51 |
| | 5c8 | 0.072 | 0.064 | 0.081 | |
| 2G | 17-1 | 0.028 | 0.023 | 0.033 | 63 |
| | 5c8 | 0.044 | 0.036 | 0.053 | |
| 2H | AT-1501 | 0.049 | 0.043 | 0.056 | 95 |
| | 5c8 | 0.052 | 0.046 | 0.058 | |
| 2I | 5-3 | 0.055 | 0.047 | 0.063 | 76 |
| | 5c8 | 0.072 | 0.064 | 0.081 | |
| 2J | 6-6 | 0.065 | 0.059 | 0.070 | 106 |
| | 5c8 | 0.061 | 0.054 | 0.068 | |
| 2K | 18-2 | 0.041 | 0.036 | 0.046 | 92 |
| | 5c8 | 0.044 | 0.036 | 0.053 | |
| 2L | 10-4 | 0.075 | 0.065 | 0.086 | 113 |
| | 5c8 | 0.067 | 0.058 | 0.076 | |
| 2M | 10-1 | 0.079 | 0.070 | 0.089 | 119 |
| | 5c8 | 0.067 | 0.058 | 0.076 | |
| 2N | 7-5 | 0.102 | 0.094 | 0.111 | 168 |
| | 5c8 | 0.061 | 0.054 | 0.068 | |
| 2O | 15.4 | 0.063 | 0.056 | 0.069 | 133 |
| | 5c8 | 0.047 | 0.040 | 0.054 | |
| 2P | 11-5 | 0.092 | 0.071 | 0.112 | 177 |
| | 5c8 | 0.052 | 0.046 | 0.058 | |
| 2Q | 15-1 | 0.081 | 0.073 | 0.089 | 163 |
| | 5c8 | 0.050 | 0.046 | 0.053 | |

TABLE 3

| FIG. No. | Clone | IC50 | LCL | UCL | Rel. Pot. |
|---|---|---|---|---|---|
| 3A | 12-4 | 0.020 | 0.013 | 0.027 | 45 |
| | AT-1501 | 0.044 | 0.039 | 0.049 | |
| 3B | 8-3 | 0.036 | 0.028 | 0.043 | 59 |
| | AT-1501 | 0.060 | 0.053 | 0.068 | |
| 3C | 13-2 | 0.020 | 0.013 | 0.027 | 45 |
| | AT-1501 | 0.044 | 0.038 | 0.049 | |
| 3D | 8-4 | 0.036 | 0.030 | 0.041 | 59 |
| | AT-1501 | 0.060 | 0.053 | 0.068 | |
| 3E | 16-3 | 0.022 | 0.017 | 0.026 | 48 |
| | AT-1501 | 0.045 | 0.039 | 0.051 | |
| 3F | 4-4 | 0.037 | 0.029 | 0.045 | 60 |
| | AT-1501 | 0.062 | 0.054 | 0.070 | |

TABLE 3-continued

| FIG. No. | Clone | IC50 | LCL | UCL | Rel. Pot. |
|---|---|---|---|---|---|
| 3G | 17-1 | 0.028 | 0.023 | 0.033 | 66 |
|  | AT-1501 | 0.042 | 0.035 | 0.050 |  |
| 3H | 5c8 | 0.052 | 0.046 | 0.058 | 105 |
|  | AT-1501 | 0.049 | 0.043 | 0.056 |  |
| 3I | 5-3 | 0.055 | 0.047 | 0.063 | 89 |
|  | AT-1501 | 0.062 | 0.054 | 0.070 |  |
| 3J | 10-4 | 0.075 | 0.065 | 0.086 | 115 |
|  | AT-1501 | 0.066 | 0.056 | 0.076 |  |
| 3K | 18-2 | 0.041 | 0.036 | 0.046 | 96 |
|  | AT-1501 | 0.042 | 0.035 | 0.050 |  |
| 3L | 10-1 | 0.079 | 0.070 | 0.089 | 121 |
|  | AT-1501 | 0.066 | 0.056 | 0.076 |  |
| 3M | 6-6 | 0.065 | 0.059 | 0.070 | 132 |
|  | AT-1501 | 0.049 | 0.047 | 0.051 |  |
| 3N | 11-5 | 0.092 | 0.071 | 0.112 | 174 |
|  | AT-1501 | 0.053 | 0.050 | 0.056 |  |
| 3O | 15-4 | 0.063 | 0.056 | 0.069 | 139 |
|  | AT-1501 | 0.045 | 0.039 | 0.051 |  |
| 3P | 7-5 | 0.102 | 0.094 | 0.111 | 210 |
|  | AT-1501 | 0.049 | 0.047 | 0.051 |  |
| 3Q | 15-1 | 0.081 | 0.073 | 0.089 | 159 |
|  | AT-1501 | 0.051 | 0.046 | 0.055 |  |

Example 2 Binding Activity to Human FcγRI, FcγRIIa, FcγRIIIa and FcγRIIIb

The 16 VH/VL antibody clones constructed with an IgG1 Fc having two mutations P238S and N297G (SEQ ID NO: 21). These antibody clones were assayed for Fc effector function for binding to human FcγRI, FcγRIIa and FcγRIIIa.

Anti-CD40L antibodies (Abatacept included as negative control) are diluted to 2 ug/ml in (1×) PBS and 50 ul/well was added to Costar 96-well ½ area high binding assay plates (Corning 3690) for overnight incubation at 4° C. Plates were blocked with (1×) PBS/1.0% BSA (140 ul/well) for 1 hour at room temperature to prevent background binding. Binding curves of recombinant human FcγRI, IIa, IIIa and IIIb (from 5 ug/ml out serial 2-fold dilutions) were added (50 ul/well) and incubated for 1 hour at room temperature. Plates were washed and incubated with mouse anti-human CD16 (anti-FcRIII); CD32 (anti-FcRIIa) or CD64 (anti-FcRI) (eBioSciences/Invitrogen 14-0168-82; 16-0329-81; 14-0649-82) at 2 ug/ml (50 ul/well) for 1 hour at room temperature. Plates were washed and incubated with HRP-(Fab$_2$) goat anti-mouse IgG (Fc specific) (Jackson Immuno. 116-036-071) at a 1:10,000 dilution (50 ul/well) for 1 hour at room temperature. Plates were washed and TMB substrate (Surmodics BioFX TMBW-1000-01) was added (50 ul/well). Color development was stopped after 5 mins at room temperature with (25 ul/well) 2NH$_2$SO$_4$. Plates were read on Molecular Devices SpectraMax M5 plate reader using SoftMax Pro 6.2.2 program to determine absorbance at 450 nm.

Figure 4A:
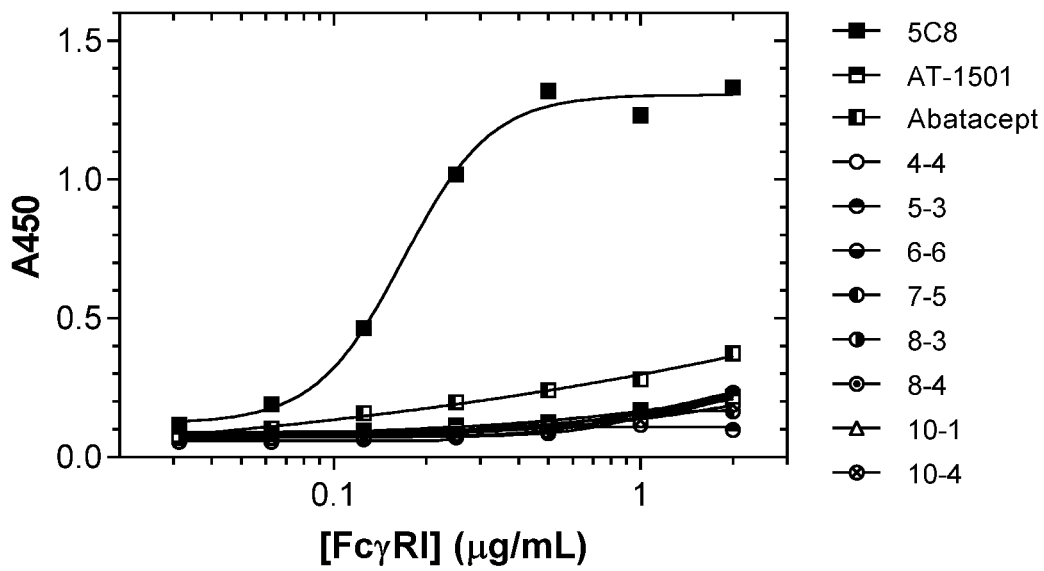
FIGS. 4A and 4B are graphs, each of which shows binding of eight of the antibody clones, 5c8, AT-1501 and abatacept to FcγRI. The only antibody having significant binding is the 5c8 antibody.
Figure 4B:
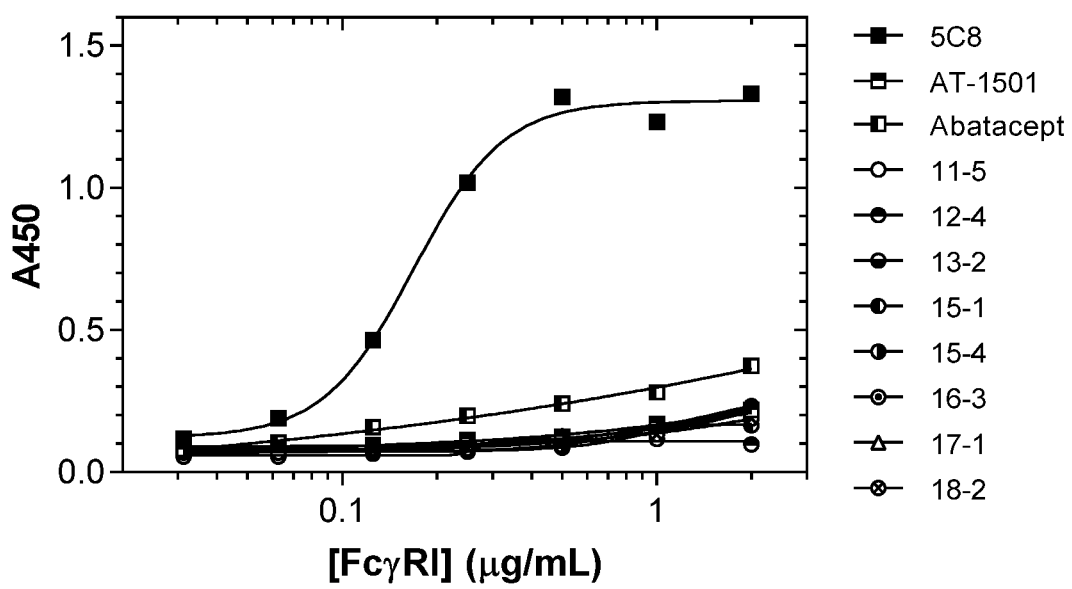
Figure 5A:
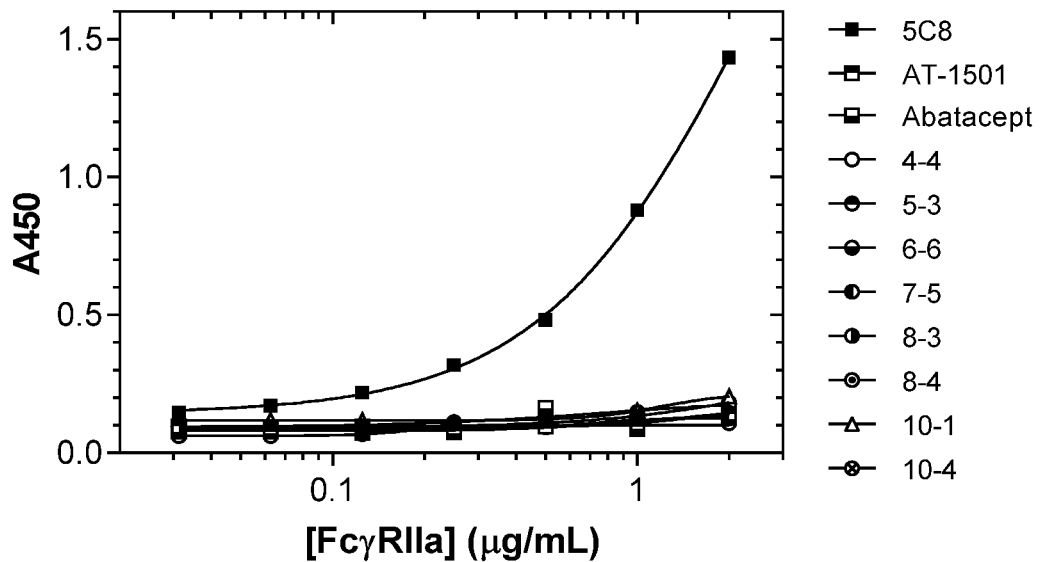
FIGS. 5A and 5B are graphs, each of which shows binding of eight of the antibody clones, 5c8, AT-1501 and abatacept to FcγRIIa. The only antibody having significant binding is the 5c8 antibody.
Figure 5B:
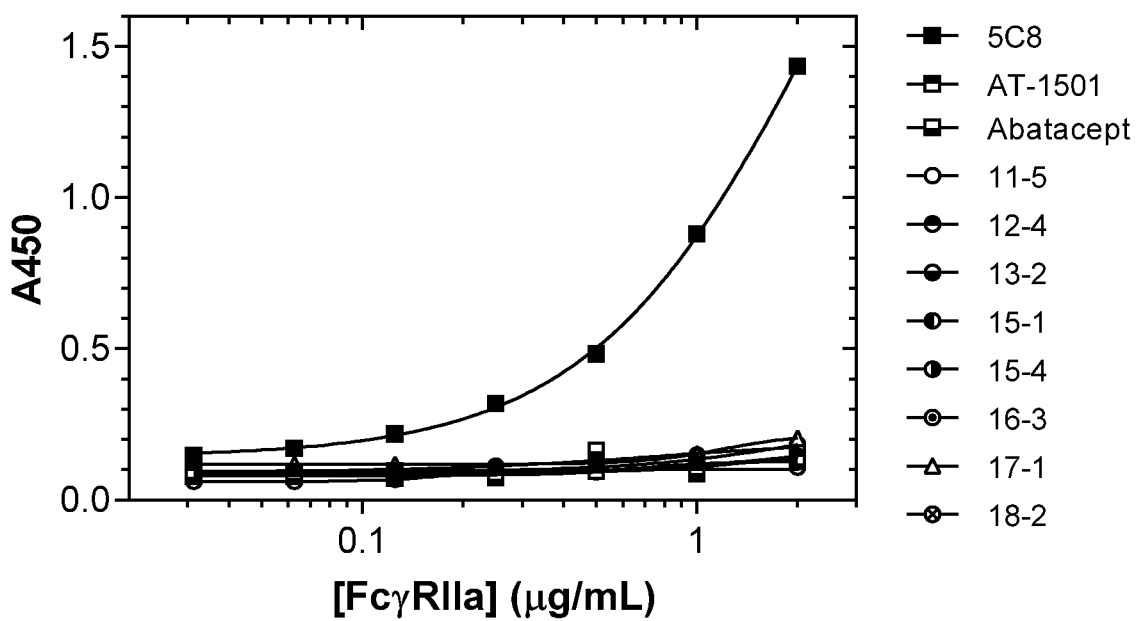

As can be seen in the figures, the clones disclosed in this application were negative for binding to the three Fc receptors while 5c8 bound to FcγRI, FcγRIIa but not to FcγRIIIa or FcγRIIIb. Each of FIGS. 4A and 4B show the binding to FcγRIa for eight antibody clones compared with the binding curves of 5c8, AT-1501 and Abatacept. Each of FIGS. 5A and 5B show the binding to FcγRIIa for eight antibody clones compared with the binding curve of 5c8, AT-1501 and Abatacept. Each of FIGS. 6A and 6B show the binding to FcγRIIIa for eight antibody clones compared with the binding curves of 5c8, AT-1501 and Abatacept. Each of FIGS. 6C and 6D show the binding to FcγRIIIb for eight antibody clones compared with the binding curves of 5c8, AT-1501 and Abatacept. (FIGS. 4A, 5A, 6A and 6A show results from antibody clones 4-4, 5-3, 6-6, 7-5, 8-3, 8-4, 10-1 and 10-4, FIGS. 4B, 5B, 6C and 6D show results from antibody clones 11-5, 12-4, 13-2, 15-1, 15-4, 16-3, 17-1 and 18-2).

Example 4 Binding Activity to C1q

Anti-CD40L antibodies (Abatacept included as negative control) were diluted to 2 ug/ml in (1×) PBS and 50 ul/well was added to Costar 96-well ½ area high binding assay plates (Corning 3690) for overnight incubation at 4° C. Plates were blocked with (1×) PBS/1.0% BSA (140 ul/well) for 1 hour at room temperature to prevent background binding. Binding curves of natural human C1q protein (Abcam ab96363) from 10 ug/ml out serial 2-fold dilutions were added (50 ul/well) for 1 hour at room temperature. Plates were washed and HRP-sheep anti-human C1q (Abcam ab46191) is added at a 1:400 dilution (50 ul/well) and incubated for 1 hour at room temperature. Plates were washed and TMB substrate (Surmodics BioFX TMBW-1000-01) is added (50 ul/well). Color development was stopped after 5 minutes at room temperature with (25 ul/well) 2NH$_2$SO$_4$. Plates were read on Molecular Devices SpectraMax M5 plate reader using SoftMax Pro 6.2.2 program to determine absorbance at 450 nm.

As can be seen in the figures, the antibody from all sixteen antibody clones disclosed in this application were negative for binding to C1q while 5c8 showed significant binding. Each of FIGS. 7A and 7B show the binding to C1q for eight antibody clones compared with the binding curves of 5c8, AT-1501 and Abatacept. FIG. 7A shows results from antibody clones 4-4, 5-3, 6-6, 7-5, 8-3, 8-4, 10-1 and 10-4 and 7B shows results from antibody clones 11-5, 12-4, 13-2, 15-1, 15-4, 16-3, 17-1 and 18-2.

What is claimed is:

1. An isolated antibody or antigen-binding fragment thereof, comprising:
   (a) a heavy chain variable region ($V_H$) having the amino acid sequence as set forth in SEQ ID NO: 1 and the light chain variable region ($V_L$) having the amino acid sequence as set forth in SEQ ID NO: 5; or
   (b) a heavy chain variable region ($V_H$) having the amino acid sequence as set forth in SEQ ID NO: 1 and the light chain variable region ($V_L$) having the amino acid sequence as set forth in SEQ ID NO: 6; or
   (c) a heavy chain variable region ($V_H$) having the amino acid sequence as set forth in SEQ ID NO: 1 and the light chain variable region ($V_L$) having the amino acid sequence as set forth in SEQ ID NO: 7; or
   (d) a heavy chain variable region ($V_H$) having the amino acid sequence as set forth in SEQ ID NO: 1 and the light chain variable region ($V_L$) having the amino acid sequence as set forth in SEQ ID NO: 8; or
   (e) a heavy chain variable region ($V_H$) having the amino acid sequence as set forth in SEQ ID NO: 2 and the light chain variable region ($V_L$) having the amino acid sequence as set forth in SEQ ID NO: 5; or
   (f) a heavy chain variable region ($V_H$) having the amino acid sequence as set forth in SEQ ID NO: 2 and the light chain variable region ($V_L$) having the amino acid sequence as set forth in SEQ ID NO: 6; or
   (g) a heavy chain variable region ($V_H$) having the amino acid sequence as set forth in SEQ ID NO: 2 and the light chain variable region ($V_L$) having the amino acid sequence as set forth in SEQ ID NO: 7; or
   (h) a heavy chain variable region ($V_H$) having the amino acid sequence as set forth in SEQ ID NO: 2 and the light chain variable region ($V_L$) having the amino acid sequence as set forth in SEQ ID NO: 8; or
   (i) a heavy chain variable region ($V_H$) having the amino acid sequence as set forth in SEQ ID NO: 3 and the light chain variable region ($V_L$) having the amino acid sequence as set forth in SEQ ID NO: 5; or
   (j) a heavy chain variable region ($V_H$) having the amino acid sequence as set forth in SEQ ID NO: 3 and the light chain variable region ($V_L$) having the amino acid sequence as set forth in SEQ ID NO: 6; or
   (k) a heavy chain variable region ($V_H$) having the amino acid sequence as set forth in SEQ ID NO: 3 and the light chain variable region ($V_L$) having the amino acid sequence as set forth in SEQ ID NO: 7; or
   (l) a heavy chain variable region ($V_H$) having the amino acid sequence as set forth in SEQ ID NO: 3 and the light chain variable region ($V_L$) having the amino acid sequence as set forth in SEQ ID NO: 8; or
   (m) a heavy chain variable region ($V_H$) having the amino acid sequence as set forth in SEQ ID NO: 4 and the light chain variable region ($V_L$) having the amino acid sequence as set forth in SEQ ID NO: 5; or
   (n) a heavy chain variable region ($V_H$) having the amino acid sequence as set forth in SEQ ID NO: 4 and the light chain variable region ($V_L$) having the amino acid sequence as set forth in SEQ ID NO: 6; or
   (o) a heavy chain variable region ($V_H$) having the amino acid sequence as set forth in SEQ ID NO: 4 and the light chain variable region ($V_L$) having the amino acid sequence as set forth in SEQ ID NO: 7; or
   (p) a heavy chain variable region ($V_H$) having the amino acid sequence as set forth in SEQ ID NO: 4 and the light chain variable region (V$_L$) having the amino acid sequence as set forth in SEQ ID NO.

2. The isolated antibody or antigen binding fragment thereof, according to claim 1, wherein the antibody is of the IgG1 isotype, and wherein the heavy chain constant region comprises the amino acid sequence as set forth in SEQ ID NO: 21, SEQ ID NO: 22, SEQ ID NO: 23, or SEQ ID NO: 24.

3. The isolated antibody according to claim 2, wherein the antibody further comprises a light chain constant region wherein the light chain constant region comprises the amino acid sequence set forth in SEQ ID NO: 25.

4. The isolated antibody according to claim 1, wherein the antibody comprises:
(a) a heavy chain having the amino acid sequence as set forth in SEQ ID NO: 42 and the light chain having the amino acid sequence as set forth in SEQ ID NO: 38; or
(b) a heavy chain having the amino acid sequence as set forth in SEQ ID NO: 42 and the light chain having the amino acid sequence as set forth in SEQ ID NO: 39; or
(c) a heavy chain having the amino acid sequence as set forth in SEQ ID NO: 42 and the light chain having the amino acid sequence as set forth in SEQ ID NO: 40; or
(d) a heavy chain having the amino acid sequence as set forth in SEQ ID NO: 42 and the light chain having the amino acid sequence as set forth in SEQ ID NO: 41; or
(e) a heavy chain having the amino acid sequence as set forth in SEQ ID NO: 43 and the light chain having the amino acid sequence as set forth in SEQ ID NO: 38; or
(f) a heavy chain having the amino acid sequence as set forth in SEQ ID NO: 43 and the light chain having the amino acid sequence as set forth in SEQ ID NO: 39; or
(g) a heavy chain having the amino acid sequence as set forth in SEQ ID NO: 43 and the light chain having the amino acid sequence as set forth in SEQ ID NO: 40; or
(h) a heavy chain having the amino acid sequence as set forth in SEQ ID NO: 43 and the light chain having the amino acid sequence as set forth in SEQ ID NO: 41; or
(i) a heavy chain having the amino acid sequence as set forth in SEQ ID NO: 44 and the light chain having the amino acid sequence as set forth in SEQ ID NO: 38; or
(j) a heavy chain having the amino acid sequence as set forth in SEQ ID NO: 44 and the light chain having the amino acid sequence as set forth in SEQ ID NO: 39; or
(k) a heavy chain having the amino acid sequence as set forth in SEQ ID NO: 44 and the light chain having the amino acid sequence as set forth in SEQ ID NO: 40; or
(l) a heavy chain having the amino acid sequence as set forth in SEQ ID NO: 44 and the light chain having the amino acid sequence as set forth in SEQ ID NO: 41; or
(m) a heavy chain having the amino acid sequence as set forth in SEQ ID NO: 45 and the light chain having the amino acid sequence as set forth in SEQ ID NO: 38; or
(n) a heavy chain having the amino acid sequence as set forth in SEQ ID NO: 45 and the light chain having the amino acid sequence as set forth in SEQ ID NO: 39; or
(o) a heavy chain having the amino acid sequence as set forth in SEQ ID NO: 45 and the light chain having the amino acid sequence as set forth in SEQ ID NO: 40; or
(p) a heavy chain having the amino acid sequence as set forth in SEQ ID NO: 45 and the light chain having the amino acid sequence as set forth in SEQ ID NO: 41.

5. A method for treating a subject with a CD40L-associated disease or disorder comprising administering to the subject a therapeutically effective amount of an antibody or antibody fragment according to claim 1 wherein the CD40L-associated disease or disorder is selected from the group consisting of systemic lupus erythematous, type-1 diabetes, Myasthenia gravis, psoriasis, Addison's disease, Crohn's disease, uveitis, multiple sclerosis, hemolytic anemia, inflammatory bowel disease, immune thrombocytopenic purpura, Graves' disease, rheumatoid arthritis, Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, Spinocerebellar Ataxia, graft rejection, and organ transplant rejection.

6. The method according to claim 5, wherein the disease or disorder is an autoimmune disease, selected from the group consisting of systemic lupus erythematous, type-1 diabetes, Myasthenia gravis, psoriasis, Addison's disease, Crohn's disease, uveitis, multiple sclerosis, hemolytic anemia, inflammatory bowel disease, immune thrombocytopenic purpura, Graves' disease, and rheumatoid arthritis.

7. The method according to claim 5, wherein the disease or disorder is a neurodegenerative disorder or a neuromuscular disorder selected from the group consisting of Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, or Spinocerebellar Ataxia.

8. The method according to claim 5, wherein the disease or disorder is Amyotrophic Lateral Sclerosis.

9. A method for inhibiting an immune response in a subject comprising administering to the subject a therapeutically effective amount of an antibody or antibody fragment according to claim 1, wherein the immune response is graft vs. host disease, or organ transplant rejection.

10. The method according to claim 5, wherein the antibody or antibody fragment is administered in combination with a compound that blocks the interaction between CD28 and CD86 or between CD28 and CD80, wherein the compound that blocks the interaction between CD28 and CD86 or between CD28 and CD80 is a CTLA4-Ig fusion protein, or the compound that blocks the interaction between CD28 and CD86 or between CD28 and CD80 is abatacept or belatacept or galiximab.

* * * * *